United States Patent
Diller et al.

(10) Patent No.: US 9,983,211 B2
(45) Date of Patent: May 29, 2018

(54) RAPID PROTEIN LABELING AND ANALYSIS

(71) Applicant: LIFE TECHNOLOGIES CORPORATION, Carlsbad, CA (US)

(72) Inventors: Thomas Diller, San Diego, CA (US); Bethany Sutton, La Jolla, CA (US); George Hanson, Eugene, OR (US); Timothy Updyke, Temecula, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days. days.

(21) Appl. No.: 15/138,177

(22) Filed: Apr. 25, 2016

(65) Prior Publication Data

US 2016/0341735 A1  Nov. 24, 2016

Related U.S. Application Data

(60) Division of application No. 14/688,986, filed on Apr. 16, 2015, which is a continuation of application No.
(Continued)

(51) Int. Cl.
*G01N 33/58* (2006.01)
*G01N 33/68* (2006.01)
(Continued)

(52) U.S. Cl.
CPC ....... *G01N 33/582* (2013.01); *G01N 33/6803* (2013.01); *B33Y 80/00* (2014.12); *G01N 2550/00* (2013.01)

(58) Field of Classification Search
CPC .. G01N 33/52; G01N 33/582; G01N 33/6803; G01N 2550/00; B33Y 80/00
(Continued)

(56) References Cited

U.S. PATENT DOCUMENTS 3,625,827 A * 12/1971 Wildi .................. C08F 8/00
                                          435/175
5,631,374 A *  5/1997 Novotny ............. C07D 215/14
                                          436/111
(Continued)

FOREIGN PATENT DOCUMENTS

CA      2599866       9/2006
EP      1770129       4/2007
(Continued)

OTHER PUBLICATIONS

EP 08755796.3; Extended European Search Report dated May 25, 2010, 9 pages.
(Continued)

*Primary Examiner* — Rebecca M Fritchman

(57) ABSTRACT

The present invention provides methods and compositions for labeling, separating and analyzing proteins, particularly a specific protein of interest within a cell lysate or in a mixture of proteins. The proteins are labeled with an amine reactive or thiol reactive fluorescent dye, or an amine reactive fluorogenic reagent that becomes fluorescent upon reacting to amine groups located on the protein. Following the labeling step, the proteins within the mixture can be separated and analyzed. In a further embodiment, a tag binding fluorogenic reagent that can bind to a tag on a tagged protein is added to specifically label the protein of interest.

12 Claims, 23 Drawing Sheets

Related U.S. Application Data

14/079,330, filed on Nov. 13, 2013, which is a division of application No. 12/122,607, filed on May 16, 2008, now Pat. No. 8,609,423.

(60) Provisional application No. 60/938,973, filed on May 18, 2007.

(51) Int. Cl.
  *G01N 33/00* (2006.01)
  *B33Y 80/00* (2015.01)

(58) Field of Classification Search
  USPC .................................. 422/430; 436/86
  See application file for complete search history.

(56) References Cited

U.S. PATENT DOCUMENTS

| | | | |
|---|---|---|---|
| 7,531,317 | B2 | 5/2009 | Fox et al. |
| 8,039,264 | B2 | 10/2011 | Bogoev et al. |
| 2003/0207344 | A1* | 11/2003 | Hammock ............ C07C 255/37 435/18 |
| 2005/0176065 | A1 | 8/2005 | Hanson |
| 2005/0239135 | A1* | 10/2005 | Bogoev .................... C07K 1/13 435/7.1 |

FOREIGN PATENT DOCUMENTS

| | | |
|---|---|---|
| JP | 2006522173 | 9/2006 |
| JP | 4893964 | 3/2011 |
| WO | 2004009598 | 1/2004 |
| WO | 2004085546 | 10/2004 |
| WO | 2006093104 | 9/2006 |
| WO | 2006132030 | 12/2006 |

OTHER PUBLICATIONS

Craig, B. D. et al., "Determination of picomolar concentrations of proteins using novel amno reactive chameleon labels and capillary electrophoresis laser-induced flouroscence detection", *Electrophoresis*, vol. 26(11), Jun. 2005, 2208-2213.

Hebeler, et al., "Study of Early Leaf Senescence in *Arabidopsis thaliana* by Quantitative Proteomics Using Reciprocal 14N/15N Labeling and Difference Gel Electrophoresis" *Molecular & Cellular Proteomics*, vol. 7, No. 1, Jan. 7, 2007; pp. 108-120.

Hoefelschweiger, B. K. et al., "Novel Type of general protein assay using a Chromogenic and Flourogenic amine-reactive probe", *Analytical Biochemistry*, vol. 344(1), Sep. 2005, 122-129.

Inouye, "'Internal standards for molecular weight determination of protein by polyacrylamide gel electrophoresis'", *J. Biological Chemistry*, vol. 246, No. 15, 08/101971; pp. 4834-4838.

Karen, M. et al., "Simultaneous trichromatic fluorescence detection of proteins on western blots using an amine-reactive dye in combination with alkaline phosphatase- and horseradish peroxidase-antibody", *Proteomics*, vol. 3, No. 7, Jul. 2003, 1215-1227.

Martin, K. et al., "Simultaneous trichromatic Fluorescence detection of proteins on western blots using an amine-reactive dye in combination with alkaline phosphatase- and horseradish peroxide-antibody conjugates", *Proteomics*, vol. 3(7), Jul. 2003, 1215-1227.

Mitrunen, et al., "'Dual-label one-step immunoassay for simutaneous measurment of free and total prostate-specific antigen concentrations and ratios in serum'", *Clin. Chem.*, vol. 41, No. 8, Dec. 31, 1995; pp. 1115-1120.

Molecular Probes, "ATTO-TAGTM CBQCA and ATTO-TAGTM FQ" *Product Information*, MP 02333, Mar. 9, 2001.

PCT/US2008/064014 "International Application Serial No. PCT/US2008/064014, Search Report & Written Opinion dated Dec. 9, 2008".

You, W. et al., "3-(4-Carboxygenzoyl) quinoline-2-carboxaldehyde, a reagent with broad dynamic range for the assay of proteins and lipoproteins in solution.", *Anal Biochem*, vol. 244, No. 2, Jan. 15, 1997, 277-282

Zhou, Ge et al., "2D differential in-gel electrophoresis for the identification of esophageal scans cell cancer-specific protein markers", *Molecular & Cellular Proteomics*, vol. 1, No. 2, Feb. 2002, pp. 117-123

\* cited by examiner

Fluorescent Image

Image after SimplyBlue™ Staining

Fluorescent Image

Image after SimplyBlue™ Staining

Fluorescent Image

Image from Safe Imager™ Transilluminator

Image after SimplyBlue™ Staining

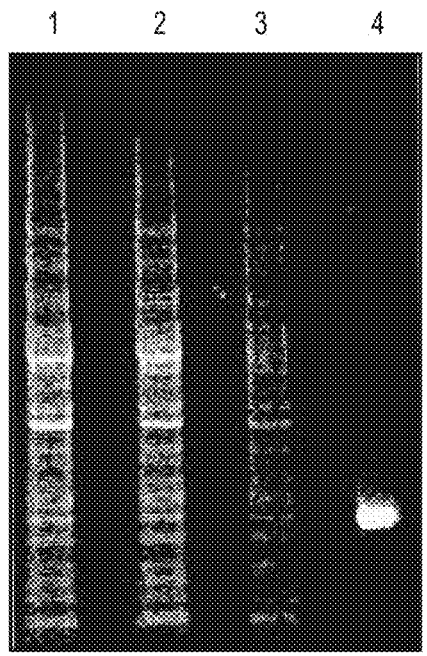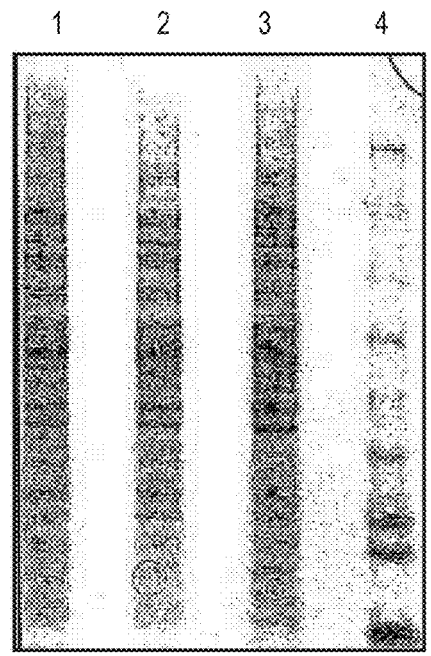
Fluorescent Image
Image after SimplyBlue™ Staining
Figure 8A
Figure 8B

SEQUENCE LISTING

```
<160> NUMBER OF SEQ ID NOS: 5

<210> SEQ ID NO 1
<211> LENGTH: 104
<212> TYPE: PRT
<213> ORGANISM: Artificial Sequence
<220> FEATURE:
<223> OTHER INFORMATION: Description of Artificial Sequence: Synthetic
      protein tag
<220> FEATURE:
<221> NAME/KEY: MOD_RES
<222> LOCATION: (3)..(102)
<223> OTHER INFORMATION: Any natural amino acid, non-natural amino acid
      or combination thereof
<220> FEATURE:
<221> NAME/KEY: MISC_FEATURE
<222> LOCATION: (3)..(102)
<223> OTHER INFORMATION: This region may encompass 2 to 100 amino acids
      wherein some positions may be absent

<400> SEQUENCE: 1

Cys Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Cys Cys
            100
```

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      protein tag

<400> SEQUENCE: 2

Cys Cys Pro Gly Cys Cys
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      protein tag

<400> SEQUENCE: 3

Ala Gly Gly Cys Cys Pro Gly Cys Cys Gly Gly Gly
1               5                   10

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      protein tag
<220> FEATURE:
<221> NAME/KEY: MOD_RES
<222> LOCATION: (3)..(102)
<223> OTHER INFORMATION: Any natural amino acid, non-natural amino acid
      or combination thereof
<220> FEATURE:
<221> NAME/KEY: MISC_FEATURE
<222> LOCATION: (3)..(102)
<223> OTHER INFORMATION: This region may encompass 2 to 100 amino acids
      wherein some positions may be absent
<220> FEATURE:
<221> NAME/KEY: MOD_RES
<222> LOCATION: (104)..(104)
<223> OTHER INFORMATION: Any natural amino acid, non-natural amino acid
      or combination thereof
<220> FEATURE:
<221> NAME/KEY: MOD_RES
<222> LOCATION: (106)..(106)
<223> OTHER INFORMATION: Any natural amino acid, non-natural amino acid
      or combination thereof

<400> SEQUENCE: 4

Cys Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Cys Xaa Cys Xaa

```
                    100             105
<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      protein tag

<400> SEQUENCE: 5

Cys Cys Gly Gly Lys Gly Asn Gly Gly Cys Gly Cys
1               5                   10
```

RAPID PROTEIN LABELING AND ANALYSIS

CROSS-REFERENCE TO RELATED APPLICATIONS

This application is a Divisional of and claims the right of priority under 35 U.S.C. § 121 to U.S. patent application Ser. No. 14/688,986, filed Apr. 16, 2015, now abandoned, which is a Continuation of and claims the right of priority under 35 U.S.C. § 120 to U.S. patent application Ser. No. 14/079,330, filed Nov. 13, 2013, now abandoned; which is a Divisional of and claims the right of priority under 35 U.S.C. § 121 to U.S. patent application Ser. No. 12/122,607, filed May 16, 2008, now U.S. Pat. No. 8,609,423 which claims the benefit of priority under 35 U.S.C. 119(e) to U.S. Provisional Application Ser. No. 60/938,973, filed May 18, 2007. All the aforementioned patents and patent applications are commonly owned with the present application and all are hereby expressly incorporated herein by reference in their entirety as though fully set forth herein to the extent that there is no inconsistency with the present disclosure.

BACKGROUND OF THE INVENTION

This invention relates to the labeling of proteins and analysis of such labeled proteins using separation techniques including electrophoresis and chromatographic methods.

SUMMARY OF THE INVENTION

The present invention provides methods and compositions for labeling, separating and analyzing proteins, particularly a specific protein of interest within a cell lysate or in a mixture of proteins. In one embodiment, the protein or proteins are labeled with an amine reactive or thiol reactive fluorescent dye. In another embodiment, the protein or proteins are labeled with an amine reactive fluorogenic reagent that becomes fluorescent upon reacting to amine groups located on the protein. Following the labeling step, the proteins within the mixture can be separated and analyzed. In a further embodiment, a first labeling compound, which can be either a fluorescent dye or a fluorogenic reagent, is used to label all of the proteins within the mixture, and a second labeling compound, a fluorogenic reagent able to bind to a tagged protein, is used to specifically label the protein of interest.

Following labeling, such labeled proteins and/or protein fragments undergo separation, detection and analysis using techniques including, but not limited to, electrophoresis techniques, chromatographic techniques, immunoblotting, mass spectroscopy, and combinations thereof. Such methods can be used to label and analyze protein samples, for example samples of acidic proteins, basic proteins, purified proteins or lysates. The methods are highly sensitive with a broad linear range of detection. Such methods are reproducible and rapid, with reduction in background staining and other non-specific artifacts, and without any visually detectable affect on electrophoretic migration, chromatographic elution or resolution of sample protein.

One embodiment provides a method for protein labeling and analysis comprising forming a first reaction mixture by admixing a mixture of proteins with a composition comprising a first buffer having a pH between pH 8 and pH 10, an amine reactive fluorogenic reagent, and either acetone cyanohydrin, a nitrile or an alkali cyanide. This reaction mixture is incubated for a first incubation time at a first temperature and then admixed with a second buffer to form a second reaction mixture. The second buffer has a pH between pH 6 and pH 9 and optionally has a buffer capacity greater than the first buffer so that that pH of the second reaction mixture is between pH 6 and pH 9. The second reaction mixture is then incubated for a second incubation time, which may be the same or different than the first incubation time, at a second temperature, which also may be the same or different than the first temperature. The fluorescently labeled proteins are then separating and visualized. The first reaction mixture optionally also comprises an anionic surfactant, a sugar or sugar alcohol, or an alkylating agent. The second reaction mixture optionally also comprises one or more reducing agents.

In a further embodiment, the mixture of proteins additionally comprises a protein of interest that is tagged and the second buffer further comprises a tag binding fluorogenic reagent that binds to a tag on the tagged protein. The amine reactive fluorogenic reagent has a first emission wavelength and the tag binding fluorogenic reagent has a second emission wavelength. The emission wavelengths are different allowing the wavelengths to be compared and analyzed.

Another embodiment provides a method for protein labeling and analysis comprising forming a first reaction mixture by admixing a mixture of proteins with a first composition comprising a first buffer having a pH between pH 8 and pH 10, and either an amine reactive fluorescent dye or a tag binding fluorogenic reagent. This reaction mixture is incubated for a first incubation time at a first temperature and then admixed with a second composition to form a second reaction mixture. The second composition comprises a second buffer having a pH between pH 6 and pH 10, at least one reducing agent, and either an amine reactive fluorescent dye or a tag binding fluorogenic reagent. If the first composition comprises an amine reactive fluorescent dye, then the second composition comprises a tag binding fluorogenic reagent, and if the first composition comprises a tag binding fluorogenic reagent, then the second composition comprises an amine reactive fluorescent dye. The second reaction mixture is then incubated for a second incubation time, which may be the same or different than the first incubation time, at a second temperature, which also may be the same or different than the first temperature. The fluorescently labeled proteins are then separating and visualized. The amine reactive fluorescent dye has a first emission wavelength and the tag binding fluorogenic reagent has a second emission wavelength. The emission wavelengths are different allowing the wavelengths to be compared and analyzed.

Other embodiments include precipitating a sample containing a mixture of proteins followed by reconstituting the sample in the labeling solutions described herein. This precipitation step may remove potentially interfering or unwanted chemical components present in the initial sample. Alternatively, or in addition to this precipitation step, the proteins or mixture of proteins may be alkylated prior to labeling in order to eliminate the negative impact of any reducing agents on labeling.

Another embodiment provides kits for fluorescently labeling proteins comprising a) a first composition having a buffer with a pH in the range from pH 8 to pH 10, either an amine reactive fluorogenic reagent or an amine reactive fluorescent dye, a sugar or sugar alcohol, and an anionic surfactant; and b) a second composition comprising a second buffer having a pH in the range from pH 6 to pH 10. In a further embodiment where the first composition comprises an amine reactive fluorogenic reagent, the first composition also comprises either acetone cyanohydrin, a nitrile, or an alkali cyanide, preferably a nitrile such as mandelonitrile. In a further embodiment, the first composition comprises an amine reactive fluorescent dye. In a further embodiment, the second composition further comprises a tag binding fluorogenic reagent that binds to at least four cysteine moieties, and at least one reducing agent, wherein the amine reactive fluorogenic reagent or fluorescent dye has a first emission wavelength and the tag binding fluorogenic dye has a second emission wavelength, and the first emission wavelength and the second emission wavelength are different.

In illustrative embodiments, the methods and compositions described herein for protein analysis using slab gel electrophoresis allows for rapid, real time analysis without the need for gel handling, or opening an electrophoresis cassette to stain and image the gel.

BRIEF DESCRIPTION OF THE FIGURES

FIG. 5A is a gel image of proteins and protein standards labeled using the methods described herein, while FIG. 5B is an image of the gel shown in FIG. 5A after staining with SimplyBlue™ SafeStain.

FIG. 6A is a gel image of proteins labeled using the methods described herein, while FIG. 6B is an image of the gel shown in FIG. 6A after staining with SimplyBlue™ SafeStain.

FIG. 7A is a gel image of BSA labeled using the methods described herein, using Fujifilm's LAS-1000 with a 477 nm EPI light source, 520-640 nm band pass filter and an exposure time of 60 seconds. FIG. 7B is an image obtained using a Safe Imager™ transilluminator (~470 nm light source) and a Kodak DC290 digital camera (2.1 MP) with an exposure time of 8 seconds. FIG. 7C is an image of the gel shown in FIG. 7A and FIG. 7B but after total protein staining using SimplyBlue™ SafeStain.

FIG. 8A and FIG. 8B illustrate the labeling of *E. coli* lysate using the methods described herein at three different labeling times. FIG. 8A is a fluorescence gel image of *E. coli* lysate (reduced) obtained using Fujifilm's LAS-1000 with a 477 nm EPI light source, a 520-640 nm band pass filter and an exposure time of 30 seconds. FIG. 8B is an image of the gel shown in FIG. 8A after staining with SimplyBlue™ SafeStain.

FIG. 9A are gel images (fluorescence and after SimplyBlue™ staining) of labeled lysozyme (reduced) in lane 1 and SeeBlue® Plus2 Prestained Standard (Invitrogen, Carlsbad) in lane 2, while FIG. 9B are gel images (fluorescence and after Simply-Blue™ staining) of SeeBlue® Plus2 Prestained Standard (Invitrogen, Carlsbad) in lane 1 and rat liver lysate in lane 3 with lane 2 empty. Fluorescent images were obtained using Fujifilm's LAS-1000 with a 477 nm EPI light source, a 520-640 nm band pass filter and an exposure time of 30 seconds.

FIG. 10A is a gel image after staining with SimplyBlue™ Safe Stain, while FIG. 10B is a gel image of h-IgG, myoglobin and BSA labeled using the methods described herein. Fluorescent images were obtained using Fujifilm's LAS-1000 with a 477 nm EPI light source, a 520-640 nm band pass filter and an exposure time of 1 minute.

Figure 1:
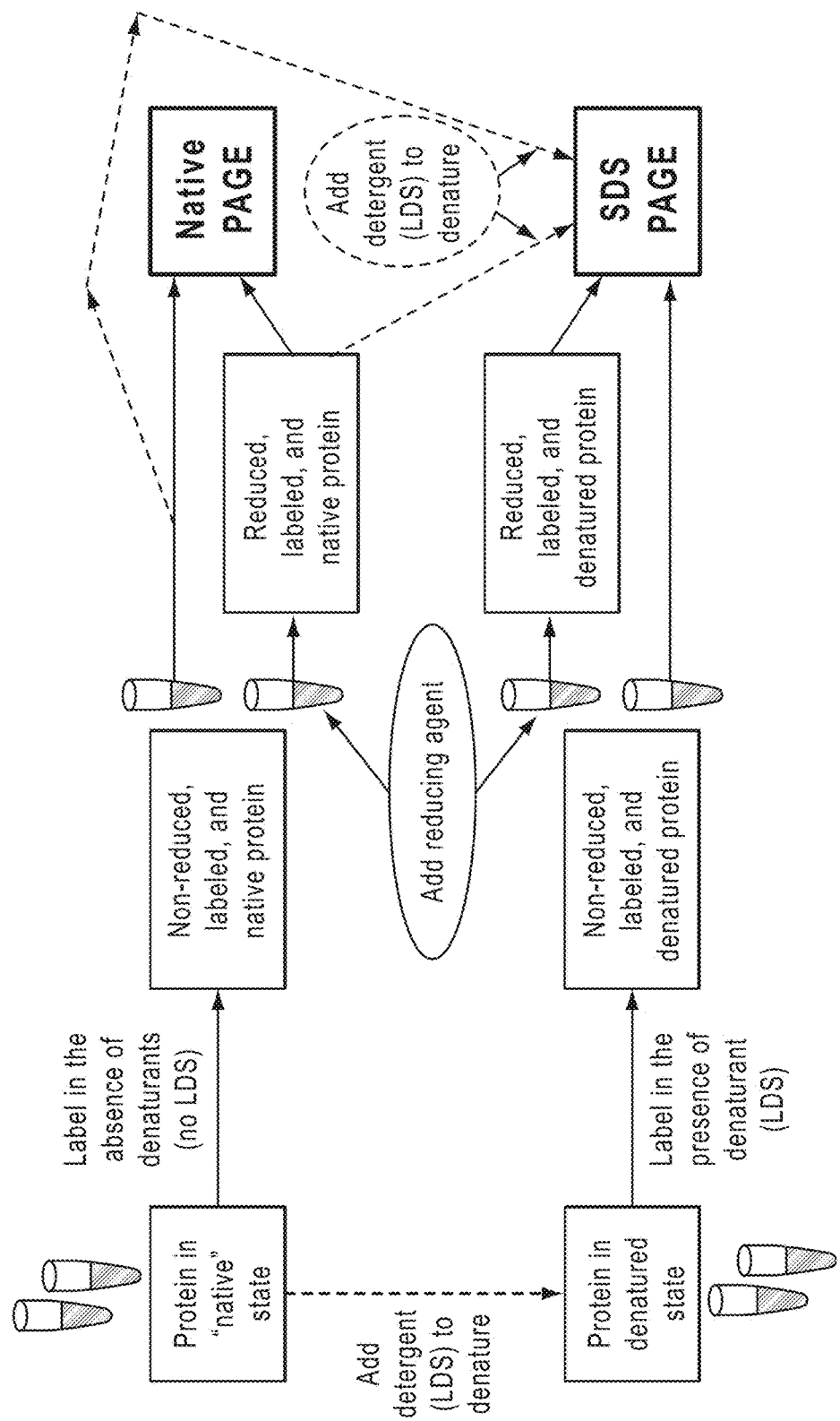
FIG. 1 is a schematic illustrating certain embodiments of the methods for total protein labeling and analysis described herein using amine reactive fluorogenic reagents.

A better understanding of the features and advantages of the present methods and compositions may be obtained by reference to the following detailed description that sets forth illustrative embodiments, in which the principles of our methods, compositions, devices and apparatuses are utilized, and the accompanying drawings.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein are well known and commonly employed in the art. Terms of orientation such as "up" and "down", "top" and "bottom", "above" and "underneath" or "upper" or "lower" and the like refer to orientation of parts during use of a device. Where a term is provided in the singular, the inventors also contemplate the plural of that term. Where there are discrepancies in terms and definitions used in references that are incorporated by reference, the terms used in this application shall have the definitions given herein. As employed throughout the disclosure, the following terms, unless otherwise indicated, shall be understood to have the following meanings.

The term "ambient temperature" as used herein, refers to the temperature in the range from about 20° C. to about 25° C. The term "room temperature" as used herein, refers to the temperature in the range from about 20° C. to about 25° C.

The term "protein" or "proteins", as used herein, include full length proteins, protein fragments, proteins in their native state or denatured proteins. Mixture of proteins can be a mixture of full length proteins, a mixture of protein fragments, or a mixture of full length proteins and protein fragments. Proteins can be acidic or basic, and can be purified as a mixture from cell lysates.

The term "peptide", as used herein refers to a compound that includes two or more amino acids. The amino acids link together to form a peptide chain. There are 20 different naturally occurring amino acids involved in the biological production of peptides, and any number of them can be linked in any order to form a peptide chain. The naturally occurring amino acids employed in the biological production of peptides all have the L-configuration. Synthetic peptides can be prepared employing conventional synthetic methods, using L-amino acids, D-amino acids or various combinations of amino acids of the two different configurations. Some peptide chains contain only a few amino acid units. Short peptide chains, e.g., having less than ten amino acid units, are sometimes referred to as "oligopeptides", where the prefix "oligo" signifies "few." Other peptide chains contain a large number of amino acid units, e.g., up to 100 or more, and are referred to a "polypeptides", where the prefix "poly" signifies "many." Still other peptide chains, containing a fixed number of amino acid units are referred to using a prefix that signifies the fixed number of units in the chain, e.g., an octapeptide, where the prefix "octa" signifies eight. By convention, a "polypeptide" can be considered as any peptide chain containing three or more amino acids, whereas an "oligopeptide" is usually considered as a particular type of "short" polypeptide chain. Thus, as used herein, it is understood that any reference to a "polypeptide" also includes an oligopeptide. Further, any reference to a "peptide" includes polypeptides, oligopeptides. Each different arrangement of amino acids forms a different polypeptide chain. In certain non-limiting examples, the polypeptide includes between 40 and 4000 amino acids, between 50 and 3000 amino acids, or between 75 and 2000 amino acids.

The term "fluorophore" of "fluorescent moiety", as used herein, refers to a compound, chemical group, or composition that is inherently fluorescent. Fluorophores may contain substituents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a furan, a benzazole, a borapolyazaindacene and xanthenes including fluoroscein, rhodamine and rhodol as well as other fluorophores described in RICHARD P. HAUGLAND, MOLECULAR PROBES HANDBOOK OF FLUORESCENT PROBES AND RESEARCH CHEMICALS ($9^{th}$ edition, CD-ROM, September 2002).

The term "fluorogenic" as used herein refers to refers to a compound, chemical group, or composition that becomes fluorescent or demonstrates a change in fluorescence upon protonation, or binding to a biological compound or metal ion, or metabolism by an enzyme. Fluorogenic compounds, groups or compositions also become fluorescent upon covalently linking to a reactive group.

The term "homogeneity of labeling", as used herein, refers to the degree of labeling of available reactive sites on the protein or protein fragments.

The term "reactive group" as used herein refers to a group that is capable of reacting with another chemical group to form a covalent bond, i.e. is covalently reactive under suitable reaction conditions, and generally represents a point of attachment for another substance. Reactive groups generally include nucleophiles, electrophiles and photoactivatable groups. Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds., *Organic Functional Group Preparations,* Academic Press, San Diego, 1989).

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

The term "kit" as used herein refers to a packaged set of related components, typically one or more compounds or compositions.

The term "label," as used herein, refers to a chemical moiety or protein that is directly or indirectly detectable (e.g. due to its spectral properties, conformation or activity) when attached to a target or compound and used in the present methods, including reporter molecules, solid supports and carrier molecules. As used herein, label collectively refers to a reporter molecule, solid support or carrier molecule. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidase (HRP) to bind to the tag, and then use a colorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS ($10^{th}$ edition, CD-ROM, September 2005), supra.

As used herein, the term "rapid labeling" refers to fluorescently labeling proteins using methods that can be completed in less than 2 hours, more preferably in less than 1 hour. In certain embodiments the method of protein labeling described herein is completed in less than 30 minutes, preferably in less than 20 minutes, even more preferably in less than 10 minutes. In certain embodiments the method of protein labeling described herein is completed in less than 1 to 5 minutes.

In general, for ease of understanding the present invention, the total protein labels and expression tag labels will first be described in detail, followed by the many and varied methods in which theses labels find uses, which is followed by exemplified methods of use.

Methods for Labeling Proteins

Disclosed herein are methods and compositions for protein analysis wherein a mixture of proteins, comprising a protein of interest, is contacted, or otherwise admixed, with an amine reactive fluorescent dye or a thiol reactive fluorescent dye, thereby fluorescently labeling the proteins and allowing for a measure of the total protein present. In addition, this mixture is contacted, or otherwise admixed, with a second fluorescent moiety which binds to a tag attached to the protein of interest, thereby obtaining a measure of the protein of interest. The second fluorescent moiety is a fluorescent dye that binds to a tag attached to the protein of interest, or a fluorogenic reagent that becomes fluorescent after binding to a tag attached to the protein of interest. Such labeled proteins are then separated using techniques such as electrophoretic methods, chromatographic methods, or combinations thereof. The two fluorescent moieties have different emission properties, thereby allowing for dual fluorescence measurements. The method further includes comparing the two fluorescence measurements to obtain a measure of the protein of interest relative to the other proteins present in the mixture. In certain embodiments, such methods are used for protein expression analysis, and comparison of the two fluorescence measurements results in a measure of the level of expression of the protein of interest.

Also disclosed herein are methods for protein analysis wherein a mixture of proteins comprising a protein of interest is contacted, or otherwise admixed, with an amine reactive fluorogenic reagent that becomes fluorescent after reacting with amine groups or thiol groups on the proteins, thereby fluorescently labeling the proteins and allowing for a measure of the total protein present. In addition, this mixture is contacted, or otherwise admixed, with a second fluorescent moiety which binds to a tag attached to the protein of interest, thereby obtaining a measure of the protein of interest. The second fluorescent moiety is a fluorescent dye that binds to a tag attached to the protein of interest, or a fluorogenic reagent that becomes fluorescent after binding to a tag attached to the protein of interest. Such labeled proteins are then separated using techniques such as electrophoretic methods, chromatographic methods, or combinations thereof. The two fluorescent moieties have different emission properties, thereby allowing for dual fluorescence measurements. The method further includes comparing the two fluorescence measurements to obtain a measure of the protein of interest relative to the other proteins present in the mixture. In certain embodiments, such methods are used for protein expression analysis, and comparison of the two fluorescence measurements results in a measure of the level of expression of the protein of interest.

The two fluorescent moieties in such methods can be excited with the same excitation wavelength originating from the same excitation source, or the two fluorescent moieties can be excited with different excitation wavelength originating from different excitation sources. In addition, the two fluorescent moieties can be excited with the same excitation wavelength originating from different excitation sources, or the two fluorescent moieties can be excited with different excitation wavelength originating from one excitation source.

Further disclosed herein are methods for protein analysis wherein a protein, protein fragments or mixture of proteins is contacted, or otherwise admixed, with an amine reactive fluorogenic reagent that becomes fluorescent after reacting with amine groups on the protein, protein fragments or mixture of proteins. Such labeled proteins are then separated using electrophoretic methods, chromatographic methods, or combinations thereof. The methods for fluorescently labeling protein used in such protein analysis methods allow for efficient labeling of proteins using fluorogenic reagents while also reducing proteins for analysis under denaturing conditions. Technique used for analysis under denaturing conditions include, but are not limited to, SDS-PAGE analysis.

Other embodiments include precipitating a sample containing a mixture of proteins, which may contain a protein of interest, followed by reconstituting the sample in the labeling solutions as described herein. The additional precipitation step may remove potentially interfering or unwanted chemical components present in the initial sample. Alternatively, or in addition to this precipitation step, the proteins or mixture of proteins may be alkylated, using alkylating agents as known in the art such as dimethyl acrylamide (DMA), prior to labeling in order to eliminate the negative impact of any reducing agents on labeling.

The proteins, protein fragments or mixture of proteins labeled using the methods described herein have improved labeling efficiencies, wherein the homogeneity of labeling can be from 70% to 100%. In certain embodiments the homogeneity of labeling is from 75% to 100%. In other embodiments the homogeneity of labeling is from 80% to 100%. In other embodiments the homogeneity of labeling is from 85% to 100%. In other embodiments the homogeneity of labeling is from 90% to 100%. In certain embodiments the homogeneity of labeling is from 95% to 100%. In other embodiments the homogeneity of labeling is greater than 98%. The homogeneity of labeling is characterized by the presence of minimal band spreading when such labeled proteins are separated using slab gel electrophoresis relative to the band widths obtained when the identical proteins are unlabeled. In addition, the homogeneity of labeling is characterized by minimized band broadening when such labeled proteins are separated using capillary electrophoresis relative to the band broadening obtained when the identical proteins are unlabeled. In addition, the improved homogeneity of labeling is characterized by minimal effect on protein migration after the protein has been labeled, relative to the migration obtained when the identical proteins are unlabeled.

In certain embodiments of the labeling methods described herein, there is no visually observable difference in band width or band migration when labeled proteins are compared to un-labeled proteins. In certain embodiments the difference in band width or band migration of labeled proteins is +/−20% when the band on an image of the gel is digitized and measured digitally and compared to that obtained for un-labeled proteins. In certain embodiments the difference in band width or band migration of labeled proteins is +/−10% when the band on an image of the gel is digitized and measured digitally and compared to that obtained for un-labeled proteins. In certain embodiments the difference in band width or band migration of labeled proteins is +/−5% when the band on an image of the gel is digitized and measured digitally and compared to that obtained for un-labeled proteins. In such embodiments, the band thickness and apparent molecular weight of the separated protein is unaffected by the presence of the fluorogenic dye.

In the labeling and analysis methods described herein the proteins or mixtures of proteins are labeled prior to separation thereby removing the need for any post labeling or staining processes. Consequently, such methods allow for rapid analysis of protein expression and total protein present in a sample. For example, the labeling methods described herein are compatible with immunoblotting (i.e., Western blotting/transfers) and can also lead to a significant (ten-fold) increase in sensitivity. Other applications following labeling also may include mass spectroscopy. In addition, the methods described herein permit the in-gel detection of proteins, protein fragments or mixtures of proteins without gel drying, without blotting, and without expensive and complex equipment.

Protein Analysis Using Amine Reactive Fluorogenic Reagents for Total Protein Labeling In one aspect of the methods for total protein analysis using amine reactive fluorogenic reagents, the protein, protein fragment or the mixture of proteins are first admixed with a composition that includes a first buffer having a pH between about pH 8 and about pH 10, an amine reactive fluorogenic reagent, an alkali cyanide and optionally an anionic surfactant. Optionally, the alkali cyanide can be replaced with a less toxic alternative such as acetone cyanohydrin or a nitrile such as mandelonitrile. The first buffer used in this initial step does not include buffer compounds or additives that have primary or secondary amine moieties. However, the methods described herein can tolerate low levels of amines that may be already present in the protein sample. The first reaction mixture is then incubated for a first incubation time at a first incubation temperature before admixing a second buffer, with a buffer capacity greater than the first buffer, thereby maintaining the pH between about pH 6 and about pH 9. A reducing agent can optionally be added after addition of the second buffer and the resulting mixture is incubated for a second incubation time at a second incubation temperature. The protein, protein fragment or the mixture of proteins become fluorescently labeled and can be separated using electrophoretic methods, chromatographic methods, or combinations thereof.

The buffer capacity of the second buffer can be in the range between 1× to 20× the buffer capacity of the first buffer. In certain embodiments, the buffer capacity of the second buffer is at least 2×, at least 3×, at least 4×, at least 5×, at least 6×, at least 7×, at least 8×, at least 9×, at least 10×, at least 11×, at least 12×, at least 13×, at least 14×, at least 15×, at least 16×, at least 17×, at least 1×, at least 19× or at least 20× the buffer capacity of the first buffer. In certain embodiments, the buffer capacity of the second buffer is between 2× and 20×, between 3× and 20×, between 4× and 20×, between 5× and 20×, between 6× and 20×, between 7× and 20×, between 8× and 20×, between 9× and 20×, between 10× and 20×, between 15× and 20×, and between 10× and 25× the buffer capacity of the first buffer.

FIG. 1 illustrates a schematic of methods for total protein labeling and analysis using amine reactive fluorogenic reagents as described herein. Such methods include labeling proteins in their "native" state without the presence of a denaturant, or denatured proteins are labeled using such methods described herein. In addition, the labeled native proteins or labeled denatured proteins can optionally be reduced prior to separation using Native PAGE or SDS PAGE electrophoretic methods, respectively.

Figure 2:
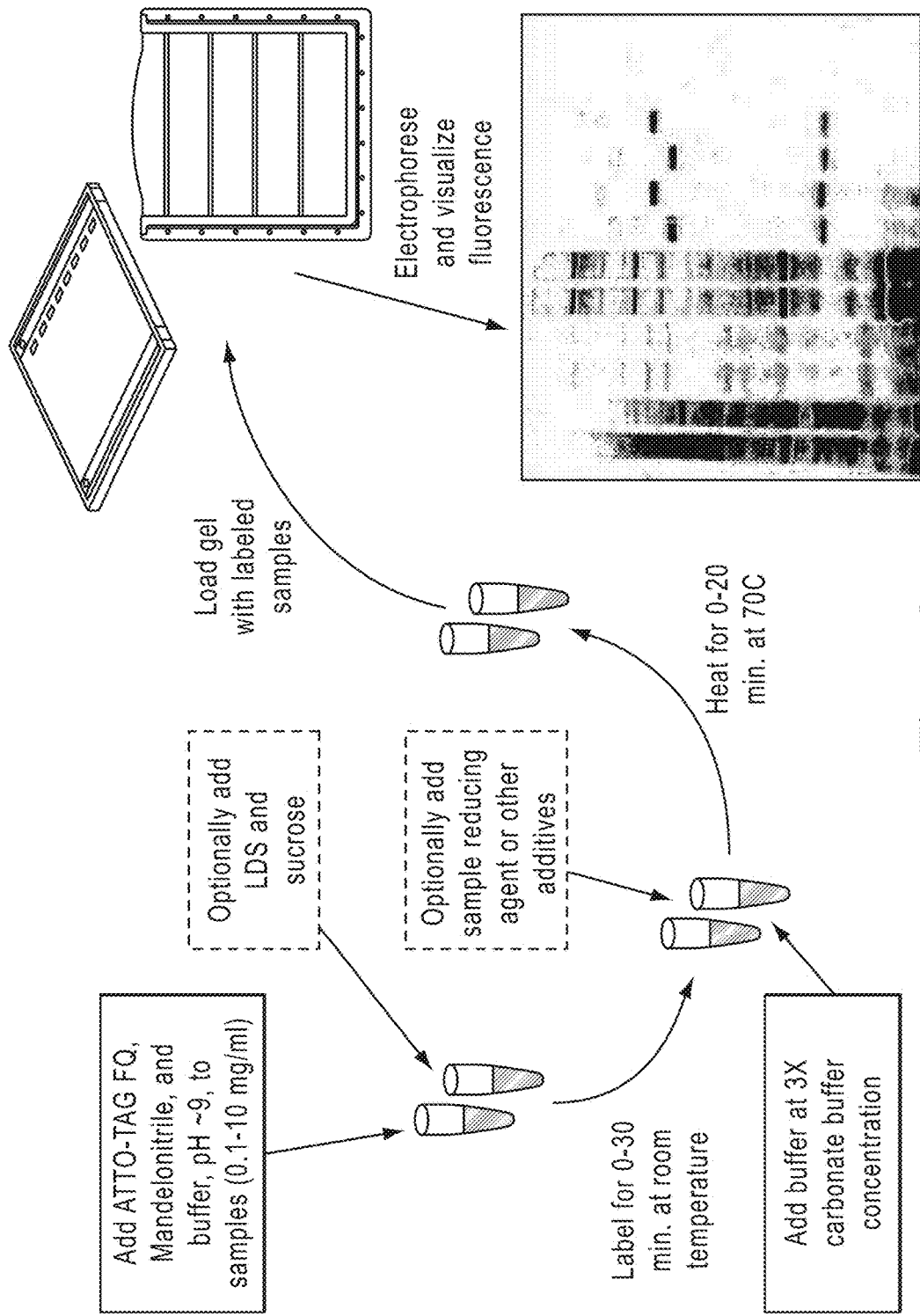
FIG. 2 is a schematic illustration of an embodiment of the methods for total protein labeling and analysis described herein using amine reactive fluorogenic reagents.

FIG. 2 illustrates a schematic of an embodiment of the protein labeling and analysis methods that use amine reactive fluorogenic reagents. In such an embodiment a mixture of ATTO-TAG FQ™ (Invitrogen Corp., Carlsbad), mandelonitrile in carbonate buffer (pH ~9) is added to a protein sample (concentration range of 0.1-10 mg/mL). LDS and sucrose are optionally added to this mixture. The reaction mixture is incubated at room temperature (RT) for 0-30 minutes, and then Bis-Tris buffer is added to lower the pH of the reaction mixture to about pH 6.5. In this embodiment the Bis-Tris buffer has a buffer capacity 3× that of the carbonate buffer. Protein reducing agent(s) are optionally added and the reaction mixture is then heated at 70° C. for 0-20 minutes. This mixture is then loaded into sample wells in an electrophoresis gel contained in an electrophoresis cassette, and the labeled proteins are then separated and visualized using fluorescence imaging detection.

Such labeling methods can be used to label proteins, protein ladders and/or protein standards. For example, in one embodiment bovine serum albumin (BSA) and lysozyme, and the BenchMark™ Protein Ladder (Invitrogen, Carlsbad) and Mark12™ Unstained Standard (Invitrogen, Carlsbad) standards/ladders were labeled with amine reactive fluorogenic reagents. However, any protein, ladder or standard can be labeled using such methods.

Figure 9A:
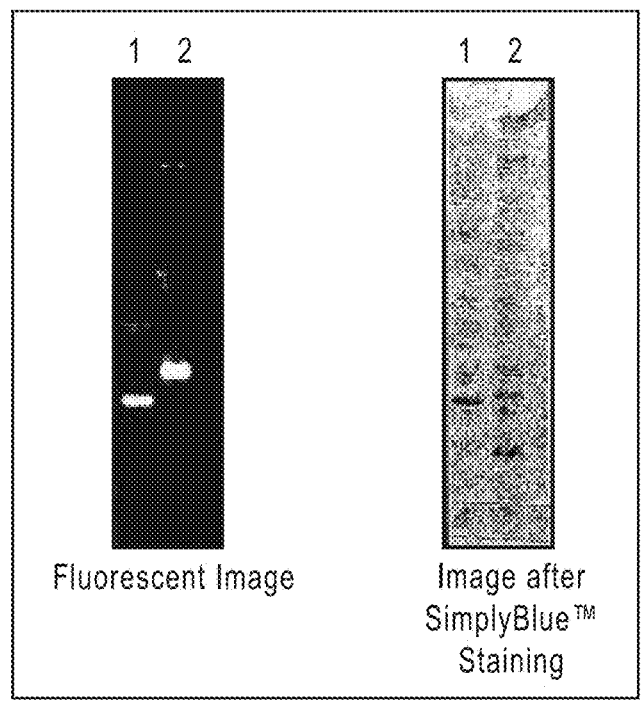
FIG. 9A and FIG. 9B compare the labeling of different proteins using the methods described herein.
Figure 9B:
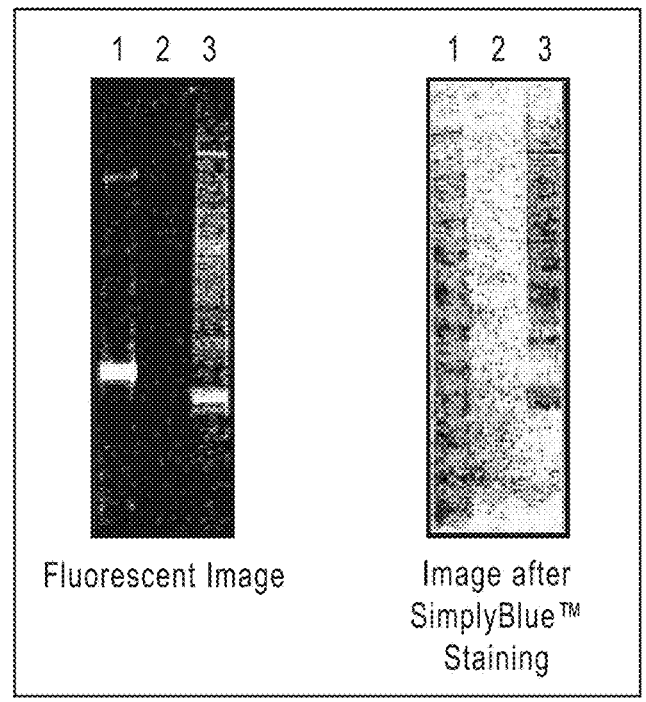

Such labeling methods can be used to label cell lysate. FIG. 8A and FIG. 8B show the gel images obtained after labeling *E. coli* lysate at various times with amine fluorogenic reagents using the methods described herein. Other lysates, including but not limited to rat liver, HeLa cell, and other mammalian cell lysates, can be labeled using such methods. FIG. 9A and FIG. 9B show the gel images obtained after labeling rat liver lysate.

Figure 10A:
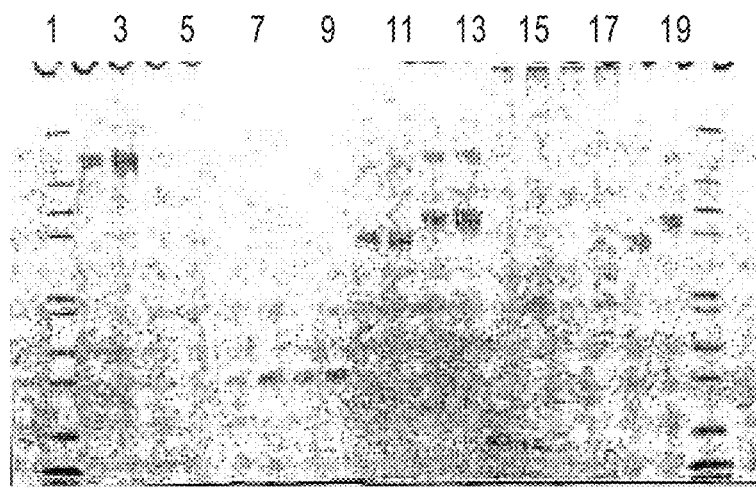
FIG. 10A and FIG. 10B illustrate native labeling of h-IgG, myoglobin and BSA.
Figure 10B:
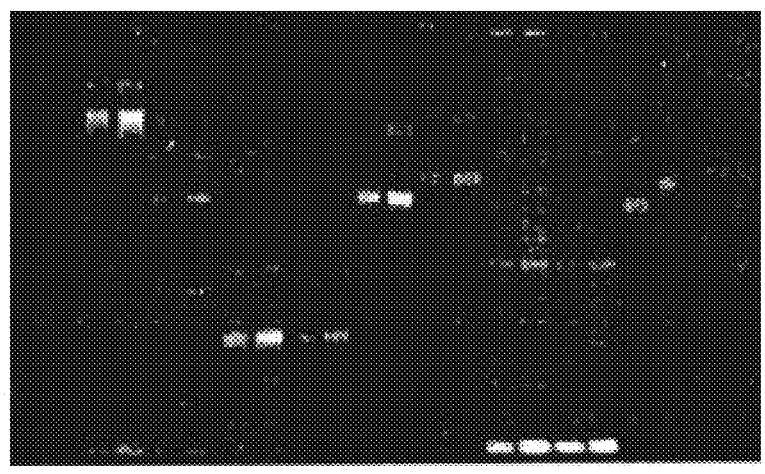
Figure 11A:
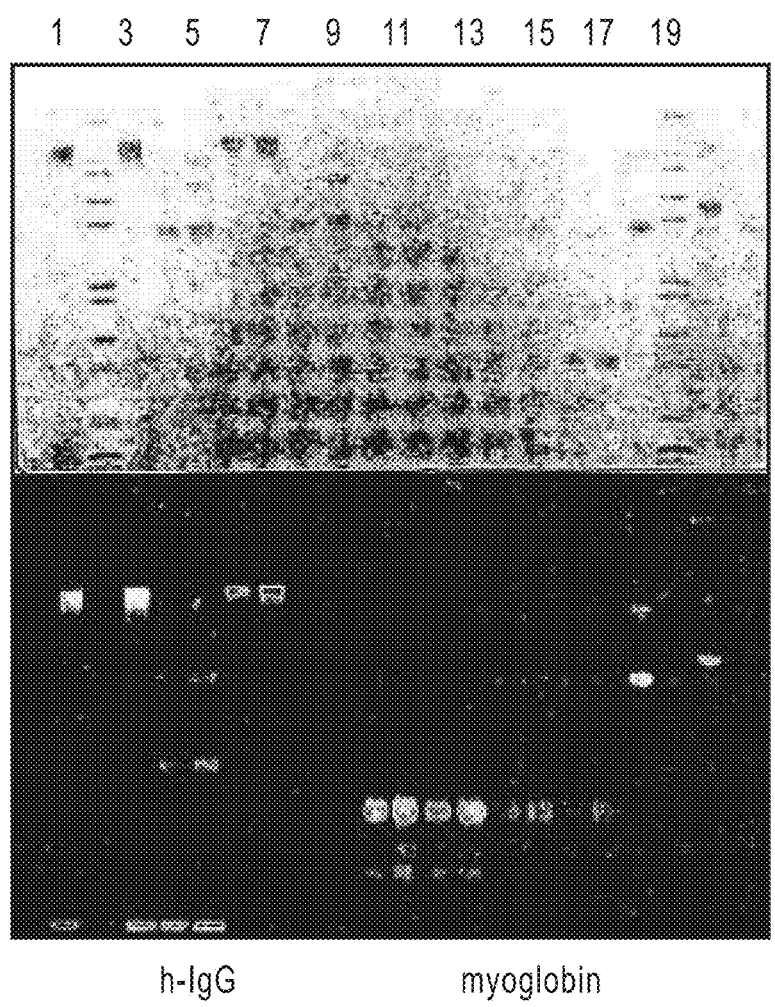
FIG. 11A and FIG. 11B illustrate the fluorescence after labeling of h-IgG, myoglobin, BSA, and *E. coli* lysate under denaturing conditions with LDS and sucrose present in the labeling reaction. The upper gel images were obtained after staining with SimplyBlue™ Safe Stain, while the lower are fluorescent gel images of h-IgG, myoglobin, BSA, and *E. coli* lysate labeled using the methods described herein. Fluorescent images were obtained using Fujifilm's LAS-1000 with a 477 nm EPI light source, a 520-640 nm band pass filter and an exposure time of 1 minute.
Figure 11B:
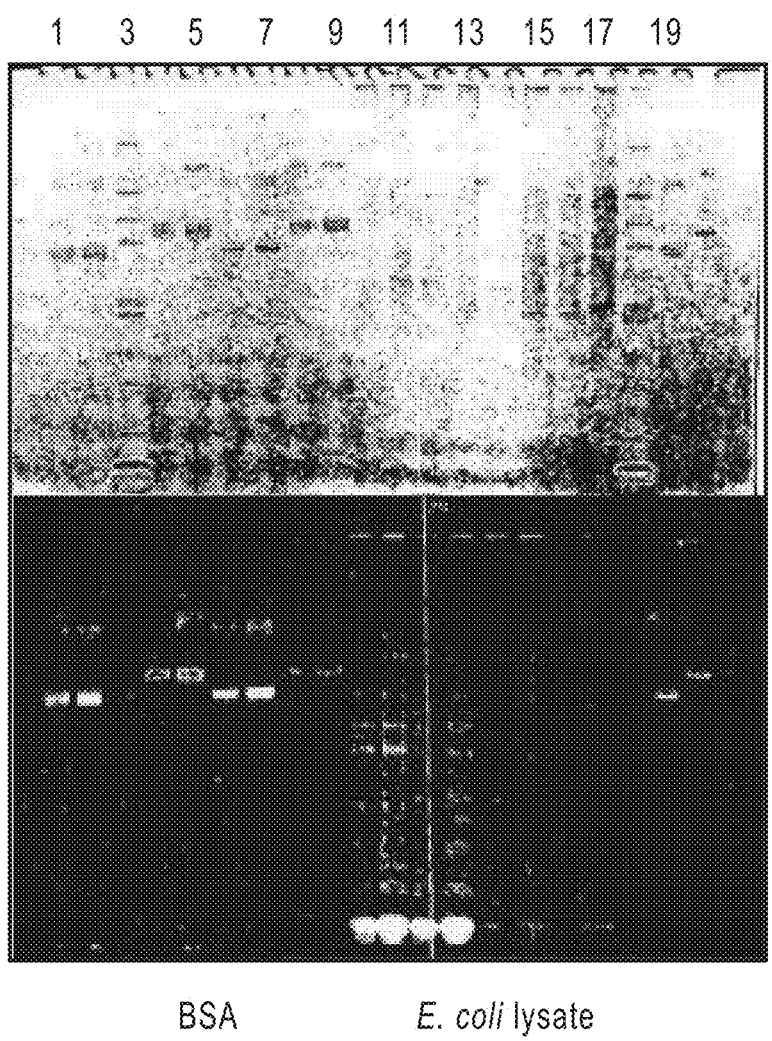

Such labeling methods can be used to label cell proteins in their "native" state. FIG. 10A and FIG. 10B show the gel images obtained after labeling bovine serum albumin (BSA), myoglobin, h-IgG and *E. coli* lysate in the absence of a denaturing agent, such as SDS or LDS. Alternatively, such labeling methods can be used to label cell proteins in their "denatured" state. FIG. 11A and FIG. 11B show the gel images obtained after labeling bovine serum albumin (BSA), myoglobin, h-IgG and *E. coli* lysate in the presence of a denaturing agent, such as SDS or LDS.

Figure 12:
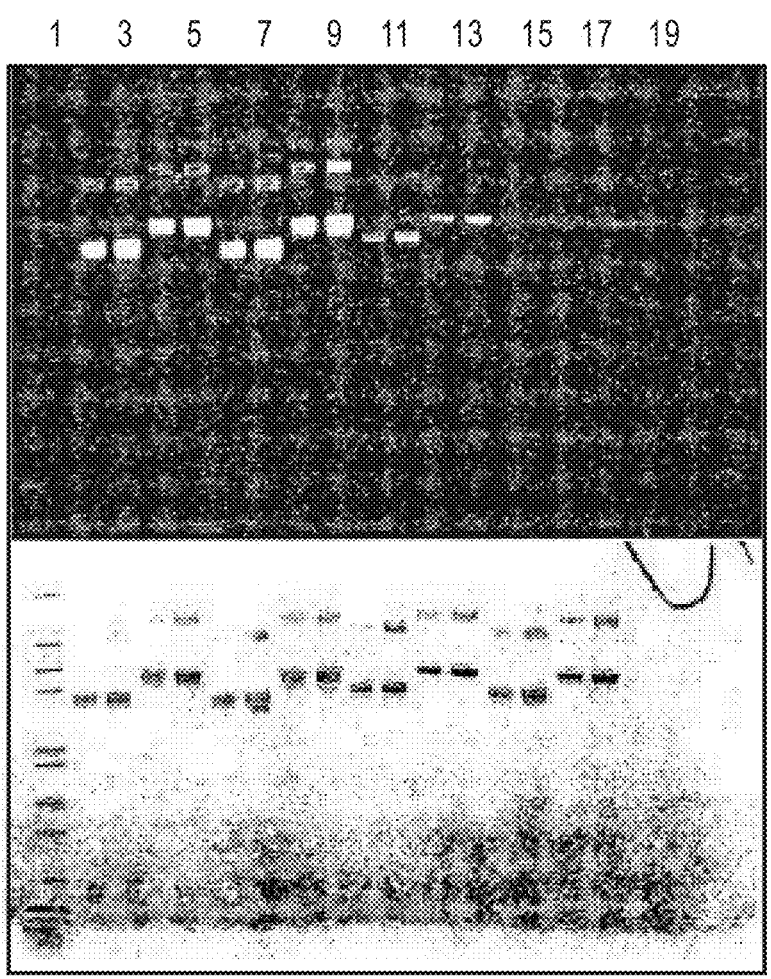
FIG. 12 illustrates the band sharpness and signal intensity as a function of reactant concentrations and labeling time for labeling BSA using the methods described herein. The upper gel image is a fluorescent image from BSA labeled as described herein, while the lower image is the gel after staining with SimplyBlue™ Safe Stain. The fluorescence image was obtained using Fujifilm's LAS-1000 with a 477 nm EPI light source, a 520-640 nm band pass filter and an exposure time of 1 minute.
Figure 13A:
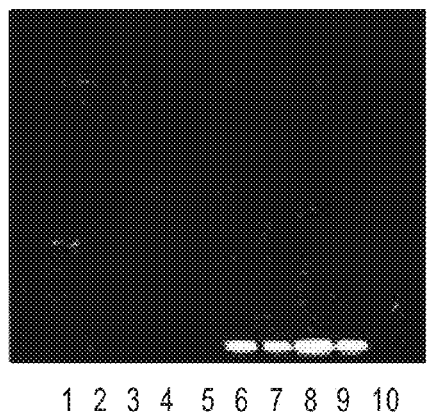
FIG. 13 illustrates the effects of fluorescence over-saturation, labeling at high temperature, and exposure of labeled protein to low pH on labeling of proteins at elevated temperatures.
Figure 13B:
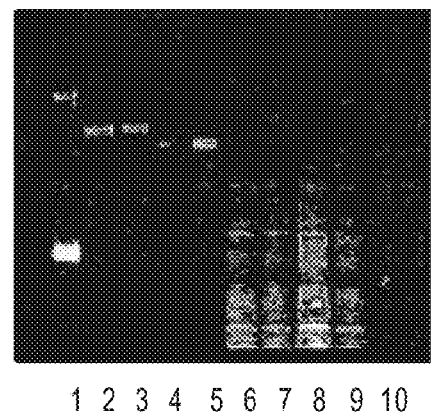
Figure 13C:
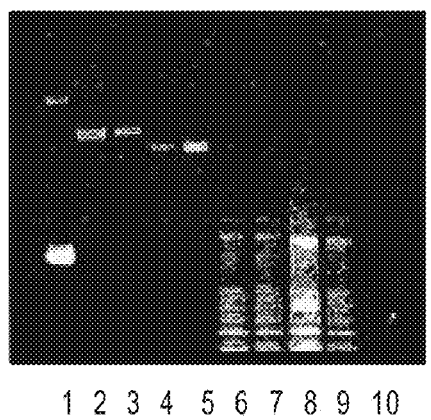
Figure 13D:
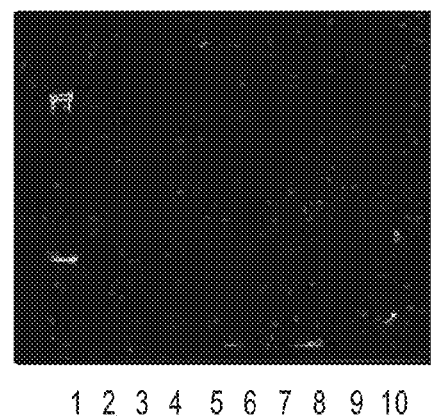

It was observed that the protein labeling methods using amine reactive fluorogenic reagents described herein result in sharp bands as observed in gel electrophoreses. The effect of band sharpness was shown by labeling bovine serum albumin (BSA) with amine reactive fluorogenic reagents using the methods described herein using various reactant concentrations and labeling time (FIG. 12). This is in contrast to that observed using standard labeling methods that use only a single labeling buffer with a pH from 8-10.

The labeling of proteins with amine reactive fluorogenic reagents using the methods described herein may be used for protein digestion as analysis as shown in FIG. 13, wherein labeled BSA is degrade and the resulting digestion mixture is analyzed.

Protein Expression Analysis Using Fluorogenic Tag Binding Reagents with Amine Reactive Fluorescent Dyes In one aspect of the methods using tag binding fluorogenic reagents/dyes in combination with amine reactive fluorescent dyes for protein analysis, including protein expression analysis, a first reaction mixture is formed by admixing a mixture of proteins containing a tagged protein of interest with a composition that includes a first buffer having a pH between about pH 8 and about pH 10 and an amine reactive fluorescent dye. The first buffer used in this initial step does not include buffer compounds or additives that have primary or secondary amine moieties. However, the methods described herein can tolerate low levels of amines that may be already present in the protein sample. This first reaction mixture is then incubated for a first incubation time at a first incubation temperature, resulting in the labeling of the mixture of proteins, including the tagged protein of interest, with the amine reactive fluorescent dye and thereby obtaining a measure of the total proteins present in the protein mixture. The first reaction mixture is further admixed with a second buffer having a pH between about pH 7 and about pH 10, a fluorogenic reagent/dye that binds to a tag attached to the protein of interest, at least one reducing agent, and an optional anionic surfactant, thereby forming a second reaction mixture. The second reaction mixture is then incubated for a second incubation time at a second incubation temperature, whereby the fluorogenic reagent/dye becomes fluorescent upon binding to the tag on the protein of interest. This labeling method results in the mixture of proteins, including the tagged protein of interest, being labeled with one fluorescent moiety (from the amine fluorescent dye), and the protein of interest also being labeled with a second fluorescent moiety (from the fluorogenic reagent).

Consequently, a population of proteins in the protein mixture becomes fluorescently labeled with both fluorescent moieties, while the remaining proteins in the mixture are labeled with only the amine reactive fluorescent dye. In addition to labeling the protein mixture, such protein analysis methods further includes separating the fluorescently labeled protein mixture using electrophoretic methods, chromatographic methods, or combinations thereof, and visualizing/measuring the fluorescence of the separated proteins using fluorescence imaging techniques. The amine reactive fluorescent dye has different spectral emission properties than the fluorescent moiety bound to the tag on the protein of interest, therefore the resulting fluorescence measurements are compared to obtain a measure of the protein of interest relative to the total proteins present in the protein mixture. The amine reactive fluorescent dye and the fluorogenic reagent that binds to a tag can be excited by the same excitation source or they can be excited by different excitation sources. In certain embodiments of such protein analysis methods, the first buffer includes at least one reducing agent and the second buffer does not contain a reducing agent, while in other embodiments both the first buffer and second buffer include at least one reducing agent. In certain embodiments, such protein analysis methods are used for protein expression analysis, and comparison of the fluorescence measurements of the two fluorescent moieties yields a measure of the level of protein expression of a protein of interest.

Figure 3:
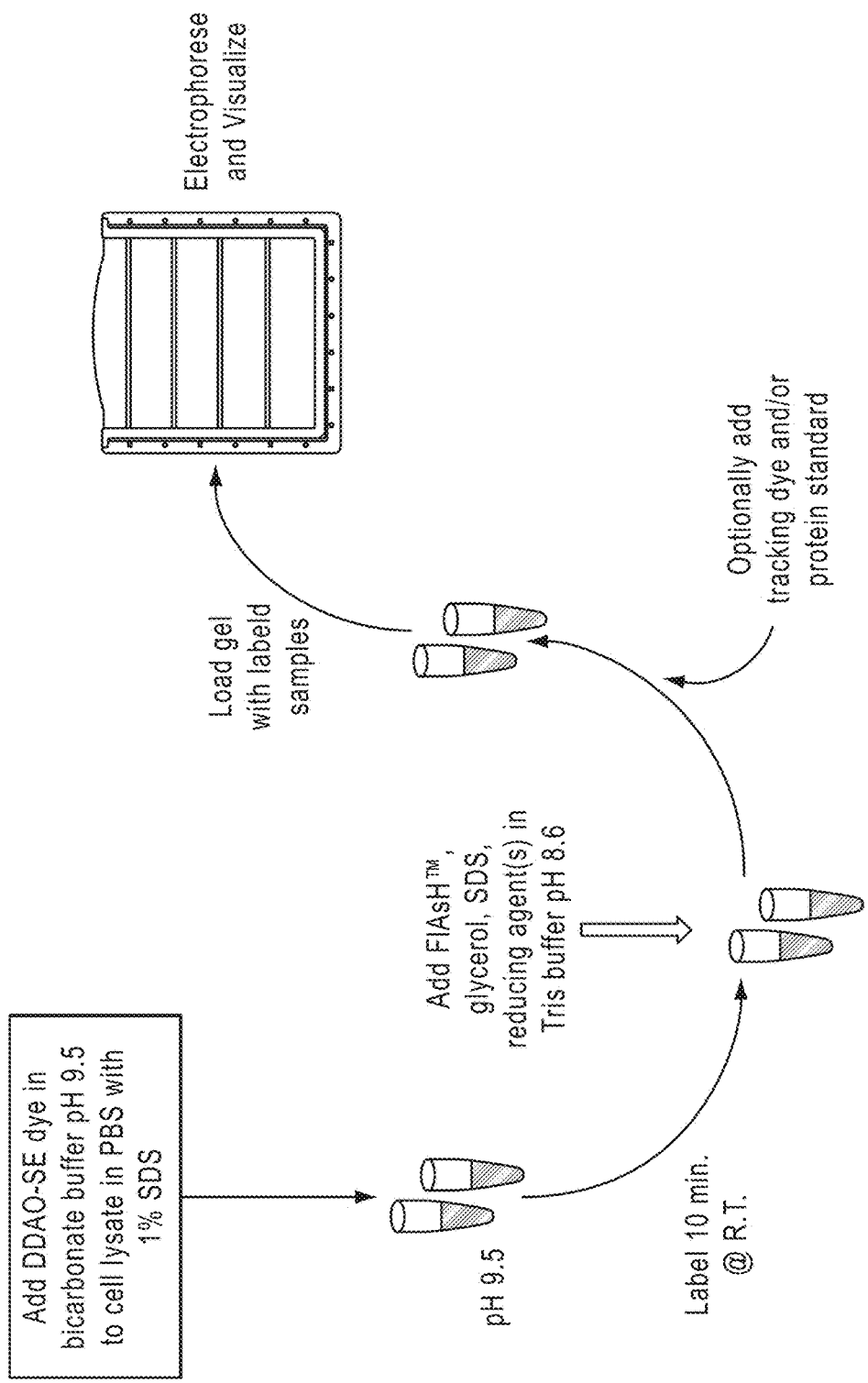
FIG. 3 is a schematic illustrating certain embodiments of the methods for protein expression analysis using labeling and analysis methods described herein.

FIG. 3 illustrates a schematic of one embodiment of such protein labeling and analysis methods, wherein a mixture of DDAO-SE™ (Invitrogen Corp., Carlsbad) in bicarbonate buffer (pH 9.5) is added to cell lysate that also contains a protein of interest tagged with a peptide tag having a tetracysteine moiety. This reaction mixture is allowed to react at room temperature (RT) for 10 minutes and then a Tris buffer (pH 8.6) buffer containing FlAsH-EDT$_2$ (Lumio™ Green, Invitrogen Corp., Carlsbad, Calif.), glycerol, SDS and at least one reducing agent is added. A tracking dye and/or labeled protein standards are optionally added, and the mixture is then loaded into sample wells in an electrophoresis gel contained in an electrophoresis cassette where the labeled proteins are separated and visualized using fluorescence imaging detection.

In methods using tag binding fluorogenic reagents/dyes in combination with amine reactive fluorescent dyes for protein analysis, including protein expression analysis, a first reaction mixture is formed by admixing a mixture of proteins containing a tagged protein of interest with a composition that includes a first buffer having a pH between about pH 8 and about pH 10 and a tag binding fluorogenic reagent/dye that binds to a tag attached to the protein of interest, at least one reducing agent, and an optional anionic surfactant. The first buffer used in this initial step does not include buffer compounds or additives that have primary or secondary amine moieties. However, the methods described herein can tolerate low levels of amines that may be already present in the protein sample. This first reaction mixture is then incubated for a first incubation time at a first incubation temperature, resulting in the labeling of the tagged protein of interest, and thereby obtaining a measure of the protein of interest present in the protein mixture. The first reaction mixture is further admixed with a second buffer having a pH between about pH 8 and about pH 10, and an amine reactive fluorescent dye, thereby forming a second reaction mixture. The second reaction mixture is then incubated for a second incubation time at a second incubation temperature, resulting in the labeling of the mixture of proteins, including the tagged protein of interest, and thereby obtaining a measure of the total proteins present. This labeling method results in the mixture of proteins, including the tagged protein of interest, being labeled with one fluorescent moiety (from the amine fluorescent dye), and the protein of interest also being labeled with a second fluorescent moiety (from the fluorogenic reagent).

Consequently, a population of proteins in the protein mixture becomes fluorescently labeled with both fluorescent dyes, while the remaining proteins in the mixture are labeled with only the amine reactive fluorescent dye. In addition to labeling the protein mixture, such protein analysis methods further includes separating the fluorescently labeled protein mixture using electrophoretic methods, chromatographic methods, or combinations thereof, and visualizing/measuring the fluorescence of the separated proteins using fluorescence imaging techniques. The amine reactive fluorescent dye has different spectral emission properties than the fluorescent moiety bound to the tag on the protein of interest, therefore the resulting fluorescence measurements are compared to obtain a measure of the protein of interest relative to the total proteins present in the protein mixture. The amine reactive fluorescent dye and the fluorogenic reagent that binds to a tag can be excited by the same excitation source or they can be excited by different excitation sources. In certain embodiments of such protein analysis methods, the first buffer includes at least one reducing agent and the second buffer does not contain a reducing agent, while in other embodiments both the first buffer and second buffer include at least one reducing agent. In certain embodiments, such protein analysis methods are used for protein expression analysis, and comparison of the fluorescence measurements of the two fluorescent moieties yields a measure of the level of protein expression of a protein of interest.

In another aspect of the methods using tag binding fluorogenic reagents/dyes in combination with amine reactive fluorescent dyes for protein analysis, including protein expression analysis, a first reaction mixture is initially formed by admixing a mixture of proteins containing a tagged protein of interest with a composition containing a first buffer having a pH between about pH 7 and about pH 10, a fluorogenic reagent/dye that binds to a tag attached to a protein of interest present, at least one reducing agent, and an optional anionic surfactant. The first reaction mixture is then incubated for a first incubation time at a first incubation temperature. Upon binding the tag binding fluorogenic reagent becomes fluorescent, thereby fluorescently labeling the protein of interest. The first mixture is then admixed with an amine reactive fluorescent dye and incubated for a second incubation time at a second incubation temperature, thereby labeling all proteins in the mixture, including the protein of interest. The amine reactive dye can be in an aqueous solution or buffer, an aqueous solution comprising a non-aqueous solvent, or a non-aqueous solvent. This labeling method results in the mixture of proteins, including the tagged protein of interest, being labeled with one fluorescent moiety (from the amine fluorescent dye), and the protein of interest also being labeled with a second fluorescent moiety (from the fluorogenic reagent).

Consequently, a population of proteins in the protein mixture becomes fluorescently labeled with both fluorescent dyes, while the remaining proteins in the mixture are labeled with the amine reactive fluorescent dye. The second reaction mixture containing the labeled proteins are then separated using electrophoretic methods, chromatographic methods, or combinations thereof. The protein analysis methods further includes visualizing the fluorescence of the separated proteins using fluorescence imaging techniques and comparing the fluorescence from the two fluorescent moieties. The amine reactive fluorescent dye has different spectral emission properties than the fluorescent moiety bound to the tag on the protein of interest, therefore the resulting fluorescence measurements can be compared to obtain a measure of the protein of interest relative to the total proteins present in the protein mixture. The amine reactive fluorescent dye and the fluorogenic reagent that binds to a tag can be excited by the same excitation source or they can be excited by different excitation sources. In certain embodiments, such protein analysis methods are used for protein expression analysis, and comparison of the fluorescence measurements of the two fluorescent moieties yields a measure of the level of protein expression of a protein of interest. In certain embodiments of such protein analysis methods, the second buffer includes at least one reducing agent and the first buffer does not contain a reducing agent, while in other embodiments both the first buffer and second buffer include at least one reducing agent. In certain embodiments, such protein analysis method can include admixing the second reaction mixture with a second buffer prior to the separation step, wherein the second buffer has a pH between about pH 7 and about pH 10.

Figure 4A:
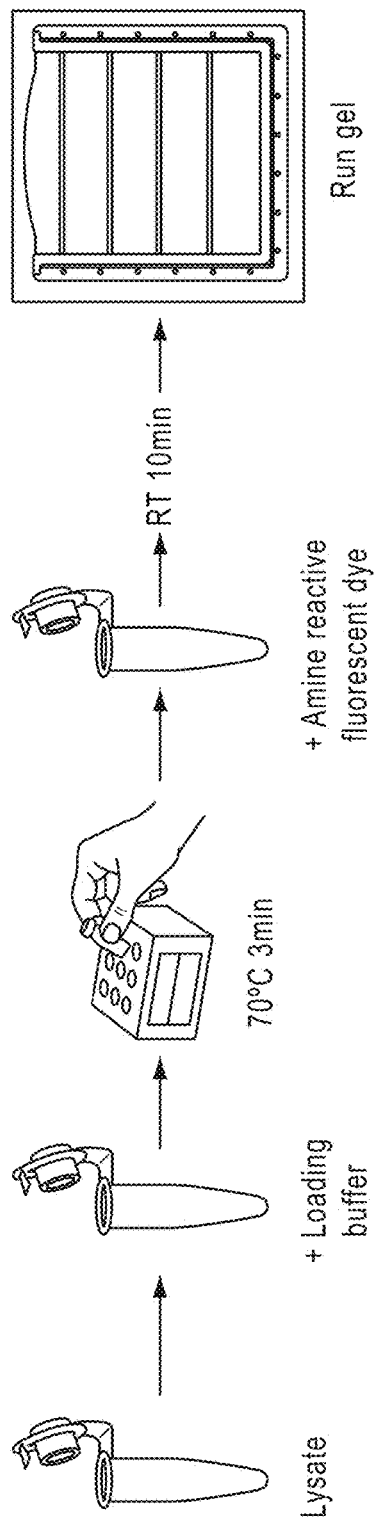
FIG. 4 is a schematic illustration of an embodiment of the methods for protein expression analysis using labeling and analysis described herein.
Figure 4B:
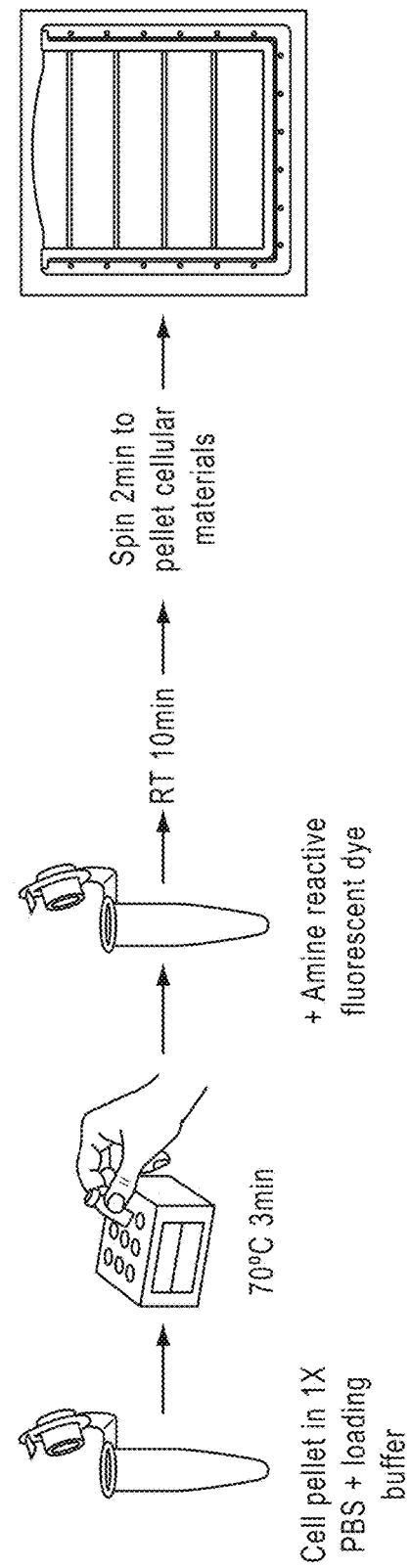

FIG. 4 illustrates a schematic of such protein labeling and analysis methods, wherein a loading buffer is added to a lysate containing a tagged protein of interest and the mixture is incubated for three minutes at 70° C. Following incubation an amine reactive fluorescent dye is added and the mixture is further incubated for ten minutes at room temperature prior to slab gel electrophoresis. Alternatively, pelletted cell resuspended with loading buffer are incubated for three minutes at 70° C., followed by addition of an amine reactive fluorescent dye and further incubation for ten minutes at room temperature prior to slab gel electrophoresis. In certain embodiments the loading buffer is a mixture of FlAsH-EDT$_2$ (Lumio™ Green, Invitrogen Corp., Carlsbad, Calif.) in phosphate buffer (pH 8.5), glycerol, SDS, a tracking dye and at least one reducing agent, and the amine reactive fluorescent dye is BODIPY TR-X SE or BODIPY 650/665 SE.

Figure 17:
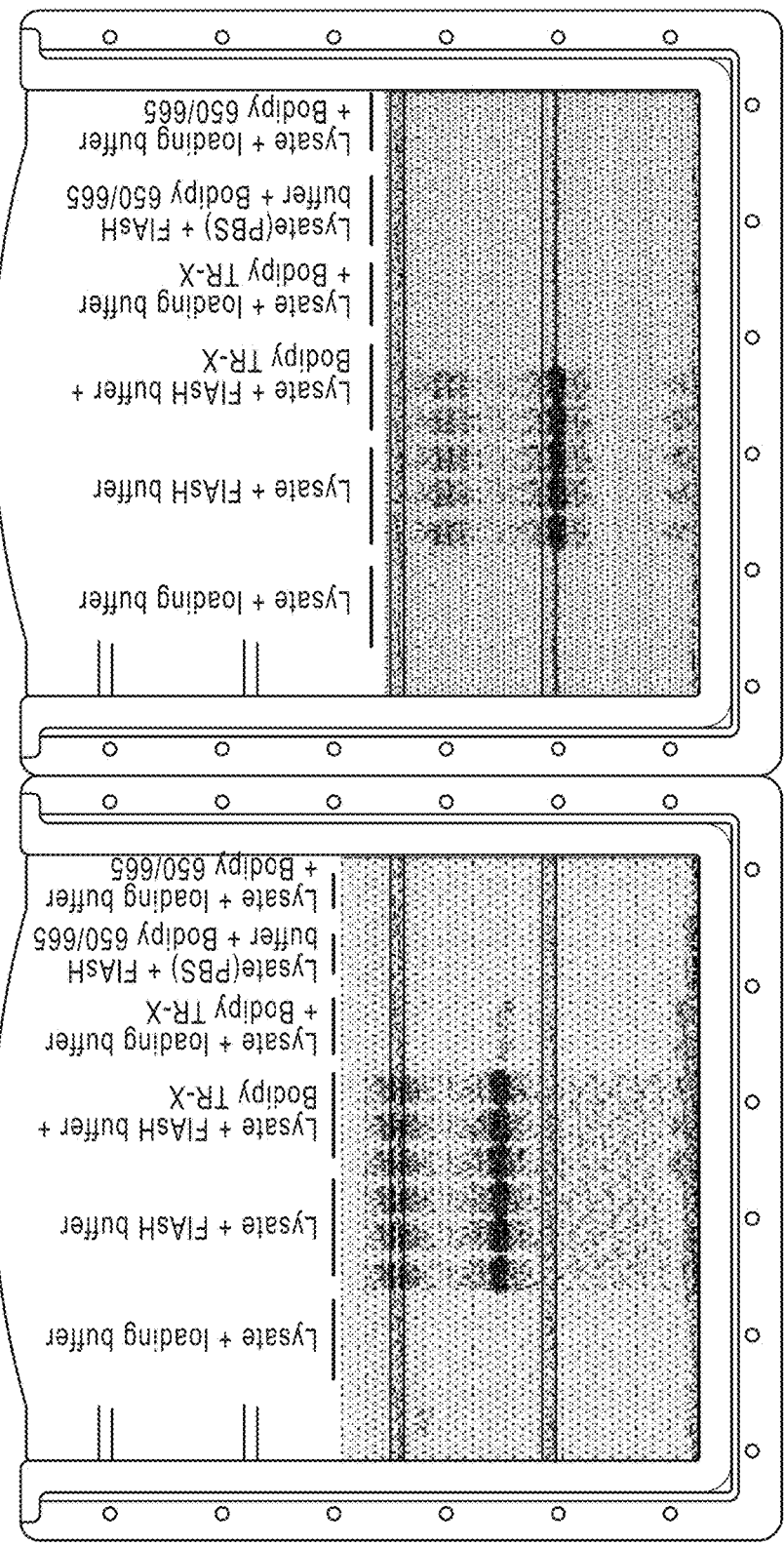
FIG. 17 are gel cassette images obtained using 473 nm excitation with 520 nm emission and shows the specificity of labeling with a biarsenical reagent to the protein of interest in an *E. coli* lysate.
Figure 18:
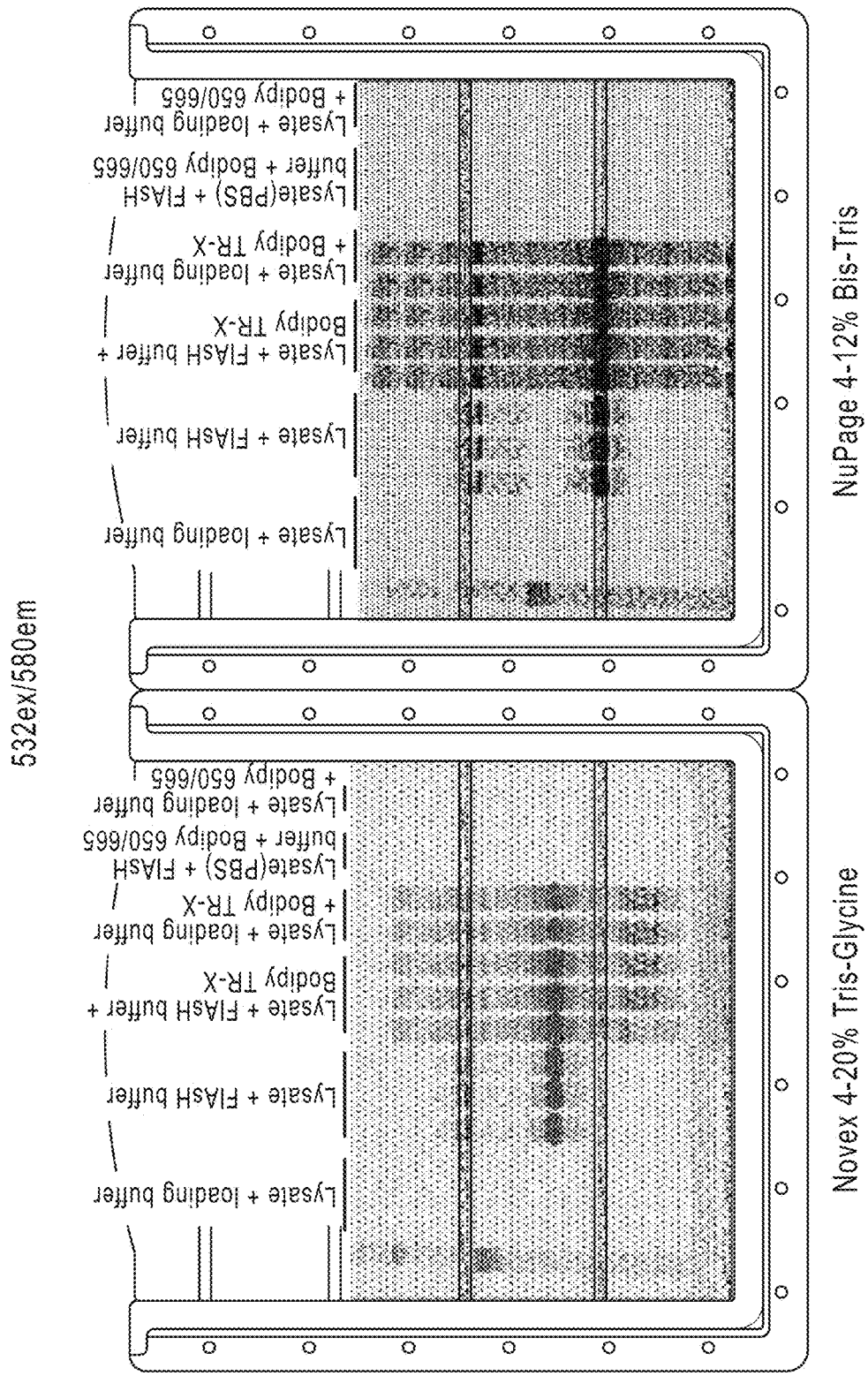
FIG. 18 are gel cassette images obtained using 532 nm excitation with 580 nm emission and shows the total protein labeling of an *E. coli* lysate with BODIPY TR-X SE.
Figure 19:
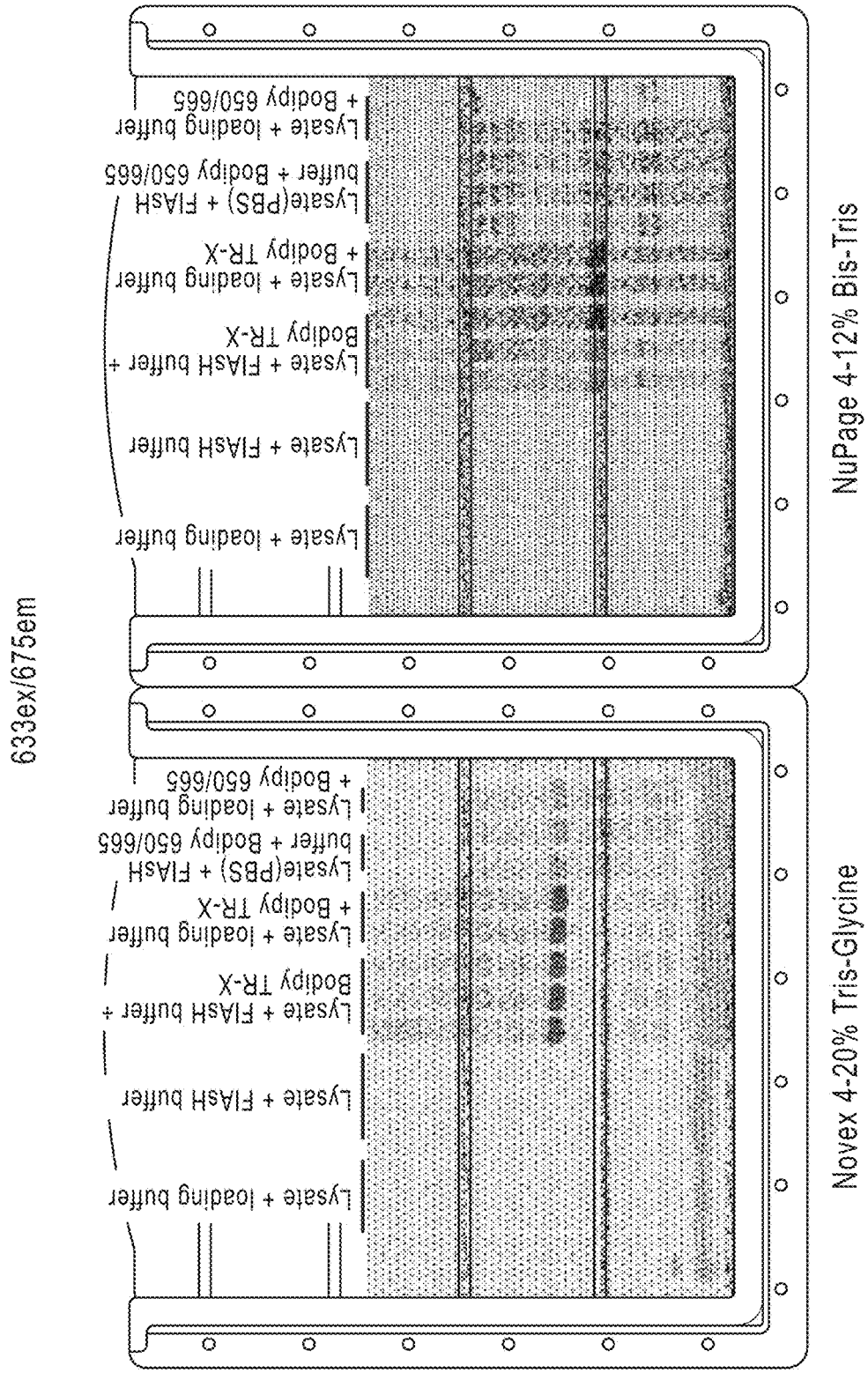
FIG. 19 are gel cassette images obtained using 633 nm excitation with 675 nm emission and shows the total protein labeling of an *E. coli* lysate with BODIPY 650/665 SE.

FIGS. 17-19 show gel images obtained for an *E. coli* lysate containing a protein having a GFP tetracysteine tag labeled using such methods. FIG. 17 shows images obtained using 473 nm excitation with 520 nm emission and shows the specificity of labeling with the biarsenical reagent, FlAsH-EDT$_2$ (Lumio™ Green, Invitrogen Corp., Carlsbad, Calif.), to the protein of interest. FIG. 18 shows images obtained using 532 nm excitation with 580 nm emission and shows the total protein labeling with BODIPY TR-X SE. FIG. 19 shows images obtained using 633 nm excitation with 675 nm emission and shows the total protein labeling with BODIPY 650/665 SE.

Figure 20:
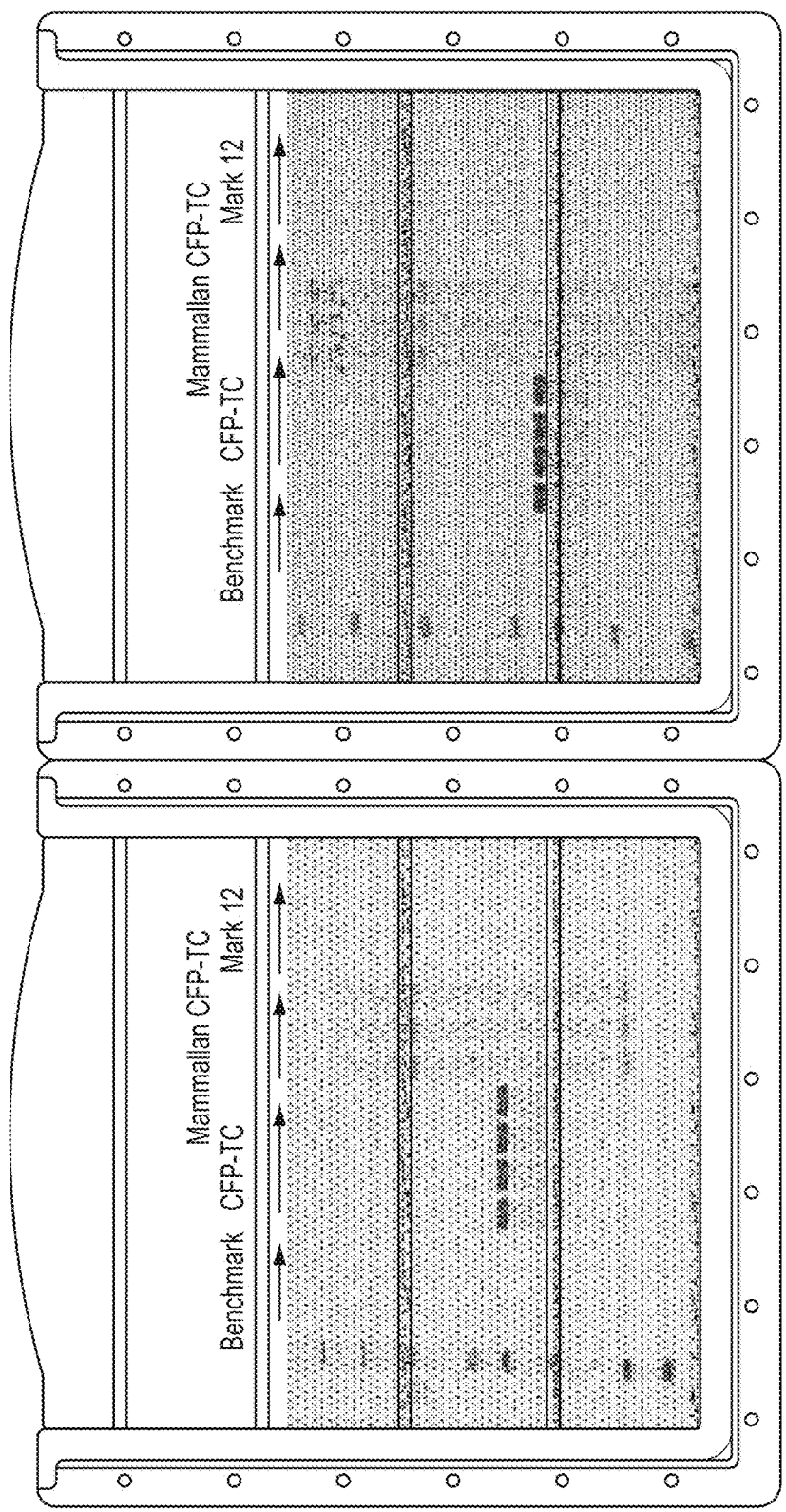
FIG. 20 are images obtained using 473 nm excitation with 520 nm emission and shows the specificity of labeling with the biarsenical reagent to the protein of interest in an *E. coli* lysate.
Figure 21:
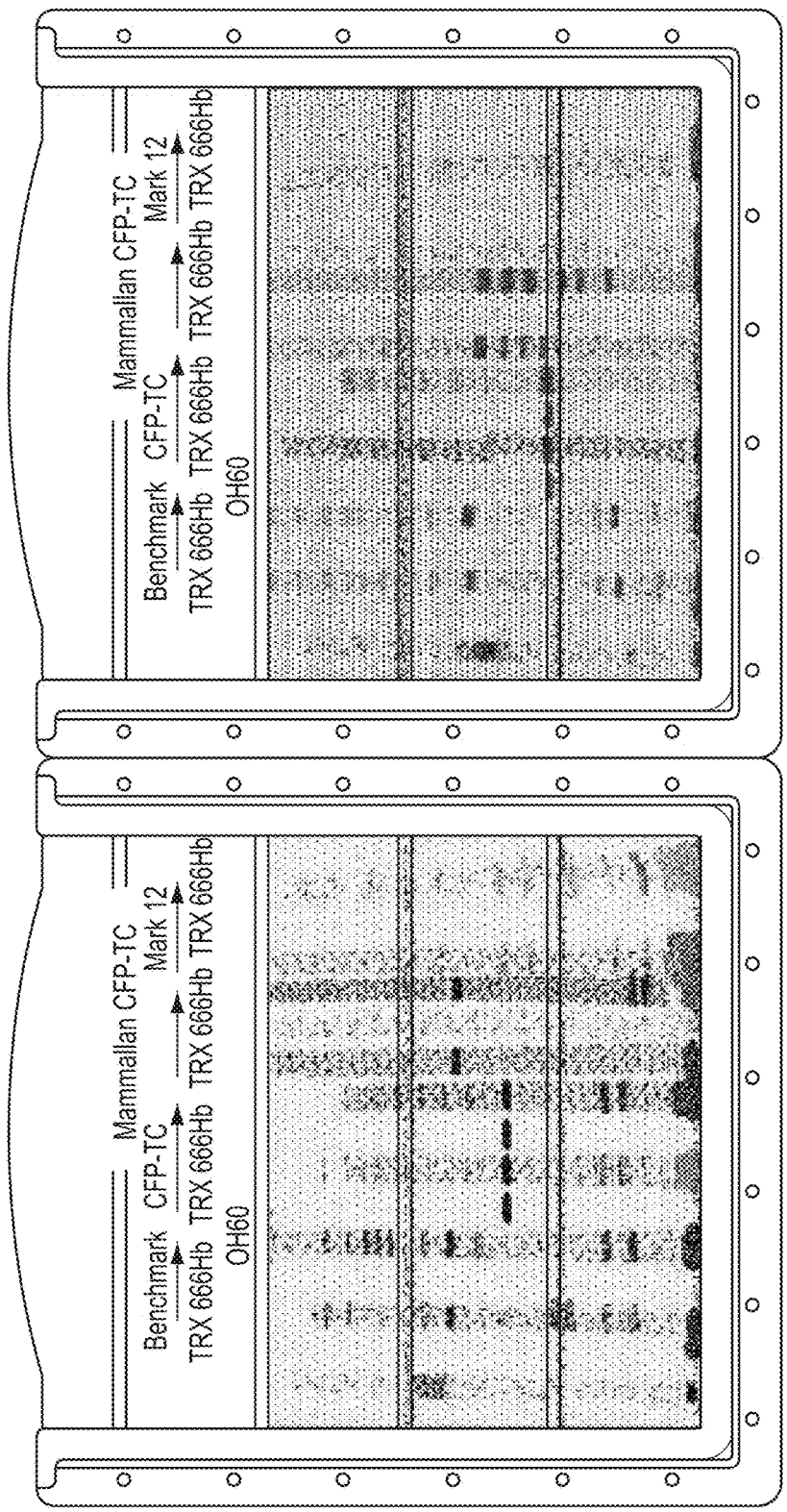
FIG. 21 are images obtained using 532 nm excitation with 580 nm emission and shows the total protein labeling of an *E. coli* lysate, a mammalian cell lysate, a protein standard set and a protein ladder with BODIPY TR-X SE.
Figure 22:
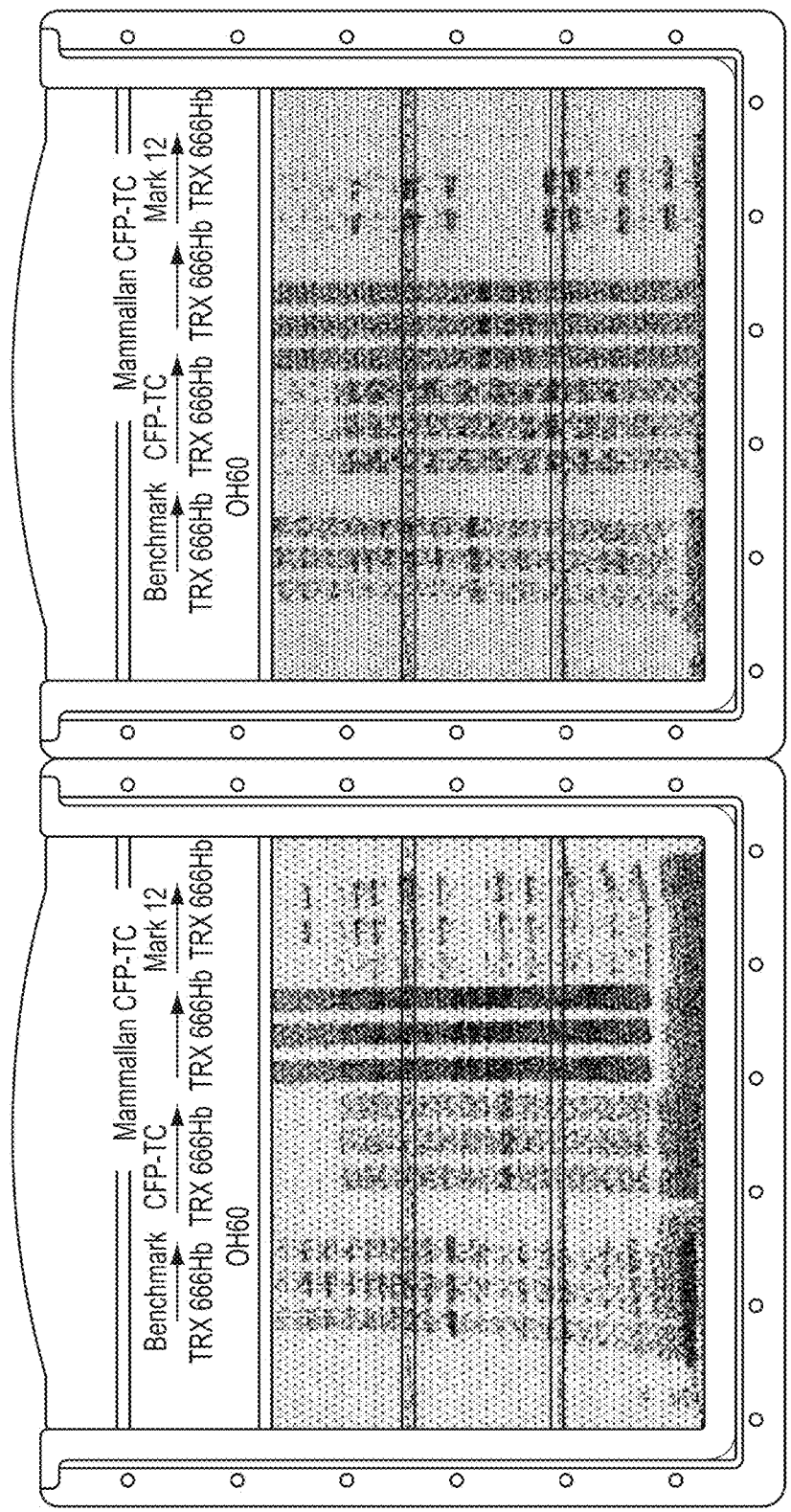
FIG. 22 are images obtained using 633 nm excitation with 675 nm emission and shows the total protein labeling of an E. coli lysate, a mammalian cell lysate, a protein standard set and a protein ladder with BODIPY 650/665 SE.

FIGS. 20-22 show gel images obtained for an *E. coli* lysate containing a protein having a GFP tetracysteine tag and mammalian cell lysate containing a protein having a CFP tetracysteine tag, each of which labeled were using methods described above. FIG. 20 shows images obtained using 473 nm excitation with 520 nm emission and shows the specificity of labeling with the biarsenical reagent, FlAsH-EDT$_2$ (Lumio™ Green, Invitrogen Corp., Carlsbad, Calif.), to the protein of interest. FIG. 21 shows images obtained using 532 nm excitation with 580 nm emission and shows the total protein labeling with BODIPY TR-X SE. FIG. 22 shows images obtained using 633 nm excitation with 675 nm emission and shows the total protein labeling with BODIPY 650/665 SE.

Protein Expression Analysis Using Tag Binding Fluorogenic Reagents/Dyes with Amine Reactive Fluorogenic Reagents In one aspect of the method described herein that uses tag binding fluorogenic reagent/dyes in combination with amine reactive fluorogenic reagents for protein analysis, including protein expression analysis, a first reaction mixture is formed by admixing a mixture of proteins containing a tagged protein of interest with a composition that includes a first buffer having a pH between about pH 8 and about pH 10, an amine reactive fluorogenic reagent, an alkali cyanide (or a less toxic alternative such as acetone cyanohydrin or a nitrile such as mandelonitrile), and an optional anionic surfactant. Acetone cyanohydrin and nitriles may be preferable over an alkali cyanide because they have significantly reduced toxicity. The first buffer used in this initial step does not include buffer compounds or additives that have primary or secondary amine moieties. However, the methods described herein can tolerate low levels of amines that may be already present in the protein sample. This first reaction mixture is then incubated for a first incubation time at a first incubation temperature before forming a second reaction mixture by admixing a second buffer having a pH from about pH 6 to about pH 9. The second buffer has a buffer capacity greater than the first buffer, thereby maintaining the pH of the second reaction mixture from about pH 6 to about pH 9. The second buffer also contains a fluorogenic reagent/dye that binds to a tag attached to a protein interest present in the mixture of proteins, an optional anionic surfactant that may be the same or different than the anionic surfactant used in the first buffer, and at least one reducing agent. This resulting mixture is incubated for a second incubation time at a second incubation temperature, whereby the fluorogenic reagent becomes fluorescent upon binding to the tag on the protein of interest. This labeling method results in the mixture of proteins, including the tagged protein of interest, being labeled with one fluorescent moiety (from the amine fluorogenic reagent), and the protein of interest also being labeled with a second fluorescent moiety (from the tag binding fluorogenic reagent).

Consequently, a population of proteins in the protein mixture becomes fluorescently labeled with two fluorescent moieties, while the remaining proteins in the mixture are labeled with one fluorescent moiety from the amine reactive fluorescent reagent. In addition to labeling the protein mixture, such protein analysis methods further includes separating the fluorescently labeled protein mixture using electrophoretic methods, chromatographic methods, or combinations thereof, and visualizing/measuring the fluorescence of the separated proteins using fluorescence imaging techniques. The fluorescent moiety formed from the amine reactive fluorogenic reagent has different spectral emission properties than the fluorescent moiety bound to the tag on the protein of interest, therefore the resulting fluorescence measurements are compared to obtain a measure of the protein of interest relative to the total proteins present in the protein mixture. The fluorescent moiety formed from the amine reactive fluorogenic reagent and the fluorogenic reagent that binds to a tag can be excited by the same excitation source or they can be excited by different excitation sources. In certain embodiments of such protein analysis methods, the first buffer includes at least one reducing agent and the second buffer does not contain a reducing agent, while in other embodiments both the first buffer and second buffer include at least one reducing agent. In certain embodiments, such protein analysis methods are used for protein expression analysis, and comparison of the fluorescence measurements of the two fluorescent moieties yields a measure of the level of protein expression of a protein of interest.

Alternatively, in method described herein that uses tag binding fluorogenic dyes in combination with amine reactive fluorogenic reagents for protein analysis, including protein expression analysis, a first reaction mixture is formed by admixing a mixture of proteins that contains a tagged protein of interest with a composition containing a first buffer having a pH from about pH 8 to about pH 10, a tag binding fluorogenic dye, an amine reactive fluorogenic reagent, an alkali cyanide or acetone cyanohydrin or a nitrile, and an optional anionic surfactant. The first buffer used in this initial step does not include buffer compounds or additives that have primary or secondary amine moieties. However, the methods described herein can tolerate low levels of amines that may be already present in the protein sample. This first reaction mixture is then incubated for a first incubation time at a first incubation temperature before forming a second reaction mixture by admixing a second buffer having a pH from about pH 6 to about pH 9. The second buffer has a buffer capacity greater than the first buffer, thereby maintaining the pH of the second reaction mixture from about pH 6 to about pH 9. The second buffer optionally contains at least one reducing agent, or the reducing agent or agents can be added after forming the second reaction mixture. The second mixture is then incubated for a second incubation time at a second incubation temperature. With this labeling method the tag binding fluorogenic reagent becomes fluorescent upon binding to the tag on the protein of interest, and the amine reactive fluorogenic reagent becomes fluorescent upon reacting with amine groups on the proteins. This labeling method results in the mixture of proteins, including the tagged protein of interest, being labeled with the fluorescent moiety from the amine reactive fluorogenic reagent, whereas the protein of interest also is labeled with a second fluorescent moiety from the tag binding fluorogenic reagent.

Consequently, a population of proteins in the protein mixture becomes fluorescently labeled with two fluorescent moieties, while the remaining proteins in the mixture are labeled with one fluorescent moiety from the amine reactive fluorescent reagent. In addition to labeling the protein mixture, such protein analysis methods further includes separating the fluorescently labeled protein mixture using electrophoretic methods, chromatographic methods, or combinations thereof, and visualizing/measuring the fluorescence of the separated proteins using fluorescence imaging techniques. The fluorescent moiety formed from the amine reactive fluorogenic reagent has different spectral emission properties than the fluorescent moiety bound to the tag on the protein of interest, therefore the resulting fluorescence measurements are compared to obtain a measure of the protein of interest relative to the total proteins present in the protein mixture. The fluorescent moiety formed from the amine reactive fluorogenic reagent and the fluorogenic reagent that binds to a tag can be excited by the same excitation source or they can be excited by different excitation sources. In certain embodiments of such protein analysis methods, the first buffer includes at least one reducing agent and the second buffer does not contain a reducing agent, while in other embodiments both the first buffer and second buffer include at least one reducing agent. In certain embodiments, such protein analysis methods are used for protein expression analysis, and comparison of the fluorescence measurements of the two fluorescent moieties yields a measure of the level of protein expression of a protein of interest.

Materials and Methods

The fluorogenic reagents used in the labeling and analysis methods described herein are non-fluorescent prior to reaction with proteins, protein fragments or mixtures of proteins, and form a fluorescent label only after reacting with the proteins, protein fragments or mixtures of proteins. Such reactions include, but are not limited to, binding with tags attached to the proteins or reaction with amine groups on the proteins. Consequently, the protein labeling methods that use such reagents can have lower background fluorescence and may allow for greater sensitivity in protein detection. Furthermore, such methods may not require extensive washing to remove any un-reacted dye as can be the case for non-fluorogenic dyes used to label proteins. For many fluorescent dyes that are used to label proteins, washing is performed in order to reduce background fluorescence in the gel, particularly in lower molecular weight regions.

In certain embodiments the sensitivity of the protein labeling method described herein is at least 0.2 ng of protein. In other embodiments the sensitivity of the protein labeling method described herein is at least 0.1 ng of protein. In other embodiments the sensitivity of the protein labeling method described herein is at least 0.05 ng of protein. In other embodiments the sensitivity of the protein labeling method described herein is from about 0.01 ng of protein to about 0.2 ng of protein. In other embodiments the sensitivity of the protein labeling method described herein is from about 0.05 ng of protein to about 0.2 ng of protein. In other embodiments the sensitivity of the protein labeling method described herein is from about 0.1 ng of protein to about 0.2 ng of protein.

The sensitivity of detection obtained using the protein labeling methods described herein is shown in FIG. 6A, FIG. 6B, FIG. 7A, FIG. 7B and FIG. 7C, wherein various concentrations of labeled bovine serum albumin (BSA) and lysozyme were electrophoretically separated and detected. Both figures show the fluorescent images obtained using the methods described herein compared with images obtained using staining with SimplyBlue™ SafeStain.

The concentration of the fluorogenic reagents (amine reactive fluorogenic reagent and the tag binding fluorogenic reagent) used in the protein labeling methods described herein are in the range from 50 nM to 100 mM. In certain embodiments, the concentration is in the range from 50 nM to 50 mM. In other embodiments, the concentration is in the range from 50 nM to 25 mM. In certain embodiments, the concentration is in the range from 50 nM to 10 mM. In certain embodiments, the concentration is in the range from 50 nM to 5 mM. In certain embodiments, the concentration is in the range from 100 nM to 10 mM. In certain embodiments, the concentration is in the range from 100 nM to 5 mM. In certain embodiments, the concentration is in the range from 200 nM to 5 mM. In certain embodiments, the concentration is in the range from 50 nM to 100 µM. In certain embodiments, the concentration is in the range from 1 µM to 100 µM. In certain embodiments such concentrations are obtained by dilution of a stock solution of the fluorogenic reagents having a concentration in the range from 100 nM to 200 mM. In certain embodiments the concentration of the stock solution is 100 mM. In certain embodiments the concentration of the stock solution is 50 mM. In certain embodiments the concentration of the stock solution is 20 mM. In certain embodiments the concentration of the stock solution is 10 mM. In certain embodiments the concentration of the stock solution is 1 mM. In certain embodiments the concentration of the stock solution is 500 µM. In certain embodiments the concentration of the stock solution is from 10 µM to 500 µM. In certain embodiments the concentration of the stock solution is from 1 µM to 100 µM. In certain embodiments the concentration of the stock solution is 10 µM. In certain embodiments the concentration of the stock solution is from 100 µM to 200 µM.

The amine reactive fluorogenic reagents used in the protein labeling methods described herein include, but are not limited to, aroyl-2-quinoline-carboxaldehyde type reagents. Such reagents have been described in U.S. Pat. No. 5,459,272 and U.S. Pat. No. 5,631,374, each of which is herein incorporated by reference in their entirety. By way of example only, the aroyl-2-quinoline-carboxaldehyde reagent used in the total protein analysis methods described herein is 3-(4-carboxybenzoyl)quinoline-2-carboxaldehyde or 3-(2-furoyl)quinoline-2-carboxaldehyde). In certain embodiments, the amine reactive fluorogenic reagent is 3-(2-furoyl)quinoline-2-carboxaldehyde), while other embodiments, the amine reactive fluorogenic reagent is 3-(4 carboxybenzoyl)-quinoline-2-carboxaldehyde.

The fluorescent dyes described herein function as reporter molecules to confer a detectable signal, directly or indirectly, to the sample as a result of conjugation to a functional group on the protein, including, but not limited to, amine groups or thiol groups. This results in the ability to detect the total protein in a sample generally in combination with detection of a subset of the total protein of the sample. In such instances the total protein labels are detectable distinguished from the dye that labels a subset of the total protein in the sample.

Where the detectable response is a fluorescence response, it is typically a change in fluorescence, such as a change in the intensity, excitation or emission wavelength, distribution of fluorescence, fluorescence lifetime, fluorescence polarization, or a combination thereof.

The fluorescent dyes can be any fluorophore known to one skilled in the art. A wide variety of fluorophores that may be suitable for total protein labeling as described herein are already known in the art (RICHARD P. HAUGLAND, MOLECULAR PROBES HANDBOOK OF FLUORESCENT PROBES AND RESEARCH PRODUCTS (2002)). A fluorescent dye used in the methods and compositions described herein is any chemical moiety that exhibits an absorption maximum beyond 280 nm. Such chemical moieties include, but are not limited to, a pyrene, sulfonated pyrenes, sulfonated coumarins, sulfonated carbocyanines, sulfonated xanthenes, an anthracene, a naphthalene, an acridine, a stilbene, an indole an isoindole, an indolizine, a benzindole, an oxazole or benzoxazole, a thiazole or benzothiazole, a 4-amino-7-nitrobenz-2-oxa-1, 3-diazole (NBD), a carbocyanine, a carbostyryl, a porphyrin, a salicylate, an anthranilate, an azulene, a perylene, a pyridine, a quinoline, an isoquinoline, a chromene, a borapolyazaindacene, a xanthene, a fluorescein, a rosamine, a rhodamine, a rhodamine, benzo- or dibenzofluorescein, seminaphthofluorescein, a naphthofluorescein, a bimane, an oxazine or a benzoxazine, a carbazine, a phenalenone, a coumarin, a benzofuran, a benzphenalenone) and derivatives thereof. As used herein, oxazines include resorufins, aminooxazinones, diaminooxazines, and their benzo-substituted analogs.

In one aspect the fluorescent dyes contains one or more aromatic or heteroaromatic rings, that are optionally substituted one or more times by a variety of substituents, including without limitation, halogen, nitro, sulfo, cyano, alkyl, perfluoroalkyl, alkoxy, alkenyl, alkynyl, cycloalkyl, arylalkyl, acyl, aryl or heteroaryl ring system, benzo, or other substituents typically present on chromophores or fluorophores known in the art. In one aspect the fluorophore is a xanthene that comprises one or more julolidine rings.

In an exemplary embodiment, the dyes are independently substituted by substituents selected from the group consisting of hydrogen, halogen, amino, substituted amino, alkyl, substituted alkyl, aryl, substituted aryl, heteroaryl, substituted heteroaryl, alkoxy, sulfo, reactive group, solid support and carrier molecule. In another embodiment, the xanthene dyes of this invention comprise both compounds substituted and unsubstituted on the carbon atom of the central ring of the xanthene by substituents typically found in the xanthene-based dyes such as phenyl and substituted-phenyl moieties. Most preferred dyes are rhodamine, fluorescein, borapolyazaindacene, indole and derivatives thereof.

In certain embodiments, the total protein labels and expression tag labels (tag binding fluorogenic reagents) are chemically reactive, and are substituted by at least one reactive group. The reactive group functions as the site of attachment for another moiety, such as a an amine group on a protein or an expression tag on a protein, wherein the reactive group chemically reacts with an appropriate reactive or functional group on the protein.

In an exemplary embodiment, the total protein labels and expression tag labels further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. The reactive group may be attached to any appropriate site on the label. Typically, the conjugation reaction between the reactive group and the total protein labels or expression tag labels results in one or more atoms of the reactive group being incorporated into a new linkage attaching the total protein labels and expression tag labels to the protein. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiols | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

Choice of the reactive group used to attach the total protein labels or expression tag labels to the protein to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. In proteins a variety of sites may occur including, but not limited to, amines, thiols, alcohols and phenols.

The total protein labels that comprise a reactive group may also be referred to as sequence independent fluorescent dyes or sequence independent fluorogenic dyes.

Typically, the reactive group will react with an amine, a thiol, an alcohol, an aldehyde or a ketone In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a sulfonyl halide, or a thiol group.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the total protein labels and expression tag labels form a covalent bond with an amine containing molecule in a protein. In another aspect, the compound comprises at least one reactive group that selectively reacts with a thiol group. This thiol-reactive group is selected from the group consisting of maleimide, haloalkyl and haloacetamide.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of proteins, nucleotides, oligonucleotides, or haptens. Where the reactive group is a maleimide, haloalkyl or haloacetamide the resulting compound is particularly useful for conjugation to thiol-containing substances. Where the reactive group is a hydrazide, the resulting compound is particularly useful for conjugation to periodate-oxidized carbohydrates and glycoproteins.

By way of example only, amine reactive fluorescent dyes used in the protein labeling methods described herein include dyes that contain a pyrene, sulfonated pyrenes, sulfonated coumarins, sulfonated carbocyanines, sulfonated xanthenes, an anthracene, a naphthalene, an acridine, a stilbene, an indole an isoindole, an indolizine, a benzindole, an oxazole or benzoxazole, a thiazole or benzothiazole, a 4-amino-7-nitrobenz-2-oxa-1, 3-diazole (NBD), a carbocyanine, a carbostyryl, a porphyrin, a salicylate, an anthranilate, an azulene, a perylene, a pyridine, a quinoline, an isoquinoline, a chromene, a borapolyazaindacene, a xanthene, a fluorescein, a rosamine, a rhodamine, a rhodamine, benzo- or dibenzofluorescein, seminaphthofluorescein, a naphthofluorescein, a bimane, an oxazine or a benzoxazine, a carbazine, a phenalenone, a coumarin, a benzofuran, a benzphenalenone) and derivatives thereof. As used herein, oxazines include resorufins, aminooxazinones, diaminooxazines, and their benzo-substituted analogs. Such amine reactive dyes also include reactive moieties selected from an acyl azide, a carbonyl azide, an isothiocyanate, an isocyanate, a succinimidyl ester, a carboxylic ester, a carboxylic acid, a succinimidyl ester, a sulfosuccinimidyl ester, an STP ester, a tetrafluorophenyl ester, a sulfonyl chloride, an acid halide, an aldehyde, a carboxyaldehyde a dichlorotriazine, an NBD chloride, or an NBD fluoride.

Such amine reactive fluorescent dyes used in the protein labeling methods described herein include, but are not limited to, Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610-X, Alexa Fluor® 633, Alexa Fluor® 647, Alexa Fluor® 660, Alexa Fluor® 680, Alexa Fluor® 700, Alexa Fluor® 750, Alexa Fluor® 790, AMCA-X, BODIPY® 630/650, BODIPY® 650/665, BODIPY® FL, BODIPY® TMR, BODIPY® TR, BODIPY® TR-X, Cascade Blue®, Dinitrophenyl, Fluorescein, HEX, JOE, Marina Blue®, Oregon Green® 488, Oregon Green® 514, Pacific Blue™, Pacific Orange™, Rhodamine Green™, QSY® 7, QSY® 9, QSY® 21, QSY® 35, ROX, Rhodamine Red™, TET, TAMRA, tetramethyl rhodamine, FAM, Texas Red® and 7-hydroxy-9H-(1,3-dichloro-9,9-dimethylacridin-2-one) succinimidyl ester (DDAO-SE).

The concentration of the amine reactive fluorescent dyes used in the protein labeling methods described herein are in the range from 50 nM to 100 mM. In certain embodiments, the concentration is in the range from 50 nM to 50 mM. In other embodiments, the concentration is in the range from 50 nM to 25 mM. In certain embodiments, the concentration is in the range from 50 nM to 10 mM. In certain embodiments, the concentration is in the range from 50 nM to 5 mM. In certain embodiments, the concentration is in the range from 100 nM to 10 mM. In certain embodiments, the concentration is in the range from 100 nM to 5 mM. In certain embodiments, the concentration is in the range from 200 nM to 5 mM. In certain embodiments, the concentration is in the range from 50 nM to 100 µM. In certain embodiments, the concentration is in the range from 1 µM to 100 µM. In certain embodiments such concentrations are obtained by dilution of a stock solution of the fluorogenic reagents having a concentration in the range from 100 nM to 200 mM. In certain embodiments the concentration of the stock solution is 100 mM. In certain embodiments the concentration of the stock solution is 50 mM. In certain embodiments the concentration of the stock solution is 20 mM. In certain embodiments the concentration of the stock solution is 10 mM. In certain embodiments the concentration of the stock solution is 1 mM. In certain embodiments the concentration of the stock solution is 500 µM. In certain embodiments the concentration of the stock solution is from 10 µM to 500 µM. In certain embodiments the concentration of the stock solution is from 1 µM to 100 µM. In certain embodiments the concentration of the stock solution is 10 µM. In certain embodiments the concentration of the stock solution is from 100 µM to 200 µM.

The fluorogenic reagents/dyes that bind to tags attached to proteins used in the protein labeling methods described herein are biarsenical fluorophore, including, a biarsenical derivative of fluorescein, such as, by way of example only, FlAsH-EDT$_2$ (4'-5'-bis(1,3,2-dithioarsolan-2-yl)fluorescein-(2,2-ethanedithiol)$_2$) (Lumio™ Green, Invitrogen Corp., Carlsbad, Calif.), or a biarsenical derivative of resorufin such as, by way of example only, ReAsh-EDT$_2$ (Lumio™ Red, Invitrogen Corp., Carlsbad, Calif.), or may instead be an oxidized derivative, such as ChoXAsH-EDT$_2$ or HoXAsH-EDT$_2$. In addition, the biarsenical fluorophore can be a biarsenical derivative of other known fluorophores, including, but not limited to, the Alexa Fluor series described herein, such as, by way of example only, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 663 and Alexa Fluor® 660, available commercially from Molecular Probes (Eugene, Oreg.).

The biarsenical fluorophore can be present at a concentration of at least about 1 µM, 2 µM, 3 µM, 4 µM, 5 µM, 10 µM, 15 µM, 20 µM, 30 µM, 40 µM, 50 µM, 100 µM or more, and at a concentration of no more than about 500 µM, 400 µM, 300 µM, 200 µM, 100 µM, 90 µM, 80 µM, 70 µM, 60 µM, 50 µM, 40 µM, 30 µM, 20 µM, 15 µM, 10 µM, 5 µM, 4 µM, 3 µM, 2 µM or 1 µM.

The tag attached to a protein to which such fluorogenic dyes binds is a tetracysteine peptide motif, cys-cys-X$_n$-cys-cys (SEQ ID NO:1), wherein each X is any natural amino acid, non-natural amino acid or combination thereof, and n is an integer from 2-100. In certain embodiments, n is an integer from 2-90, while in other embodiments n is an integer from 2-80. In certain embodiments, n is an integer from 2-70, while in other embodiments n is an integer from 2-60. In certain embodiments, n is an integer from 2-50, while in other embodiments n is an integer from 2-40. In certain embodiments, n is an integer from 2-30, while in other embodiments n is an integer from 2-20. In certain embodiments, n is an integer from 2-10, while in other embodiments n is an integer from 2-5. The natural amino acids if such motifs include, but are not limited to, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine. In certain embodiments, the tetracysteine tag has the sequence CCPGCC (SEQ ID NO:2). In other embodiments a 12 amino acid peptide containing the tetracysteine motif is used including, but not limited to, the amino acid sequence, AGGCCPGCCGGG (SEQ ID NO:3). In addition, the protein can be labeled with a single tetracysteine tag or the protein can be labeled with a plurality of tetracysteine tags including, but not limited to, 2, 3, 4, 5, 6, 7, 8, 9, 10, 11, 12, 13, 14, 15, 16, 17, 18, 19 or 20 tetracysteine tags. Such tags may be separated from one another within the primary amino acid sequence of the protein or directly multimerized in tandem as concatemers.

In certain embodiments, the tetracysteine peptide has the sequence cys-cys-$X_n$-cys-X-cys-X (SEQ ID NO:4), wherein each X is any natural amino acid, non-natural amino acid or combination thereof, and n is an integer from 2-100. In certain embodiments, n is an integer from 2-90, while in other embodiments n is an integer from 2-80. In certain embodiments, n is an integer from 2-70, while in other embodiments n is an integer from 2-60. In certain embodiments, n is an integer from 2-50, while in other embodiments n is an integer from 2-40. In certain embodiments, n is an integer from 2-30, while in other embodiments n is an integer from 2-20. In certain embodiments, n is an integer from 2-10, while in other embodiments n is an integer from 2-5. The natural amino acids if such motifs include, but are not limited to, alanine, arginine, asparagine, aspartic acid, cyteine, glutamic acid, glutamine, glycine, histidine, isoleucine, leucine, lysine, methionine, phenylalanine, proline, serine, threonine, tryptophan, tyrosine and valine. In certain embodiments, the tetracysteine tag has the sequence CCGGKGNGGCGC (SEQ ID NO:5).

The tetracysteine peptide tag or tags can be recombinantly fused to the protein desired to be labeled, either at the N-terminus, C-terminus, or in frame within the protein sequence; expression vectors for creating tetracysteine-fused recombinant proteins may readily be constructed using techniques known to one of skill in the art. In certain embodiments the tetracysteine-tagged protein is expressed recombinantly in host cells including, but not limited to, in bacterial host cells, in fungal host cells, in insect cells, in plant cells, or in mammalian cells. Such bacterial host cells include, but are not limited to, gram negative and gram positive bacteria of any genus, including, by way of example only, *Escherichia* sp. (e.g., *E. coli*), *Klebsiella* sp., *Streptomyces* sp., *Streptococcus* sp., *Shigella* sp., *Staphylococcus* sp., *Erwinia* sp., *Klebsiella* sp., *Bacillus* sp. (e.g., *B. cereus, B. subtilis* and *B. megaterium*), *Serratia* sp., *Pseudomonas* sp. (e.g., *P. aeruginosa* and *P. syringae*) and *Salmonella* sp. (e.g., *S. typhi* and *S. typhimurium*). Suitable bacterial strains and serotypes suitable for the invention can include *E. coli* serotypes K, B, C, and W. A typical bacterial host is *E. coli* strain K-12. The fungal host cells include, by way of example only, *Saccharomyces cerevisiae* cells, while the mammalian cells include, by way of example only, including human cells. In such embodiments, the protein sample containing the protein of interest is a lysate of the host cells, that can be unpurified, partially purified, or substantially purified prior to labeling and analysis using the methods described herein.

In other embodiments, the tetracysteine-tagged protein is expressed in vitro, wherein the protein sample containing the protein of interest is the cell-free extract in which translation (and, optionally, transcription) is performed, or a partially purified or purified fraction thereof. In embodiments in which the extract permits coupled transcription and translation in a single cell-free extract, such as the *E. coli*-based ExpressWay or Expressway Plus systems (Invitrogen Corp., Carlsbad, Calif.), the sample is the cell-free extract in which transcription and translation commonly occur, or a fraction thereof. Alternatively, Gateway® Technology (Invitrogen Corp., Carlsbad, Calif.) is a universal cloning technology that can be used to express a gene of interest in *E. coli*.

The protein to be labeled using the biarsenical dyes described herein can be any protein having a tetracysteine motif. The protein to which the tetracysteine tag or tags is fused or conjugated can be any protein desired to be labeled, either naturally-occurring or nonnaturally occurring. Naturally-occurring proteins may have known biological function or not, and may be known to be expressed or only predicted from genomic sequence. The protein, if naturally-occurring, can be a complete protein or only a fragment thereof. The tetracysteine-tagged protein can thus be an animal protein, such as a human protein or non-human mammalian protein, a fungal protein, a bacterial protein, including eubacterial and archaebacterial protein, a plant protein, an insect protein or a viral protein.

In addition to the tetracysteine tag, other protein sequences can usefully be recombinantly appended to the proteins desired to be labeled. Among such additional protein sequences are linkers and/or short tags, usefully epitope tags, such as a FLAG tag, or a myc tag, or other sequences useful for purification, such as a polyhistidine (e.g., 6×his) tag.

Alternatively, the tetracysteine tag or tags can be chemically conjugated to proteins to be labeled using art-routine conjugation chemistries as described above.

The incubation temperatures used in the methods described herein can be room temperature, ambient temperature, or temperatures above room temperature, such as, by way of example only, at least about 26° C., 27° C., 28° C., 29° C., 30° C., 40° C., 50° C., 60° C., 70° C., 80° C., even as high as 90° C., 95° C., 96° C., 97°, 98° C., 99° C. or 100° C. The first incubation temperature and the second incubation temperature used in the methods described herein can be the same or different. In one embodiment, the first incubation temperature is between 20° C. and 80° C., more preferably between 25° C. and 30° C., even more preferably at ambient or room temperature. In one embodiment, the second incubation temperature is between 20° C. and 80° C., more preferably between 65° C. and 75° C., even more preferably at approximately 70° C. In another embodiment, the second incubation temperature is at ambient or room temperature.

The incubation times used in the methods described herein include, but are not limited to, for at least 30 seconds, at least 1 minute, at least 2 minutes, 3 minutes, 4 minutes, 5 minutes, 6 minutes, 7 minutes, 8 minutes, 9 minutes, 10 minutes, 15 minutes, 20 minutes, 30 minutes, 40 minutes, 50 minutes, at least 1 hour, or any range herein. The first incubation time and the second incubation time used in the methods described herein can be the same or different. In one embodiment, the first incubation time is 0 to 60 minutes, preferably 5 to 10 minutes, even more preferably 5 to 10 minutes at room temperature. In one embodiment, the second incubation time is 0 to 20 minutes, more preferably approximately 10 minutes, even more preferably approximately 10 minutes at approximately 70° C.

The optional sample reduction step of the methods described herein can be carried out at room temperature, ambient temperature, or at temperatures above room temperature, such as at a temperature of at least about 26° C., 27° C., 28° C., 29° C., 30° C., 40° C., 50° C., 60° C., 70° C., 80° C., even as high as 90° C., 95° C., 96° C., 97°, 98° C., 99° C. or 100° C. Such reduction steps can proceed for at least 30 seconds, at least 1 minute, at least 2 minutes, 3 minutes, 4 minutes, 5 minutes, 6 minutes, 7 minutes, 8 minutes, 9 minutes, 10 minutes, 15 minutes, 20 minutes, 30 minutes, 40 minutes, 50 minutes, or at least 1 hour.

In certain embodiments of the methods described herein a control protein or proteins may be labeled to monitor the effectiveness of labeling, either in a parallel reaction or, if readily resolvable from the protein desired to be labeled, by inclusion in the same reaction.

In certain embodiments of the methods described herein, the proteins of the labeled sample can usefully be resolved in parallel with a series of fluorescent molecular weight standards. Usefully, the standards are spectrally matched to at least one fluorophore used to label the proteins. Such spectral matching can be accomplished, for example, by using tetracysteine-tagged protein standards that are labeled in parallel with the same biarsenical fluorophore used to label the protein sample, or by using standards having a fluorescent moiety that is spectrally matched to the biarsenical fluorophore or other fluorophore used to label the sample proteins. In certain embodiments, protein standards, which in certain aspects are protein ladders, useful in the practice of the present invention include standards that include sets of recombinant proteins, recombinant protein fragment(s), as well as fusion proteins and multimers derived therefrom. Examples of standards useful in the practice of the present invention include the Benchmark™ family of protein standards (Invitrogen Corp., Carlsbad, Calif.) and Mark12™ Unstained Standard (Invitrogen, Carlsbad).

The methods and compositions described herein can also be used to quantitate the amount of fluorescently labeled protein present in a sample. In certain embodiments, the methods described herein further comprise quantitating the amount of fluorescence from the biarsenical fluorophore. In certain embodiments, the methods described herein further comprise quantitating the amount of fluorescence from the amine reactive fluorescent dye. In certain embodiments, the methods described herein further comprise quantitating the amount of fluorescence from the fluorescent moiety from the amine reactive fluorogenic reagent. The quantitation can be done without resolution of the proteins present in the protein sample or after the proteins have been partially or fully resolved, as by electrophoresis, such as PAGE, 2D-PAGE, or IEF or chromatography or combinations thereof.

The anionic surfactant used in the protein labeling methods described herein include, but are not limited to, alkyl benzenesulfonates, alkyl sulfonates, alkyl sulfosuccinates, alkyl phosphates, alkyl sulfates, alkyl carboxylates, alkyl ether benzenesulfonates, alkyl ether sulfonates, alkyl ether sulfosuccinates, alkyl ether phosphates, alkyl ether sulfates, alkyl ether carboxylates or mixture thereof. In certain embodiments of the methods described herein, the anionic surfactant is sodium dodecyl sulfate, lithium dodecyl sulfate, sodium lauryl ether sulfate, sodium oleate, sodium palmitate, sodium myristate, sodium stearate or mixture thereof. In certain embodiments, the anionic surfactant is sodium dodecyl sulfate, while, in other embodiments, the anionic surfactant is lithium dodecyl sulfate.

The concentration of the anionic surfactant used in the protein labeling methods described herein is in the range from 0.1% (w/v) to 10% (w/v). In certain embodiments, the concentration is in the range from 0.1% (w/v) to 5% (w/v). In other embodiments, the concentration is in the range from 0.5% (w/v) to 10% (w/v). In certain embodiments, the concentration is in the range from 0.5% (w/v) to 5% (w/v). In certain embodiments, the concentration is in the range from 1% (w/v) to 10% (w/v). In certain embodiments, the concentration is in the range from 1% (w/v) to 5% (w/v). In certain embodiments such concentrations are obtained by dilution of a stock solution of the anionic surfactant having a concentration in the range from 1% (w/v) to 20% (w/v). In certain embodiments the concentration of the stock solution is 10% (w/v). In certain embodiments the concentration of the stock solution is 5% (w/v). In certain embodiments the concentration of the stock solution is 2% (w/v).

The alkali cyanide used in the protein labeling methods described herein include, but are not limited to, lithium cyanide, potassium cyanide, sodium cyanide, rubidium cyanide cesium cyanide, or mixture thereof. In certain embodiments the alkali cyanide is potassium cyanide, while in other embodiments the alkali cyanide is sodium cyanide. In certain embodiments the alkali cyanide is lithium cyanide, while in other embodiments the alkali cyanide is cesium cyanide. Due to the toxic effects of alkali cyanide compounds, less toxic alternatives, such as acetone cyanohydrin or nitriles, may be preferable. For example, the LD50 value of sodium cyanide is 6.44, while the LD50 value for acetone cyanohydrin is 18.65, and the LD50 value for mandelonitrile is 116 (meaning that mandelonitrile is approximately 18 times less toxic than sodium cyanide).

The concentration of the alkali cyanide, acetone cyanohydrin or nitrile used in the protein labeling methods described herein is in the range from 50 nM to 200 mM. In certain embodiments, the concentration is in the range from 50 nM to 100 mM. In other embodiments, the concentration is in the range from 50 nM to 50 mM. In certain embodiments, the concentration is in the range from 50 nM to 25 mM. In certain embodiments, the concentration is in the range from 50 nM to 10 mM. In certain embodiments, the concentration is in the range from 50 nM to 5 mM. In certain embodiments, the concentration is in the range from 100 nM to 10 mM. In certain embodiments, the concentration is in the range from 100 nM to 5 mM. In certain embodiments, the concentration is in the range from 200 nM to 5 mM. In certain embodiments such concentrations are obtained by dilution of a stock solution of the fluorogenic reagents having a concentration in the range from 100 nM to 200 mM. In certain embodiments the concentration of the stock solution is 100 mM. In certain embodiments the concentration of the stock solution is 50 mM. In certain embodiments the concentration of the stock solution is 20 mM. In certain embodiments the concentration of the stock solution is 10 mM.

The concentration of the proteins or protein fragments labeled using the methods described herein is in the range from 0.01 mg/mL to 200 mg/mL. In certain embodiments, the concentration is in the range from 0.1 mg/mL to 100 mg/mL. In other embodiments, the concentration is in the range from 0.1 mg/mL to 50 mg/mL. In certain embodiments, the concentration is in the range from 0.1 mg/mL to 10 mg/mL. In certain embodiments, the concentration is in the range from 0.2 mg/mL to 100 mg/mL. In certain embodiments, the concentration is in the range from 0.2 mg/mL to 50 mg/mL. In certain embodiments, the concentration is in the range from 0.2 mg/mL to 10 mg/mL. In certain embodiments, the concentration is in the range from 0.3 mg/mL to 10 mg/mL. In certain embodiments, the concentration is in the range from 0.4 mg/mL to 10 mg/mL. In certain embodiments, the concentration is in the range from 0.5 mg/mL to 10 mg/mL.

The labeling methods for proteins or mixtures of proteins disclosed herein are rapid protein labeling methods that can be completed in less than 2 hours. In certain embodiments the method of protein labeling described herein is completed in less than 1 hour. In certain embodiments the method of protein labeling described herein is completed in less than 30 minutes. In certain embodiments the method of protein labeling described herein is completed in less than 20 minutes. In certain embodiments the method of protein labeling described herein is completed in less than 10 minutes. In certain embodiments the method of protein labeling described herein is completed in less than 5 minutes. In certain embodiments the method of protein labeling described herein is completed in less than 4 minutes. In certain embodiments the method of protein labeling described herein is completed in less than 3 minutes. In certain embodiments the method of protein labeling described herein is completed in less than 2 minutes. In certain embodiments the method of protein labeling described herein is completed in less than 1 minute.

First Buffers

The buffer (also referred to herein as the first buffer) used in the first step of the protein labeling methods described herein has a pH at ambient temperature from about pH 8 to about pH 10. In certain embodiments the first buffer has a pH at 25° C. from about pH 8 to about pH 10. In addition, the first buffer does not include buffer compounds or additives that have primary or secondary amine moieties. However, the methods described herein can tolerate low levels of amines that may be already present in the protein sample. By way of example only, the first buffer can include carbonates, bicarbonates, phosphates, borates, Bis-Tris propane, N,N-Bis(2-hydroxyethyl)glycine (Bicine), N-(1,1-Dimethyl-2-hydroxyethyl)-3-amino-2-hydroxypropanesulfonic acid (AMPSO) or combinations thereof.

The concentration of the first buffer used in the methods disclosed herein is from about 10 mM to about 1 M. In certain embodiments the concentration is between about 20 mM and about 500 mM, and in other embodiments the concentration is between about 50 mM and about 300 mM. In certain embodiments the concentration is between about 10 mM and about 500 Mm. In certain embodiments the concentration is between about 10 mM and about 400 mM. In certain embodiments the concentration is between about 10 mM and about 300 mM. In certain embodiments the concentration is between about 10 mM and about 200 mM. In certain embodiments the concentration is between about 10 mM and about 100 mM. In certain embodiments the concentration is between about 10 mM and about 50 mM.

Second Buffers

The buffer (also referred to herein as the second buffer) used in the second step of the protein labeling method described herein has a pH at ambient temperature between about pH 2 and about pH 8 and has a buffer capacity greater than the first buffer. In certain embodiments the second buffer has a pH at 25° C. between about pH 2 and about pH 8 and has a buffer capacity greater than the first buffer.

The second buffer used in the method disclosed herein may be any electrophoresis buffer, including but not limited to, zwitterionic buffers. The second buffer used in such methods contains at least one compound with a pKa at ambient temperature between about 2 and about 9. In certain embodiments the second buffer comprises a compound having a pKa between about 3 and about 8 at ambient temperature. In certain embodiments the second buffer comprises a compound having a pKa between about 4 and about 8 at ambient temperature. In certain embodiments the second buffer comprises a compound having a pKa between about 5 and about 8 at ambient temperature. In certain embodiments the second buffer comprises a compound having a pKa between about 6 and about 8 at ambient temperature. In certain embodiments the second buffer comprises a compound having a pKa between about 7 and about 8 at ambient temperature. In certain embodiments the second buffer comprises a compound having a pKa between about 6 and about 7 at ambient temperature. In certain embodiments, the second buffer used in such methods contains at least one compound with a pKa at 25° C. between about 2 and about 8. In certain embodiments the second buffer comprises a compound having a pKa between about 3 and about 8 at 25° C. In certain embodiments the second buffer comprises a compound having a pKa between about 4 and about 8 at 25° C. In certain embodiments the second buffer comprises a compound having a pKa between about 5 and about 8 at 25° C. In certain embodiments the second buffer comprises a compound having a pKa between about 6 and about 8 at 25° C. In certain embodiments the second buffer comprises a compound having a pKa between about 7 and about 8 at 25° C. In certain embodiments the second buffer comprises a compound having a pKa between about 6 and about 7 at 25° C.

The second buffers used in the methods disclosed herein include, but are not limited to, phosphate, succinate, citrate, maleate, cacodylate, N-(2-acetamido)iminodiacetic acid (ADA), 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl) methylamino)-2-hydroxypropanesulfonic acid (TAPSO), 3-(N,N-Bis[2-hydroxyethyl]amino)-2-hydroxypropanesulfonic acid (DIPSO), N-(2-Hydroxyethyl)piperazine-N'-(2-hydroxypropanesulfonic acid) (HEPPSO), N-(1,1-Dimethyl-2-hydroxyethyl)-3-amino-2-hydroxypropanesulfonic acid (AMPSO), bis[2-hydroxyethyl]iminotris[hydroxymethyl]methane (BisTris), or combinations thereof.

In certain embodiments, the second buffer can be selected from the group consisting of phosphate, glycine, citric acid, acetic acid, 2-(N-morpholino)-ethanesulfonic acid (MES), cacodylic acid, carbonic acid, bis[2-hydroxyethyl]iminotris[hydroxymethyl]methane (BisTris), piperazine-N, N'-2-ethanesulfonic acid (PIPES), N-(2-acetamido)-2-aminoethanesulfonic acid (ACES), Imidazole, N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), N-(2-Hydroxyethyl)piperazine-N'-(2-hydroxypropanesulfonic acid) (HEPPSO) and triethanolamine. In certain embodiments, the second buffer is bis[2-hydroxyethyl]iminotris[hydroxymethyl]methane (BisTris).

In certain embodiments, the second buffer is added to the initial reaction mixture containing the first buffer, fluorogenic reagent, an alkali cyanide (or alternatively acetone cyanohydrin or a nitrile such as mandelonitrile), and an anionic surfactant, thereby maintaining the pH (at ambient temperature) of the final mixture between about pH 5 and about pH 9. In certain embodiments the final mixture has a pH between 6 and 8 at ambient temperature. In certain embodiments the final mixture has a pH between 6 and 7 at ambient temperature. In certain embodiments the final mixture has a pH between 5 and 8 at 25° C. In certain embodiments the final mixture has a pH between 6 and 8 at 25° C. In certain embodiments the final mixture has a pH between 6 and 7 at 25° C.

The concentration of the second buffer used in the methods disclosed herein is from about 10 mM to about 1 M. In certain embodiments the concentration is between about 20 mM and about 500 mM, and in other embodiments the concentration is between about 50 mM and about 300 mM. In certain embodiments the concentration is between about 10 mM and about 500 Mm. In certain embodiments the concentration is between about 10 mM and about 400 mM. In certain embodiments the concentration is between about 10 mM and about 300 mM. In certain embodiments the concentration is between about 10 mM and about 200 mM. In certain embodiments the concentration is between about 10 mM and about 100 mM. In certain embodiments the concentration is between about 10 mM and about 50 mM.

Separation Methods

The chromatographic techniques used in the methods described herein to analyze proteins include, but are not limited to, liquid chromatography, high performance liquid chromatography, annular chromatography, size exclusion chromatography, ion exchange chromatography, affinity chromatography and immunoaffinity chromatography.

In certain embodiments the labeled proteins or mixtures of labeled proteins are not purified from unreacted fluorogenic reagent before being separated using electrophoretic techniques, chromatographic techniques, or combinations thereof. In other embodiments the labeled proteins or mixtures of labeled proteins are purified from unreacted fluorogenic reagent before being separated using electrophoretic techniques, chromatographic techniques, or combinations thereof. Other embodiments include precipitating a sample containing a protein or mixture of proteins followed by reconstituting the sample in the labeling solutions described herein. Alternatively, or in addition to this precipitation step, the proteins or mixture of proteins may be alkylated prior to labeling in order to eliminate the negative impact of any reducing agents on labeling.

The electrophoretic techniques used in the methods described herein to analyze the labeled proteins include, but are not limited to, capillary electrophoresis (CE), capillary zone electrophoresis (CZE), capillary gel electrophoresis (CGE), slab gel electrophoresis, isoelectric focusing gel electrophoresis, isoelectric focusing electrophoresis and 2D electrophoresis techniques. The processes by which the proteins separate include, but are not limited to separation by size, separation by charge, or separation by a combination of size and charge. In certain embodiments, the fluorescently labeled proteins are separated electrophoretically using a slab gel contained within a disposable cassette as described herein.

For size fractionation by gel electrophoresis, the labeled proteins can be resolved by electrophoresis in slab gels including, but not limited to, 10% Bis-Tris gels, 4-12% Bis-Tris gels, or 12% Bis-Tris Gels, such as, by way of example only, NuPAGE® Novex® Bis-Tris gels (Invitrogen Corp., Carlsbad, Calif.) run with either 2-(N-morpholino)-ethanesulfonic acid (MES) or 3-(N-morpholino)-propane-sulfonic acid (MOPS) buffer. In certain embodiments, the labeled proteins can be resolved in Tris-acetate (TA) gels, including, but not limited to, 7% or 3-8% gradient Tris-acetate gels, such as, by way of example only, NuPAGE® Novex® Tris acetate gels (Invitrogen Corp., Carlsbad, Calif.). In certain other embodiments, the labeled proteins can be resolved in Tris-glycine (TG) gels, including, but not limited to, 4% TG gels, 6% TG gels, 8% TG gels, 10% TG gels, 12% TG gels, 14% TG gels, 16% TG gels, and 18% TG gels. In certain other embodiments, the labeled proteins can be resolved in gradient Tris-glycine (TG) gels, including, but not limited to, TG gels having gradients such as 4-12%, 4-20%, 8-16%, 10-20%, such as, by way of example only, the TG gels available from Invitrogen Corp. (Carlsbad, Calif.). In further embodiments, the labeled proteins can be resolved in Tricine gels, such as 10% Tricine gels, 16% Tricine gels, and 10-20% gradient Tricine gels. In still further embodiments, the labeled proteins can be resolved in standard Laemmli gels.

The gel-based electrophoretic embodiments of the methods of the present invention can be carried out in gels of any suitable physical format, for example in standard-sized slab gels, minigel slab gels, strips, gels in capillaries, in gels designed for use with microtiter plates and in other high throughput applications.

In certain embodiments up to 96 protein samples labeled according to the methods described herein can be resolved simultaneously in an E-PAGE™ 96 gel system (Invitrogen Corp., Carlsbad, Calif.). The E-PAGE™ 96 gels are self-contained, pre-cast gels that include a gel matrix and electrodes packaged inside a disposable, UV-transparent cassette. Each E-PAGE™ 96 gel contains 96 sample lanes and 8 marker lanes in a staggered well format.

For separation based on isoelectric point, the labeled proteins can be resolved using isoelectric focusing (IEF), either as a single separation step or as a step preliminary to size fractionation using methods, systems and gels described above including, but not limited to, as the first step in 2D-PAGE. In certain embodiments, the labeled proteins can be resolved using solution phase isoelectric focusing. In certain embodiments, the labeled proteins can be resolved using ZOOM® IEF Fractionator, a solution phase isoelectric focusing apparatus from Invitrogen Corp. (Carlsbad, Calif.). In such embodiments, the proteins can be labeled, either before or after fractionation with solution phase IEF, using a fluorogenic reagent and the methods described herein. In other embodiments, the labeled proteins can be resolved using gel-based isoelectric focusing, either in slab gels, in tube gels, or, in immobilized pH gradient (IPG) strips.

The electrophoretic separation of the labeled proteins can be achieved using constant voltage, pulsed voltage, constant current, pulsed current, constant power or pulsed power. Subsequently, the electric field (V/cm) used in the methods disclosed herein can be constant or pulsed. It is understood that the magnitude of the applied voltage, applied current or applied power to achieve the electric fields ranges provided below will vary depending on the dimensions of the electrophoresis apparatus (capillary or slab gel) and buffer conductivity. By way of example only, the applied voltage can range from 5V to 10,000V. In certain embodiments the applied voltage can range from 5V to 2,000V, and in certain embodiments the applied voltage can range from 5V to 1,000V, 5V to 500V, 5V to 250V, or 5V to 100V. By way of example only, the applied current can range from 5 mA to 400 mA, and in certain embodiments the applied current can range from 5 mA to 200 mA, 5 mA to 100 mA, 5 mA to 50 mA, or 5 mA to 25 mA. In one embodiment the applied current can be 60 mA. By way of example only, the applied power can range from 5 mA to 400 mA, and in certain embodiments the applied current can range from 25 mW to 400 W, 25 mW to 100 W, 25 mW to 50 W, or 25 mW to 25 W. In one embodiment the applied current can be 4.5 W. In addition the polarity of the applied voltage (constant or pulsed) can be positive or negative, and the polarity of the applied current (constant or pulsed) can be positive or negative.

In certain embodiments the magnitude of the constant electric field applied is between 1 V/cm and 100 V/cm. In certain embodiments the magnitude of the constant electric field applied is between 1 V/cm and 50 V/cm. In certain embodiments the magnitude of the constant electric field applied is between 1 V/cm and 25 V/cm. In certain embodiments the magnitude of the constant electric field applied is between 1 V/cm and 15 V/cm. In certain embodiments the magnitude of the constant electric field applied is between 1 V/cm and 10 V/cm.

The profile of the pulsed electric field can be a square wave, triangular wave or sine wave, and such profiles can be symmetric or asymmetric. The pulsed electric field is applied to a constant baseline electric field and the magnitude of this baseline electric field is from 0 V/cm to 100 V/cm. In certain embodiments the magnitude of this baseline electric field is from 0 V/cm to 50 V/cm. the magnitude of this baseline electric field is from 0 V/cm to 25 V/cm. the magnitude of this baseline electric field is from 0 V/cm to 10 V/cm. In certain embodiments the magnitude of the pulsed electric field applied in addition to the baseline electric field is between 1 V/cm and 100 V/cm. In certain embodiments the magnitude of the pulsed electric field applied in addition to the baseline electric field is between 1 V/cm and 50 V/cm. In certain embodiments the magnitude of the pulsed electric field applied in addition to the baseline electric field is between 1 V/cm and 25 V/cm. In certain embodiments the magnitude of the pulsed electric field applied in addition to the baseline electric field is between 1 V/cm and 10 V/cm.

For pulsed electric fields which are symmetric square waves the time the pulsed electric field is applied in addition to the baseline electric field (ON) is the same as the time that the pulsed electric field is not applied (OFF). In certain embodiments the ON and OFF times are between 1 ms and 60 seconds. For pulsed electric fields which are asymmetric square wave pulsed electric fields have the time the pulsed electric field is applied in addition to the baseline electric field (ON) is not the same as the time that the pulsed electric field is not applied (OFF). In certain embodiments the ON time is independently between 1 ms and 60 seconds, and the OFF time is independently between 1 ms and 60 seconds.

For pulsed electric fields which are symmetric triangular waves the voltage ramp rate (V/s) up to the maximum electric field applied is the same as the time that the voltage ramp rate (V/s) down to the baseline electric field applied. In certain embodiments the voltage ramp up and the voltage ramp down are between 10 mV/s and 100 V/s. For pulsed electric fields which are asymmetric triangular waves the voltage ramp rate (V/s) up to the maximum electric field applied is not the same as the time that the voltage ramp rate (V/s) down to the baseline electric field applied. In certain embodiments the voltage ramp up is independently between 10 mV/s and 100 V/s and the voltage ramp down is independently between 10 mV/s and 100 V/s.

For pulsed electric fields which are symmetric sine waves the period and frequency are constant, and the minimum electric field of the sine wave is the same as the baseline electric field applied. For pulsed electric fields which are asymmetric sine waves the period and frequency are modulated, and the minimum electric field of the sine wave is the same as the baseline electric field applied.

In certain embodiments, the electric field is applied using an E-Gel® Powerbase™ (Invitrogen Carlsbad), E-Gel® i-Base™ (Invitrogen Carlsbad) and an E-Base® (Invitrogen Carlsbad).

In certain embodiments the labeled proteins or mixtures of labeled proteins are separated using slab gel electrophoretic techniques. In such embodiments the first buffer used in the labeling methods described herein also includes a sugar, a sugar alcohol, or combinations thereof. In other embodiments the second buffer used in the labeling methods described herein also includes a sugar, a sugar alcohol, or combinations thereof. Alternatively, in other embodiments a sugar, a sugar alcohol, or combinations thereof is added to the final reaction mixture. In certain embodiments the sugar added to the first buffer is sucrose. In other embodiments the sugar alcohol added to the first buffer is glycerol. In certain embodiments the sugar added to the second buffer is sucrose. In other embodiments the sugar alcohol added to the second buffer is glycerol. In certain embodiments the sugar added to the final reaction mixture is sucrose. In other embodiments the sugar alcohol added to the final reaction mixture is glycerol.

The concentration of the sugar or sugar alcohol used in the protein labeling methods described herein is from about 1% (w/v) to about 30% (w/v). In certain embodiments, the concentration of the sugar or sugar alcohol used in the protein labeling methods described herein is from about 1% (w/v) to about 25% (w/v). In certain embodiments the concentration is from about 1% (w/v) to about 20% (w/v), and in other embodiments the concentration is from about 1% (w/v) to about 15% (w/v). In certain embodiments the concentration is from about 1% (w/v) to about 10% (w/v), and in other embodiments the concentration is from about 5% (w/v) to about 25% (w/v). In other embodiments the concentration is from about 5% (w/v) to about 20% (w/v).

The labeled proteins or mixture of proteins may be treated with a reducing agent before the separation step. Such reducing agents include, but are not limited to, dithiothreitol (DTT), 2-mercaptoethanol (also known as β-mercaptoethanol), sodium bisulfite, thioglycolic acid, mercaptoethanesulfonic acid, glutathione and trialkylphosphine compounds or combinations thereof. Such trialkylphosphine compounds include, but are not limited to, tri-n-butylphosphine (TBP) or tris[2-carboxyethyl] phosphine (TCEP). A reducing agent, or a combination of reducing agents, may be added to the first buffer prior to the addition of the second buffer, or alternatively a reducing agent, or combination of reducing agents may be added to the second buffer prior to addition of the second buffer to the first buffer.

The concentration of the reducing agents used in the methods described herein include, but are not limited to, at least about 10 μM, at least about 100 μM, at least about 1 mM, at least about 2 mM, at least about 2.5 mM, at least about 3 mM, at least about 3.75 mM, a at least about 4 mM, at least about 5 mM, at least about 10 mM, at least about 15 mM, at least about 20 mM, at least about 25 mM, at least about 30 mM, at least about 35 mM, at least about 40 mM, at least about 45 mM, at least about 50 mM, at least about 55 mM, at least about 60 mM, at least about 65 mM, at least about 70 mM, at least about 75 mM, at least about 80 mM, at least about 85 mM, at least about 90 mM, at least about 95 mM, at least about 100 mM, at least about 200 mM, at least about 350 mM, or at least about 500 mM. The concentration of the reducing agents used in the methods described herein include, but are not limited to, 10 μM, 100

μM, 1 mM, 2 mM, 2.5 mM, 3 mM, 3.75 mM, 4 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 200 mM, 350 mM, or 500 mM.

In certain embodiments, the electrophoresis gel used in the methods disclosed herein comprise acrylamide, including by way for example only, acrylamide at a concentration from about 2.5% to about 30%, or from about 5% to about 20%. In certain embodiments, such polyacrylamide electrophoresis gel comprises 1% to 10% crosslinker, including but not limited to, bisacrylamide. In certain embodiments, the electrophoresis gel used in the methods disclosed herein comprises agarose, including by way for example only, agarose at concentration from about 0.1% to about 5%, or from about 0.5% to about 4%, or from about 1% to about 3%. In certain embodiments, the electrophoresis gel used in the methods disclosed herein comprises acrylamide and agarose, including by way for example only, electrophoresis gels comprising from about 2.5% to about 30% acrylamide and from about 0.1% to about 5% agarose, or from about 5% to about 20% acrylamide and from about 0.2% to about 2.5% agarose. In certain embodiments, such polyacrylamide/agarose electrophoresis gel comprise 1% to 10% crosslinker, including but not limited to, bisacrylamide.

In certain embodiments of the methods disclosed herein the electrophoresis gel in the electrophoresis cassette is a gradient gel. In other embodiments of the methods disclosed herein the electrophoresis gel in the electrophoresis cassette is a highly crosslinked gel.

In certain embodiments, the electrophoresis cassette and electrophoresis gel used in the methods disclosed herein are the E-PAGE™ cassettes/gels (Invitrogen, Carlsbad) and the E-Gel® cassettes/gels (Invitrogen Carlsbad). In certain embodiments, the E-PAGE™ (Invitrogen, Carlsbad) cassettes/gels have two rows of wells, wherein one row of wells are loading wells and the other row of wells are collection wells. In other embodiments, the E-Gel® cassettes/gels (Invitrogen Carlsbad) had two rows of wells, have two rows of wells, wherein one row of wells are loading wells and the other row of wells are collection wells. In certain embodiments, a 0.8% E-Gel® (Invitrogen Carlsbad) cassettes/gels with two rows of wells, one row of loading wells and one row of collection wells, are used. In other embodiments, a 2% E-Gel® cassettes/gels (Invitrogen Carlsbad) had two rows of wells, one row of loading wells and one row of collection wells, are used.

The electrophoresis gels of the methods disclosed herein can comprise any material which forms a gel including, but not limited to, synthetic polymers, natural polymers and combinations thereof. Examples of such synthetic polymers include, but are not limited to, linear polyacrylamide, cross-linked polyacrylamide, polyvinylpyrrolidone and combinations thereof. Examples of such natural polymers include, but are not limited to, polysaccharides such as agarose, carrageenan, and chitosan. In certain embodiments the gels can comprise agarose, polyacrylamide, or combinations of agarose and polyacrylamide. In certain embodiments the gels are polyacrylamide gels, while in other embodiments the gels are agarose gels. In still other embodiments the gels comprise both acrylamide and agarose. In certain embodiments the gels comprise crosslinked polyacrylamide, while in other embodiments the gels comprise non-crosslinked polyacrylamide, also referred to herein as linear polyacrylamide.

The gels used in the methods described herein can be denaturing gels, wherein the gels include a detergent(s), chaotropic agent(s) or combinations thereof. Chaotropic agents include, but are not limited to, sodium trifluoroacetate, sodium perchlorate, sodium iodide, urea, guanidinium chloride and guanidine isothiocyanate. Denaturing detergents include, but are not limited to, sodium dodecyl sulfate (SDS) and lithium dodecyl sulfate (LDS). The denaturing gels used in the methods described herein include, but not limited to, SDS polyacrylamide gels and SDS linear polyacrylamide.

In addition, the gels used in the methods described herein can be native gels, also referred to herein as non-denaturing gels. Native or non-denaturing gels used in the methods disclosed herein are run without denaturing agents such as, for example, protein-denaturing detergents or chaotropes in the gel or in the running buffer(s). In some embodiments, the electrophoresis gel used in the methods described herein is a gradient gel.

The electrophoresis gels use in the methods described herein can be run horizontally or vertically.

The electrophoresis gels used in the methods disclosed herein include a body of separating gel and optionally include a stacking gel. The separating gels and stacking gels can be comprised of the same material that forms a gel, or the separating gels and stacking gels can be comprised of different material that forms a gel. In certain embodiments of the separating and stacking gels are polyacrylamide gels, where the stacking gel also includes linear polyacrylamide. In other embodiments of the separating and stacking gels are polyacrylamide gels, where the separating gel also includes linear polyacrylamide. In certain embodiments of the separating and stacking gels are polyacrylamide gels, where both the separating gel and the stacking gel include linear polyacrylamide. The electrophoresis gels used in methods disclosed herein can comprise a stacking gel and a separating gel, in which linear acrylamide is present only in the stacking gel and is not present in the separating gel. In certain embodiments, such stacking gels and separating gels both comprise polyacrylamide, but only the stacking gel comprises linear acrylamide.

The polyacrylamide gels used in methods disclosed herein are made using solutions of "acrylamide" that are mixtures of monomeric acrylamide and bisacrylamide. The polymerization of acrylamide and bisacrylamide uses polymerization initiators, and if needed catalysts, to produce cross-linked polyacrylamide gel. The ratios of monomeric acrylamide to bisacrylamide used in the mixtures to make the polyacrylamide gels of the compositions, gel cassettes and methods disclosed herein range from about 15:1 to about 50:1. By way of example only, the (monomeric) acrylamide:bisacrylamide ratio in such polyacrylamide gels can be 15:1, 19:1, 24:1, 29:1, 37.5:1, 40:1, 45:1 and 50:1. In certain embodiments disclosed herein, the ratios of (monomeric) acrylamide to bisacrylamide for the analysis of proteins and protein complexes, are in the range from about 19:1 to about 45:1.

In certain embodiments of the electrophoresis gels used in the methods disclosed herein, the stacking gel comprises polyacrylamide made using the mixtures of acrylamide and bisacrylamide as described above. In certain embodiments, the stacking gel is made with lower acrylamide concentration than that used to make the separating gel. By way of example only, stacking gels can have (w/v) acrylamide concentrations ranging from about 2% to about 8%, from about 2.5% to about 7.5% acrylamide, from about 3% to about 7% acrylamide, from about 3.5% to about 6.5% acrylamide, from about 4% to about 6% acrylamide, from about 4.5% to about 5.5% acrylamide, or from about 2.5% to about 6% acrylamide. By way of example only, stacking gels can have (w/v) acrylamide concentrations ranging from 2% to 8%, from 2.5% to 7.5% acrylamide, from 3% to 7% acrylamide, from 3.5% to 6.5% acrylamide, from t 4% to 6% acrylamide, from 4.5% to 5.5% acrylamide, or from 2.5% to 6% acrylamide.

In certain embodiments, the separating gels and stacking gels (individually or together) of the electrophoresis gels used in the methods disclosed herein include linear polyacrylamide. In other embodiments, the polyacrylamide separating gels and polyacrylamide stacking gels (individually or together) of the electrophoresis gels used in the methods disclosed herein include linear polyacrylamide. The (weight/volume) concentrations of the linear acrylamide included in such gels can range from about 0.005% to about 1%, 0.005% to about 0.75%, 0.005% to about 0.5%, 0.005% to about 0.1%, 0.01% to about 1%, 0.01% to about 0.75%, 0.01% to about 0.5%, 0.01% to about 0.1%, 0.02% to about 1%, 0.02% to about 0.75%, 0.02% to about 0.5%, 0.02% to about 0.2%, or 0.02% to about 0.1%. In illustrative embodiments, the (weight/volume) concentrations of the linear acrylamide included in such gels can range from 0.005% to 1%, 0.005% to 0.75%, 0.005% to 0.5%, 0.005% to 0.1%, 0.01% to 1%, 0.01% to 0.75%, 0.01% to 0.5%, 0.01% to 0.1%, 0.02% to 1%, 0.02% to 0.75%, 0.02% to 0.5%, 0.02% to 0.2%, or 0.02% to 0.1%.

In addition, the molecular weight of the linear acrylamide included in such gels can range from about 1,000 Daltons to about 6,000,000 Daltons, from about 1,000 Daltons to about 5,000,000 Daltons, from about 1,000 Daltons to about 2,000,000 Daltons, from about 1,000 Daltons to about 1,000,000 Daltons, from about 1,000 Daltons to about 750,000 Daltons, from about 1,000 Daltons to about 500,000 Daltons, from about 1,000 Daltons to about 300,000 Daltons, from about 1,000 Daltons to about 200,000 Daltons, from about 1,000 Daltons to about 100,000 Daltons, from about 1,000 Daltons to about 50,000 Daltons, from about 1,000 Daltons to about 25,000 Daltons, or from about 1,000 Daltons to about 10,000 Daltons. In addition, the molecular weight of the linear acrylamide included in such gels can range from 1,000 Daltons to 6,000,000 Daltons, from 1,000 Daltons to 5,000,000 Daltons, from 1,000 Daltons to 2,000,000 Daltons, from 1,000 Daltons to 1,000,000 Daltons, from 1,000 Daltons to 750,000 Daltons, from 1,000 Daltons to 500,000 Daltons, from 1,000 Daltons to 300,000 Daltons, from 1,000 Daltons to 200,000 Daltons, from 1,000 Daltons to 100,000 Daltons, from 1,000 Daltons to 50,000 Daltons, from 1,000 Daltons to 25,000 Daltons, or from 1,000 Daltons to 10,000 Daltons.

In some embodiments, the electrophoresis gel used in the methods described herein is a gradient gel in which the concentration of the polymer varies through the gel, generally from low concentration at the top of the gel body to high concentration at the bottom of the gel body. The concentration range of the polymer in such gradient separating gels depends on the application, and in particular the size of the proteins to be separated. In certain embodiments the electrophoresis gel of the methods disclosed herein can be gradient polyacrylamide gels having a concentration gradient with (w/v) acrylamide concentrations ranging from about 2% to about 30%, from about 2.5% to 25%, from about 3% to about 20%, from about 3% to about 8%, from about 4% to about 16%, from about 3% to about 12%, from about 4% to about 20%, or from about 5% to about 20%.

The electrophoresis gels used in the methods disclosed herein can include both a gradient separating gel and a stacking gel, wherein the concentration of the stacking gel polymer is equal to or less than the lowest concentration of polymer used in the gradient separating gel. In certain embodiments, the electrophoresis gels includes both a polyacrylamide gradient separating gel and a polyacrylamide stacking gel, wherein the concentration of the acrylamide in the stacking gel is equal to or less than the lowest concentration of acrylamide used in the gradient separating gel. In other embodiments, the electrophoresis gels includes both a polyacrylamide gradient separating gel and a polyacrylamide stacking gel, wherein the concentration of the acrylamide in the stacking gel is equal to or less than the lowest concentration of acrylamide used in the gradient separating gel, and the stacking gel includes linear polyacrylamide at a (w/v) concentration of from about 0.005% to about 1%, 0.005% to about 0.75%, 0.005% to about 0.5%, 0.005% to about 0.1%, 0.01% to about 1%, 0.01% to about 0.75%, 0.01% to about 0.5%, 0.01% to about 0.1%, 0.02% to about 1%, 0.02% to about 0.75%, 0.02% to about 0.5%, 0.02% to about 0.2% or 0.02% to about 0.1%. In other embodiments, the electrophoresis gels includes both a polyacrylamide gradient separating gel and a polyacrylamide stacking gel, wherein the concentration of the acrylamide in the stacking gel is equal to or less than the lowest concentration of acrylamide used in the gradient separating gel, and the stacking gel includes linear polyacrylamide at a (w/v) concentration of from 0.005% to 1%, 0.005% to 0.75%, 0.005% to 0.5%, 0.005% to 0.1%, 0.01% to 1%, 0.01% to 0.75%, 0.01% to 0.5%, 0.01% to 0.1%, 0.02% to 1%, 0.02% to 0.75%, 0.02% to 0.5%, 0.02% to 0.2% or 0.02% to 0.1%. In another embodiment, an electrophoresis gels used in the methods disclosed herein can include a slab gradient polyacrylamide separating gel comprising a polyacrylamide concentration of 4%-16%, and a polyacrylamide stacking gel with a concentration of 3% polyacrylamide plus 0.05% (weight/volume) of linear polyacrylamide.

The gradient separating gels of the electrophoresis gels used in the compositions, gel cassettes and methods disclosed herein can also include linear acrylamide present in a (w/v) concentration of from about 0.005% to about 1%, 0.005% to about 0.75%, 0.005% to about 0.5%, 0.005% to about 0.1%, 0.01% to about 1%, 0.01% to about 0.75%, 0.01% to about 0.5%, 0.01% to about 0.1%, 0.02% to about 1%, 0.02% to about 0.75%, 0.02% to about 0.5%, 0.02% to about 0.1%, or 0.02% to about 0.1%. In certain embodiments such gradient separating gels include linear acrylamide present in a (w/v) concentration of from 0.005% to 1%, 0.005% to 0.75%, 0.005% to 0.5%, 0.005% to 0.1%, 0.01% to 1%, 0.01% to 0.75%, 0.01% to 0.5%, 0.01% to 0.1%, 0.02% to 1%, 0.02% to 0.75%, 0.02% to 0.5%, 0.02% to 0.1%, or 0.02% to 0.1%. In certain embodiments, such gradient separating gels are polyacrylamide gradient separating gels having a concentration gradient with (w/v) acrylamide concentrations ranging from about 2% to about 30%, from about 2.5% to about 25%, from about 3% to about 20%, from about 3% to about 8%, from about 4% to about 16%, from about 3% to about 12%, from about 4% to about 20%, or from about 5% to about 20%. In certain embodiments, such gradient separating gels are polyacrylamide gradient separating gels having a concentration gradient with (w/v) acrylamide concentrations ranging from 2% to 30%, from 2.5% to 25%, from 3% to 20%, from 3% to 8%, from 4% to 16%, from 3% to 12%, from 4% to 20%, or from 5% to 20%.

The electrophoresis gels used in methods disclosed herein can include both separating gels and stacking gels that are denaturing gels. In certain embodiments such denaturing separating gels and stacking gels comprise linear polyacrylamide, while in other embodiments such denaturing separating gels and stacking gels are polyacrylamide separating gels and stacking gels, wherein the stacking gel comprises linear polyacrylamide. In other embodiments such denaturing separating gels and stacking gels are polyacrylamide separating gels and stacking gels that comprise linear polyacrylamide. In other embodiments, the electrophoresis gels used in methods disclosed herein are denaturing polyacrylamide gels that do not comprise a stacking gel.

The gels used in the separation step of methods described herein include a gel buffer or buffers that can be any electrophoresis buffer, including, but not limited to, zwitterionic buffers. In certain embodiments the gel buffer has a pH between 5 and 9 at ambient temperature. In certain embodiments the gel buffer has a pH between 6 and 8.5 at ambient temperature. In certain embodiments the gel buffer has a pH between 6 and 8 at ambient temperature. In certain embodiments the gel buffer has a pH between 6 and 7 at ambient temperature. In certain embodiments the gel buffer has a pH between 7 and 8 at ambient temperature. In certain embodiments the gel buffer has a pH between 5 and 9 at 25° C. In certain embodiments the gel buffer has a pH between 6 and 8.5 at 25° C. In certain embodiments the gel buffer has a pH between 6 and 8 at 25° C. In certain embodiments the gel buffer has a pH between 7 and 8 at 25° C. In certain embodiments the gel buffer has a pH between 6 and 7 at 25° C.

In certain embodiments the buffer or buffers, including the gel buffer or buffers, used in the separation step of methods described herein comprises a compound having a pKa between about 5 and about 8.5 at ambient temperature. In certain embodiments such buffers comprise a compound having a pKa between about 6 and about 8.5 at ambient temperature. In certain embodiments such buffers comprise a compound having a pKa between about 6 and about 8 at ambient temperature. In certain embodiments such buffers comprise a compound having a pKa between about 6 and about 7 at ambient temperature. In certain embodiments such buffers comprise a compound having a pKa between about 7 and about 8 at ambient temperature. In certain embodiments such buffers comprise a compound having a pKa between about 5 and about 8.5 at 25° C. In certain embodiments such buffers comprise a compound having a pKa between about 6 and about 8.5 at 25° C. In certain embodiments such buffers comprise a compound having a pKa between about 6 and about 8 at 25° C. In certain embodiments such buffers comprise a compound having a pKa between about 6 and about 7 at 25° C. In certain embodiments such buffers comprise a compound having a pKa between about 7 and about 8 at 25° C.

The buffer or buffers, including the gel buffer or buffers, used in the separation step of methods described herein include, but are not limited to, succinate, citrate, borate, maleate, cacodylate, N-(2-Acetamido)iminodiacetic acid (ADA), 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl) methylamino)-2-hydroxypropanesulfonic acid (TAPSO), 3-(N,N-Bis[2-hydroxyethyl] amino)-2-hydroxypropanesulfonic acid (DIPSO), N-(2-Hydroxyethyl)piperazine-N'-(2-hydroxypropanesulfonic acid) (HEPPSO), 4-(2-Hydroxyethyl)-1-piperazinepropanesulfonic acid (EPPS), N-[Tris(hydroxymethyl)methyl]glycine (Tricine), N,N-Bis(2-hydroxyethyl)glycine (Bicine), (2-Hydroxy-1,1-bis(hydroxymethylethyl)amino]-1-propanesulfonic acid (TAPS), N-(1,1-Dimethyl-2-hydroxyethyl)-3-amino-2-hydroxypropanesulfonic acid (AMPSO), tris (hydroxy methyl) amino-methane (Tris), TRIS-Acetate-EDTA (TAE), glycine, bis[2-hydroxyethyl]iminotris[hydroxymethyl]methane (BisTris), or combinations thereof. In addition, such gel buffers can include ethylene diamine tetraacetic acid (EDTA).

The concentration of the buffer or buffers used in methods described herein can be from about 10 mM to about 1.5 M. In certain embodiments the concentration can be between about 10 mM and about 1 M. In certain embodiments the concentration can be between about 20 mM and about 500 mM, and in other embodiments the concentration is between about 50 mM and about 300 mM. In certain embodiments the concentration can be between about 10 mM and about 200 mM, and in other embodiments the concentration is between about 10 mM and about 500 mM. In certain embodiments the concentration can be between about 50 mM and about 200 mM, and in other embodiments the concentration is between about 50 mM and about 500 mM. In certain embodiments the concentration can be between about 5 mM and about 200 mM, and in other embodiments the concentration is between about 5 mM and about 500 mM. In certain embodiments the concentration can be between about 5 mM and about 1 M. In certain embodiments, the concentration of the buffer or buffers used in the methods described herein can be from 10 mM to 1.5 M. In certain embodiments the concentration can be between 10 mM and 1 M. In certain embodiments the concentration can be between 20 mM and 500 mM, and in other embodiments the concentration is between 50 mM and 300 mM. In certain embodiments the concentration can be between 10 mM and 200 mM, and in other embodiments the concentration is between 10 mM and 500 mM. In certain embodiments the concentration can be between 50 mM and 200 mM, and in other embodiments the concentration is between 50 mM and 500 mM. In certain embodiments the concentration can be between 5 mM and 200 mM, and in other embodiments the concentration is between 5 mM and 500 mM. In certain embodiments the concentration can be between 5 mM and 1 M.

Visualization

The separation of the labeled proteins can be monitored or otherwise visualized during or after the separation process. Any detection system known to the skilled artisan for use in electrophoretic or chromatographic techniques can be used in the methods described herein. By way of example only, laser induced fluorescence detection systems, imaging systems, CCD based systems, absorbance based system, systems utilizing PMT's, and mass spectrometry based detection.

Visualization of the sample bands in an electrophoresis gel can be achieved by illuminating the electrophoresis gel with light of appropriate wavelength(s) to allow observation of dyes, stains or other indicators associated with the sample bands. The electrophoresis gel may be visualized by itself or the gel may be within an electrophoresis cassette or within a capillary.

The light used for visualization can be monochromatic or polychromatic. By way of example only, polychromatic light can be white light, UV light or infra-red light, while monochromatic light can be achieved using lasers or Light Emitting Diodes (LED's), or by specific spectral filtering of sources such as white light, UV light or infra-red light. It would be understood that the desired wavelength of such monochromatic light depends on the specific spectral characteristics of the dye or stain used, and the skilled artisan will know the methods to obtain such monochromatic light.

Visualization can be performed in a stand alone "light box" in which an electrophoresis gel or an electrophoresis cassette containing a gel is placed during or after electrophoretic separation of the fluorescently labeled proteins. In such "light boxes" when the electrophoresis gel, or electrophoresis cassette containing a gel, is placed during electrophoretic separation the visualization occurs either continuously or intermittently. Alternatively the gel is visualized after the separation. In such light boxes the electrophoresis cassette can be illuminated from above or below. Monitoring can be achieved using a CCD camera or a video camera, or by direct observation of the user. In other embodiments of such visualization methods an electrophoresis/monitoring apparatus is used in which the monitoring means (CCD camera or a video camera, or by direct observation) and the means for application of the electric field or fields are combined into one apparatus. In addition, in other embodiments a means for cooling the electrophoresis cassette during the electrophoresis is incorporate. Such cooling can be achieved by a flow of cooled gas, (by way of example, liquid nitrogen), a fan or a Peltier cooler.

In certain embodiments visualization is achieved using a Dark Reader® (Clare Chemicals, Dolores) or a Safe Imager™ (Invitrogen, Carlsbad). In certain embodiments, visualization is achieved using an E-Gel® Powerbase™ (Invitrogen Carlsbad), in which the electrophoresis cassette containing the electrophoresis gel is connected to, placed over a Dark Reader® (Clare Chemicals, Dolores). In certain embodiments, visualization is achieved using an E-Gel® Powerbase™ (Invitrogen Carlsbad), in which an E-PAGE™ or an E-Gel® cassette (Invitrogen Carlsbad) is connected to, placed over a Dark Reader® (Clare Chemicals, Dolores). In certain embodiments, visualization is achieved using an E-Gel® Powerbase™ (Invitrogen Carlsbad), in which the electrophoresis cassette containing the electrophoresis gel is connected to, placed over a Safe Imager™ (Invitrogen, Carlsbad). In certain embodiments, visualization is achieved using an E-Gel® Powerbase™ (Invitrogen Carlsbad), in which an E-PAGE™ or an E-Gel® cassette (Invitrogen Carlsbad) is connected to, placed over a Safe Imager™ (Invitrogen, Carlsbad).

In certain embodiments, visualization is achieved using an E-Gel® iBase™ (Invitrogen Carlsbad), in which the electrophoresis cassette containing the electrophoresis gel is connected to, placed over a Dark Reader® (Clare Chemicals, Dolores). In certain embodiments, visualization is achieved using an E-Gel® iBase™ (Invitrogen Carlsbad), in which an E-PAGE™ or an E-Gel® cassette (Invitrogen Carlsbad) is connected to, placed over a Dark Reader® (Clare Chemicals, Dolores). In certain embodiments, visualization is achieved using an E-Gel® iBase™ (Invitrogen Carlsbad), in which the electrophoresis cassette containing the electrophoresis gel is connected to, placed over a Safe Imager™ (Invitrogen, Carlsbad). In certain embodiments, visualization is achieved using an E-Gel® iBase™ (Invitrogen Carlsbad), in which an E-PAGE™ or an E-Gel® cassette (Invitrogen Carlsbad) is connected to, placed over a Safe Imager™ (Invitrogen, Carlsbad).

In certain embodiments, visualization is achieved using an EBase® (Invitrogen Carlsbad), in which the electrophoresis cassette containing the electrophoresis gel is connected to, and epi-illumination is used to monitor the fluorescently labeled proteins. In certain embodiments, visualization is achieved using an EBase® (Invitrogen Carlsbad), in which an E-PAGE™ or an E-Gel® cassette (Invitrogen Carlsbad) is connected to, and epi-illumination is used to monitor the fluorescently labeled proteins. In such embodiments provided above the epi-illumination can be achieved using the light sources provided herein, including but not limited to white light, white light with appropriate optical filters to obtain the desired wavelength, blue light, lasers, Light-Emitting Diodes (LED's) and blue Light-Emitting Diodes (LED's).

In other embodiments, visualization is achieved using a system which combines both the power supply to drive electrophoresis and a visualization system into a single integrated unit. By way of example only, in certain embodiments visualization is achieved using an E-Gel® iBase™ which has been integrated into a visualization system disclosed herein.

Non-limiting examples of electrophoresis gel cassettes used in the methods disclosed herein, and non-limiting examples of the apparatuses in which such cassettes can be used in, have been disclosed in U.S. Pat. No. 5,582,702, U.S. Pat. No. 5,865,974, and U.S. Pat. No. 6,562,213, each of which is herein incorporated by reference in its entirety.

In certain illustrative embodiments, the electrophoresis cassettes used in the methods disclosed herein are closed electrophoresis cassettes. Closed electrophoresis gel cassette have at least four walls which are sealed to form a separation chamber surrounded by the walls, and the separation chamber contains an electrophoresis gel matrix which has at least 2 wells formed therein. In addition, at least one wall of such cassettes has an array of openings (also referred to herein as apertures) for access from outside of the cassette to the wells formed in the electrophoresis gel contained in the separation chamber, or for access from outside of the cassette to the empty separation chamber inside the cassette. Such closed cassettes also include all the chemical compounds required for driving electrophoresis separations and, in certain embodiments, for enabling visualization of the separated sample bands. In addition, such closed cassettes can be disposable. In certain embodiments the electrophoresis gel is put into the separation chamber by an outside vendor, while in other embodiment the separation chamber does not contain an electrophoresis gel until an end user puts the electrophoresis gel into the separation chamber before using the electrophoresis cassette.

Figure 14:
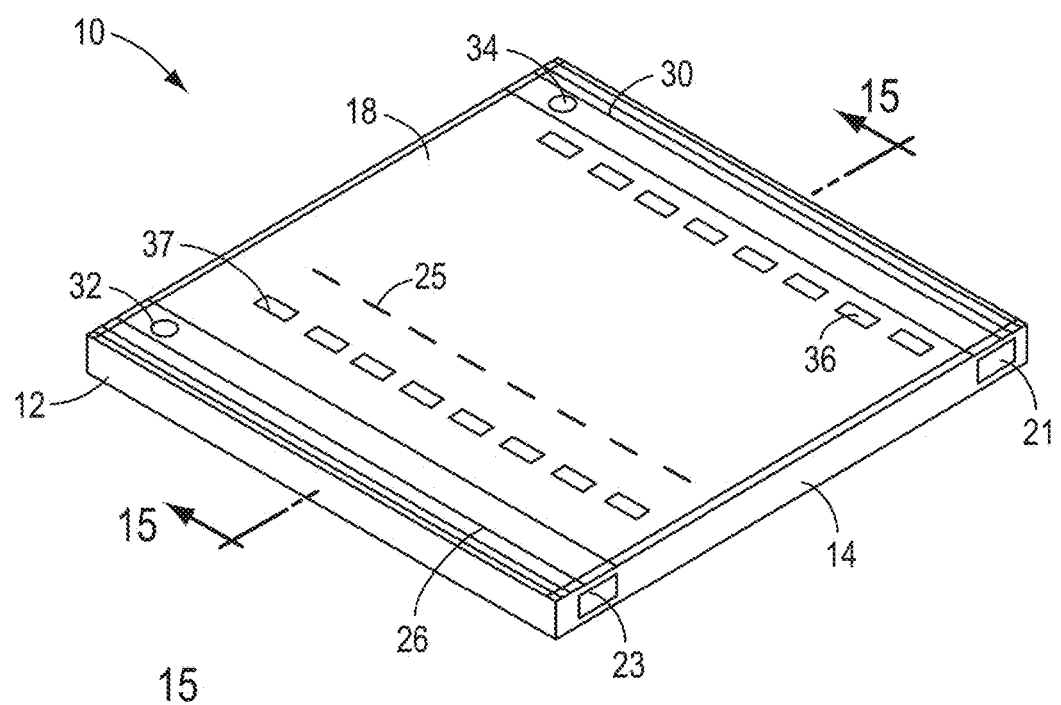
FIG. 14 is an illustration of one embodiment of the electrophoresis gel cassettes used in the methods described herein.
Figure 15A:
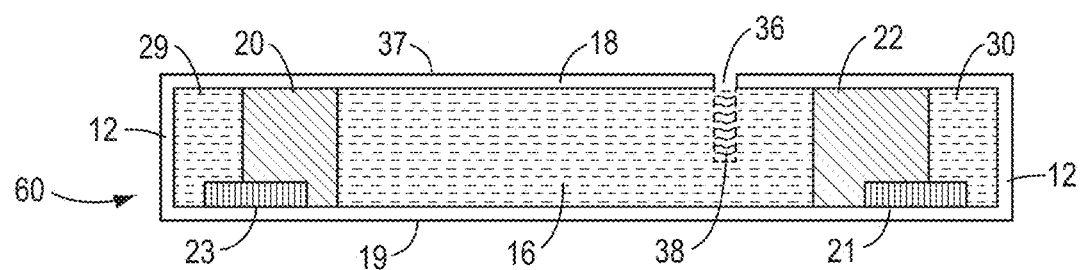
FIG. 15A and FIG. 15B are a cross-section of one embodiment of the electrophoresis gel cassettes used in the methods described herein.
Figure 15B:
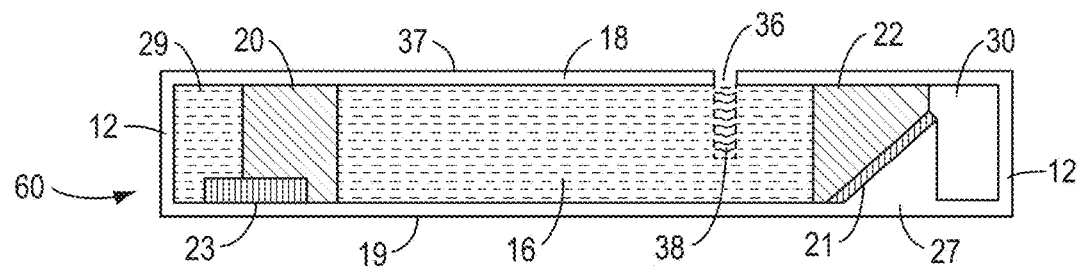

FIG. 14, FIG. 15A and FIG. 15B illustrate one embodiment of the closed cassettes used in the methods disclosed herein. FIG. 14 is an external view, wherein FIG. 15A and FIG. 15B are seen in the cross section illustration along IV-IV of FIG. 14. Cassette 10 comprises a three dimensional separation chamber having a bottom wall 19, side walls 12 and 14, and a top wall 18 each of which has a specified thickness. Cassette 10 is substantially closed in that it is enclosed by walls 12, 14, 16, and 19, but it also comprises apertures 36 as will be disclosed herein, and can also comprise optional vent holes (34 and/or 32). The thickness of the walls can range from 0.1-10 mm, and in certain embodiments the thickness is 1.5 mm. In other embodiments the thickness is 9 mm, 8 mm, 7 mm, 6 mm, 5 mm, 4 mm, 3 mm, 2 mm or 1 mm.

The length of cassette 10 can range from 50 to 200 mm, the width of cassette 10 can range from 50-150 mm and the height of cassette 10 can range from 1-10 mm. In one embodiment, the length, width and height of cassette 10 are 160 millimeters (mm), 100 mm and 6 mm, respectively. In another embodiment, the length, width and height of cassette 10 are 130 mm, 130 mm and 6 mm, respectively. In another embodiment, the length, width and height of cassette 10 are 100 mm, 80 mm and 6 mm, respectively. In another embodiment, the length, width and height of cassette 10 are 108 mm, 135 mm and 6.7 mm, respectively.

As noted above Cassette 10 may optionally include vent holes 32 and 34 to allow escape of gaseous molecules (e.g., oxygen and/or hydrogen) that might be generated during electrophoresis, due to the electrochemical reaction at electrodes 23 and 21. In certain embodiments the vent holes range in diameter from 0.5-2 mm, while in other embodiments the vent holes range in diameter from 0.5-1 mm. In other embodiments the vent holes range in diameter from 1-2 mm, and in one embodiment, the vent holes are 1 mm in diameter.

As seen in the cross section illustration of FIG. 15A and FIG. 15B, the separation chamber comprises an electrophoresis gel matrix 16, which may be any suitable electrophoresis gel matrix as described herein. The separation chamber also comprises two conductive electrodes referenced 21 and 23 which, when connected to an external direct current (DC) electrical power source, provide the electric field required to drive electrophoresis separation. In the illustrated embodiment in FIGS. 14 and 15, electrode 21 is the cathode and electrode 23 is the anode, however in other embodiments electrode 21 is the anode and electrode 23 is the cathode.

The separation chamber may optionally comprise ion exchange matrices, referenced 20 and 22. In the illustrated embodiment in FIG. 15A and FIG. 15B, electrode 21 is the cathode, electrode 23 is the anode, matrix 20 is a cation exchange, and matrix 22 is an anion exchange matrix, however in other embodiments electrode 21 is the anode, electrode 23 is the cathode, matrix 20 is an anion exchange, and matrix 22 is a cation exchange matrix.

The separation chamber may also optionally comprise internal volumes 29 and 30 which, independent of each other, may be unoccupied, occupied with electrophoresis gel matrix, or occupied with buffer. If unoccupied, the internal volume 29 or 30 is used as a volume in which gases produced during electrophoresis may accumulate. Alternatively, as noted above, cartridge 10 may optionally include at least two vent holes 32 and 34 for venting the gases accumulated in the volumes 29 and/or 30. It will be appreciated that if the cassette 10 includes vent holes 32 and 34 they are opened just before the electrophoresis begins and are closed after the test is completed to substantially reduce the possibility of contamination.

In addition, cartridge 10 may comprise a ramp 27 which can support electrode 21. The ramp facilitates continuous contact between electrode 21 and the surface of the ion exchange matrix 22 overlying electrode 21, whereby release of gas bubbles produced at the vicinity of electrode 21 are directed towards empty volume 30. In certain embodiments, the ramp 27 is formed as an integral part of cartridge 10 and is inclined to the bottom wall 19 at an angle of about 45 degrees.

Also shown in the cross section illustration of FIG. 15A and FIG. 15B, are wells 38 which are formed in electrophoresis gel matrix 16. Such wells are located underneath apertures 36. The apertures 36 shown in FIG. 14, and the corresponding wells 38, are used to introduce samples of the proteins or protein fragments which are to undergo electrophoretic separation. However, the configuration of the apertures and wells used in the methods disclosed herein are not limited to one row and can include other configurations, such as various types of arrays, as discussed herein. In one embodiment, cartridge 10 comprises a plurality of apertures and a plurality of wells, wherein the plurality of apertures and plurality of wells range from 1-200 apertures and 1-200 wells. In another embodiment, the plurality of apertures and plurality of wells range from 1-100 apertures and 1-100 wells. In another embodiment, the plurality of apertures and plurality of wells range from 1-50 apertures and 1-50 wells. In certain embodiments, cartridge 10 comprises 96 apertures and 96 wells, while in certain embodiments, cartridge 10 comprises 48 apertures and 48 wells. The dimensions of apertures 36 and 37 and wells 38 and 39 are discussed herein, however in one embodiments wells 38 and 39 have dimensions of 0.5-5 mm wide, 1-5 mm long, and 3-5 mm deep.

The wells may be formed by any suitable method, such as by introducing a "comb" into the electrophoresis gel matrix within the separation chamber during the assembly of the electrophoresis gel matrix when the electrophoresis gel matrix is still in a liquid state. The "comb" has protruding teeth positioned so that the teeth project into the electrophoresis gel matrix via the apertures in the top wall 18. The wells form in the electrophoresis gel matrix when the matrix solidifies into a gel state around the comb features. When the comb is pulled out of the electrophoresis gel matrix and the apertures the wells are available for loading with liquid, such as sample, buffer, or water. The comb may be removed just before loading, or it may be removed some time before loading, such as in the range of from 5 seconds to 1 day before loading, or 10 seconds to 12 hours before loading, or 10 seconds to 30 minutes before loading. Alternatively, the comb is pulled out of the electrophoresis gel matrix and the apertures and the top of the cassette (including the apertures and corresponding wells) is covered with tape thereby sealing the resulting wells from potential contamination. The sealing tape is then removed just before loading, or it may be removed some time before loading, such as in the range of from 5 seconds to 1 day before loading, or 10 seconds to 12 hours before loading.

In certain embodiments, the electrophoresis cassettes can have the electrodes in regions in the cassette which contain liquid buffer. In certain embodiments the regions containing liquid buffers are in the same plane as the electrophoresis gel, while in other embodiments the regions containing liquid buffers are located below or above the plane of the electrophoresis gel. In other embodiments the electrodes are in direct contact with gels, such as electrophoresis gels, which contain ions to facilitate the applied electric field but without the need for liquid buffers. In other embodiments the electrodes are embedded in gels, such as electrophoresis gels, which contain ions to facilitate the applied electric field but without the need for liquid buffers. In other embodiments the electrodes are in indirect contact with gels, such as electrophoresis gels, which contain ions to facilitate the applied electric field but without the need for liquid buffers, such indirect contact can be via another gel material or by simple electrical contact.

Alternatively the separation technique used in the methods described herein are open systems that use electrophoretic slab gels wherein the slab gel is not immersed in running buffer and is not contained within a cassette. In such a method the slab gel comprises an upper surface and a lower surface wherein the upper surface is not in contact with a liquid, or the slab gel is not immersed in a running buffer used to drive the electrophoretic separation. In such methods, by way of example only, the slab gel is placed in contact with electrodes, either directly or indirectly and an electric field is applied to drive electrophoretic migration of the sample. Indirect contact can be achieved using wicking techniques, wherein the electrodes are placed in buffer tanks which have wicking means between the slab gel and the tank, or indirect contact may be achieved using a gel matrix located between the electrodes and the slab gel. In addition, the slab gels used in such methods contains arrays of loading wells and collection wells as disclosed herein for the electrophoresis cassettes, and although no apertures are used the methods for separation are the same as those disclosed for the electrophoresis cassettes.

Alternatively the separation technique used in the methods described herein are open systems that use electrophoretic slab gels wherein the slab gel is immersed in running buffer and is not contained within a cassette.

The slab gel used and electrophoresis cassettes used in the methods disclosed herein can have a single row of wells and apertures or such gels and cassettes can have arrays of wells and apertures. Such arrays of wells and apertures can be disclosed as being "r×c" arrays, wherein r is the number of rows and c is the number of columns. The number of rows, r, and the number of columns, c, of such arrays are independent of each other and therefore the arrays of wells and apertures used in the methods disclosed herein can be symmetric arrays (where r=c) or asymmetric arrays (where r≠c). Such arrays of wells and apertures can include at least 1 row, at least 2 rows, at least 3 rows, at least 4 rows, at least 5 rows, at least 6 rows, at least 7 rows, at least 8 rows, at least 9 rows, at least 10 rows, at least 11 rows, at least 12 rows, at least 15 rows, at least 20 rows, at least 50 rows, or at least 100 rows each independently in combination with at least 1 column, at least 2 columns, at least 3 columns, at least 4 columns, at least 5 columns, at least 6 columns, at least 7 columns, at least 8 columns, at least 9 columns, at least 10 columns, at least 11 columns, at least 12 columns, at least 15 columns, at least 20 columns, at least 50 columns, or at least 100 columns.

Non-limiting examples of the arrays of wells and apertures used in the methods disclosed herein include, but are not limited to, r×1 arrays, r×2 arrays, r×3 arrays, r×4 arrays, r×5 arrays, r×6 arrays, r×7 arrays, r×8 arrays, r×9 arrays, r×10 arrays, r×11 arrays, r×12, r×13 arrays, r×14 arrays, r×15 arrays, r×16 arrays, r×17 arrays, r×18 arrays, r×19 arrays, r×20 arrays, r×21 arrays, r×22 arrays, r×23 arrays, r×24 arrays, r×25, and r×26 arrays, where r is an integer from 2 to 26.

Other non-limiting examples of the arrays of wells and apertures used in the methods disclosed herein include, but are not limited to, 1×c arrays, 2×c arrays, 3×c arrays, 4×c arrays, 5×c arrays, 6×c arrays, 7×c arrays, 8×c arrays, 9×c arrays, 10×c arrays, 11×c arrays, 12×c, 13×c arrays, 14×c arrays, 15×c arrays, 16×c arrays, 17×c arrays, 18×c arrays, 19×c arrays, 20×c arrays, 21×c arrays, 22×c arrays, 23×c arrays, 24×c arrays, 25×c, and 26×c arrays, where c is an integer from 2 to 26.

Figure 16A:
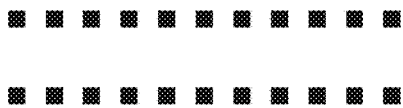
FIG. 16A, FIG. 16B, FIG. 16C, FIG. 16D, FIG. 16E and FIG. 16F illustrate embodiments of aperture and well arrangements for certain electrophoresis gel cassettes used in the methods described herein.
Figure 16B:
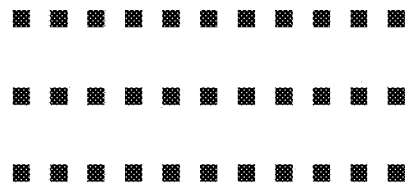
Figure 16C:
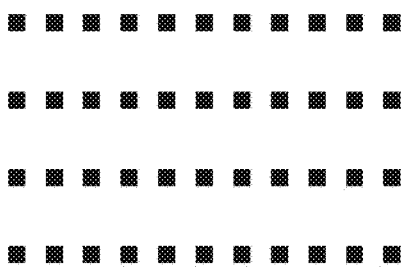
Figure 16D:
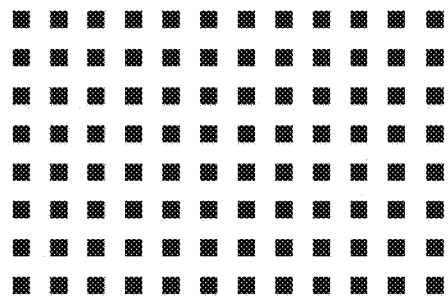
Figure 16E:
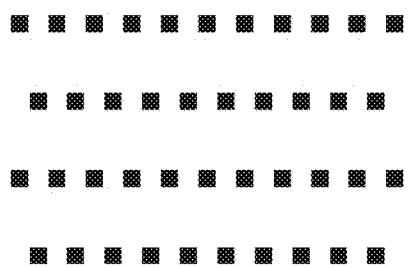
Figure 16F:
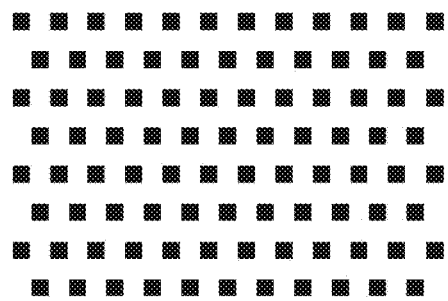

The arrangement of wells and apertures in the arrays of wells used in the methods disclosed herein can be a single row of wells and apertures. Alternatively, the arrangement of wells and apertures in the arrays of wells used in the methods disclosed herein include, but are not limited to, those illustrated in FIG. 16A, FIG. 16B, FIG. 16C, FIG. 16D, FIG. 16E and FIG. 16F. Such arrangements can be a checkerboard pattern as shown in FIGS. 16E-16F, wherein the rows are arranged in an alternating staggered format. Alternatively, the arrangement of wells and apertures can be the pattern as shown in FIGS. 16A-16D. The number of wells and apertures in such array patterns can be from 2 to 200, from 2 to 150, from 2 to 96, from 2 to 48, from 2 to 24, or from 2 to 12.

In certain embodiments the spacing between the wells, and the spacing between the apertures, in the rows of the arrays of wells and apertures is equidistant and can range between 5 mm to 10 cm measured from the center of one well to the next well. In certain embodiments the spacing between the wells, and the spacing between the apertures, in the columns of the arrays of wells and apertures is equidistant and can range between 5 mm to 10 cm measured from the center of one well to the next well.

In certain embodiments the spacing between the wells, and the spacing between the apertures, in the rows of the arrays of wells and apertures can increase from left to right in linear increments, with the first spacing in the range between 5 mm to 10 cm measured from the center of the first well to the next well and the increment step in the range between 5 mm to 10 cm. Alternatively, in certain embodiments the spacing between the wells, and the spacing between the apertures, in the rows of the arrays of wells and apertures can decrease from left to right in linear increments, with the first spacing in the range between 5 mm to 10 cm measured from the center of the first well to the next well and the increment in the range between 5 mm to 10 cm.

In certain embodiments the spacing between the wells, and the spacing between the apertures, in the rows of the arrays of wells and apertures can increase from left to right in non-linear increments, with the first spacing in the range between 5 mm to 10 cm measured from the center of the first well to the next well and the increment step in the range between 5 mm to 10 cm. Alternatively, in certain embodiments the spacing between the wells, and the spacing between the apertures, in the rows of the arrays of wells and apertures can decrease from left to right in non-linear increments, with the first spacing in the range between 5 mm to 10 cm measured from the center of the first well to the next well and the increment step in the range between 5 mm to 10 cm.

In certain embodiments the spacing between the wells, and the spacing between the apertures, in the columns of the arrays of wells and apertures can increase from top to bottom in linear increments, with the first spacing in the range between 5 mm to 10 cm measured from the center of the first well to the next well and the increment step in the range between 5 mm to 10 cm. Alternatively, in certain embodiments the spacing between the wells, and the spacing between the apertures, in the columns of the arrays of wells and apertures can decrease from top to bottom in linear increments, with the first spacing in the range between 5 mm to 10 cm measured from the center of the first well to the next well and the increment step in the range between 5 mm to 10 cm.

In certain embodiments the spacing between the wells, and the spacing between the apertures, in the columns of the arrays of wells and apertures can increase from top to bottom in non-linear increments, with the first spacing in the range between 5 mm to 10 cm measured from the center of the first well to the next well and the increment step in the range between 5 mm to 10 cm. Alternatively, in certain embodiments the spacing between the wells and the spacing between the apertures, in the columns of the arrays of wells can decrease from top to bottom in non-linear increments, with the first spacing in the range between 5 mm to 10 cm measured from the center of the first well to the next well and the increment step in the range between 5 mm to 10 cm.

Each well and apertures in an array of wells and apertures can be, independent of the other, circular, semi-circular, square, rectangular, triangular, or oval in shape. The dimensions of different shaped wells can be as follows:

circular wells: diameter between 2 mm to 15 mm; and depth between 1 mm and 6 mm,
semi-circular wells: radius between 1 mm to 7.5 mm; and depth between 1 mm and 6 mm,
square wells: length and width between 2 mm to 15 mm; and depth between 1 mm and 6 mm,
rectangular wells: length between 2 mm to 15 mm; width between 2 mm to 15 mm; and depth between 1 mm and 6 mm,
triangular wells: length between 2 mm to 15 mm; height between 2 mm to 15 mm; and depth between 1 mm and 6 mm,
oval wells: length between 2 mm to 15 mm; height between 2 mm to 15 mm; and depth between 1 mm and 6 mm.

Although the wells can be circular or oval in shape it is preferred that the wells of the invention be square, rectangular, semi-circular or triangular with a substantially flat wall in the direction of electrophoresis, because non-flat walls in the direction of electrophoresis can adversely affect the shape of a sample band during electrophoresis and thereby affect the resolution of separating sample components. In addition, the depth of the wells should be less than the thickness of the electrophoresis gel, wherein the bottom of the wells are formed by the electrophoresis gel and not by the wall of the electrophoresis cassette.

Each well in an array of wells can have, independent of the other wells, a volume ranging from 150 nL to 14 mL. In certain embodiments the volume of each well, independent of other wells can range from 5 µL to 10 mL. In certain embodiments the volume of each well, independent of other wells can range from 5 µL to 1 mL. In certain embodiments the volume of each well, independent of other wells can range from 5 µL to 500 µL. In certain embodiments the volume of each well, independent of other wells can range from 5 µL to 200 µl. In certain embodiments the volume of each well, independent of other wells can range from 5 µL to 100 µL. The larger volume wells, including but not limited to wells having volumes ranging from 500 µL to 14 mL, can be used for the separation, isolation and collection of a component of interest from large sample volumes.

The polymeric components of the gel cassettes used in the methods described herein can be made of a polymer which is transparent to visible light, transparent to ultraviolet light, transparent to infra-red light, or transparent to both visible and ultraviolet light. Non-limiting examples of polymers used to make the gel cassettes disclosed herein are styrene acrylonitrile, polycarbonate, polystyrene, acrylic based polymers, polymethyl methacrylate, polyethylene terephthalate, glycol-modified polyethylene terephthalate, polypropylene, Acetel and copolymers thereof. The polymeric components of the gel cassettes may be fabricated using molding techniques, hot embossing methods, casting processes, thermoforming methods, stereolithography processes, machining methods and milling processes. In further or alternative embodiments, such molding techniques include injection molded and compression molding.

As disclosed herein the gel cassettes also includes two electrodes, an anode and a cathode, wherein the array of wells and apertures are located between the electrodes. Such electrodes are used to create an electric field used to drive electrophoretic migration and separation of the components of a sample. The electrodes of the electrophoresis cassette can be electrically conductive metallic material or electrically conductive non-metallic including, but not limited to, platinum, gold, copper, lead, aluminum, silver, nickel, iron, stainless steel, graphite, or carbon. Alternatively, the electrodes of the electrophoresis cassette can comprise a non-conducting material which is coated with an electrically conductive metal or non-metal including, but not limited to, platinum, palladium, gold, copper, lead, aluminum, silver, nickel, iron, stainless steel, graphite, carbon or combinations thereof.

The array of apertures in the electrophoresis gel cassette has at least one row or column of loading apertures in which a sample can be loaded through an aperture into a corresponding loading well located underneath the loading aperture.

The electrophoresis gel cassettes used in the methods disclosed herein can optionally have a cation ion exchange matrices located between the anode and the electrophoresis gel, and can have an anion ion exchange matrices located between the cathode and the electrophoresis gel. A non-limiting example of a cation exchange material incorporated into the gel cassette is CM-25-120 Sephadex and a non-limiting example an anion exchange material incorporated into the gel cassette is WA-30, both of which are commercially available from Sigma Inc. of St. Louis, U.S.A.

The electrophoresis gel cassettes used in the methods disclosed herein can have the electrophoresis gel already cast in the separation chamber with the wells being optionally occupied by at least one gel comb. The comb or combs are removed to give wells available for use as loading wells and collection wells. Alternatively, the electrophoresis gel cassettes used in the methods disclosed herein can be empty and the electrophoresis gel is cast, using appropriate combs, by the user to create an array of wells available for use as loading wells and collection wells.

Compositions

In another aspect, provided herein are compositions useful in the practice of the methods described herein. One embodiment is a composition comprising a biarsenical fluorophore, an amine reactive fluorescent dye and a reducing agent. Another embodiment is a composition at a pH from pH 6 to pH 9 comprising an amine reactive fluorogenic reagent, an alkali cyanide (or alternatively acetone cyanohydrin or a nitrile such as mandelonitrile) and a reducing agent. Another embodiment is a composition at a pH from pH 6 to pH 9 comprising an amine reactive fluorogenic reagent, an alkali cyanide (or alternatively acetone cyanohydrin or mandelonitrile), a biarsenical fluorophore and a reducing agent.

In another aspect are compositions that include a buffer having a pH in the range from pH 8 to pH 10, a tag binding fluorogenic dye, an anionic surfactant, a sugar or a sugar alcohol, a tracking dye, one or more reducing agents and a bicarbonate salt.

In certain embodiments, the reducing agent or agents of such composition is selected from a trialkylphosphine compound, dithiothreitol (DTT), 2-mercaptoethanol, sodium bisulfite, thioglycolic acid, mercaptoethanesulfonic acid or glutathione, wherein the trialkylphosphine compound is tri-N-butylphosphine (TBP) or tris[2-carboxyethyl] phosphine (TCEP).

In certain embodiments, the tag binding fluorogenic dye of such composition is a biarsenical fluorophore. In certain embodiments, the tag binding fluorogenic dye of such composition is a biarsenical derivative of fluorescein. In certain embodiments, the tag binding fluorogenic dye of such composition is 4'-6-bis(1,3,2-dithioarsolan-2-yl)fluorescein-(2,2-ethanedithiol)$_2$. In certain embodiments, the tag binding fluorogenic dye of such composition is a biarsenical derivative of resorufin. In certain embodiments, the tag binding fluorogenic dye of such composition is 4'-6-bis(1,3,2-dithioarsolan-2-yl)resorufin-(2,2-ethanedithiol)$_2$.

In certain embodiments, the anionic surfactant of such compositions is an alkyl benzenesulfonate, an alkyl sulfonate, an alkyl sulfosuccinate, an alkyl phosphate, an alkyl sulfate, an alkyl carboxylate, an alkyl ether benzenesulfonate, an alkyl ether sulfonate, a alkyl ether sulfosuccinate, an alkyl ether phosphate, an alkyl ether sulfate or an alkyl ether carboxylate. In certain embodiments, the anionic surfactant of such compositions is sodium dodecyl sulfate, lithium dodecyl sulfate, sodium lauryl ether sulfate, sodium oleate, sodium palmitate, sodium myristate or sodium stearate. In certain embodiments, the anionic surfactant of such compositions is sodium dodecyl sulfate or lithium dodecyl sulfate.

In certain embodiments, the anionic surfactant of such compositions is sucrose, and in other embodiments, the sugar alcohol is glycerol. In certain embodiments, the tracking dye is bromophenol blue. In certain embodiments, the buffer of such compositions is selected from the group consisting of carbonate, bicarbonate, phosphate, borate, Bis-Tris propane, and bicine. In certain embodiments, such compositions further comprise a tagged protein. In certain embodiments, the tagged protein is tagged with a tetracysteine containing peptide.

In certain embodiments, such compositions further include an amine reactive fluorescent dye. In certain embodiments, the amine reactive fluorescent dye of such compositions has a fluorescent moiety selected from the group consisting of a fluorescein moiety, a rhodamine moiety, an acridine moiety, a coumarin moiety, an indole moiety, an isoindole moiety, an indolizine moiety, a quinoline moiety, an isoquinoline moiety, a chromene moiety, a xanthene moiety, a naphthalene moiety, a pyrene moiety, a bimane moiety and a BODIPY moiety. In certain embodiments, the amine reactive fluorescent dye of such compositions further comprises a reactive moiety selected from the group consisting of an acyl azide, a carbonyl azide, an isothiocyanate, an isocyanate, a succinimidyl ester, a carboxylic ester, a carboxylic acid, a succinimidyl ester, a sulfosuccinimidyl ester, an STP ester, a tetrafluorophenyl ester, a sulfonyl chloride, an acid halide, an aldehyde, a carboxyaldehyde a dichlorotriazine, an NBD chloride, or an NBD fluoride.

In one embodiment the composition includes a phosphate buffer having a pH in the range from pH 8 to pH 10, 4'-5'-bis(1,3,2-dithioarsolan-2-yl)fluorescein-(2,2-ethanedithiol)$_2$, sodium dodecyl sulfate, glycerol, bromophenol blue, tris[2-carboxyethyl] phosphine (TCEP), mercaptoethanesulfonic acid and a bicarbonate salt.

Kits

In another aspect disclosed herein are kits used for protein labeling and analysis. In certain embodiments the kit includes an amine reactive fluorogenic reagent as described herein, an alkali cyanide (or alternatively acetone cyanohydrin or a nitrile such as mandelonitrile) as described herein, a first buffer as described herein and a second buffer as described herein. The kits can optionally include a reducing agent as described herein, a gel cassette as described herein, an anionic surfactant as described herein, an alkylating agent such as dimethyl acrylamide (DMA) and other alkylating agents as known in the art, or combinations thereof. Furthermore, the kits can optionally include an alternative, non-fluorescent gel loading buffer which may containing one or more tracking dyes such as bromophenol blue, bromocresol green, Serva blue G250, or Ponceau S but not phenol red.

In other embodiments disclosed herein are kits that include a biarsenical fluorophore as described herein, an amine reactive fluorescent dye as described herein, a first buffer as described herein and a second buffer as described herein. The kits can optionally include a reducing agent as described herein, a gel cassette as described herein, an anionic surfactant as described herein, an alkylating agent such as (DMA) and other alkylating agents as known in the art, or combinations thereof.

In certain embodiments are kits that include:
a) a first composition comprising a buffer having a pH in the range from pH 8 to pH 10, a fluorogenic dye that binds to at least four cyteine moieties, at least one reducing agent, an anionic surfactant, a sugar or a sugar alcohol, a tracking dye, one or more reducing agents and a bicarbonate salt; and
b) a second composition comprising an amine reactive fluorescent dye.

In certain embodiments of such kits the amine reactive fluorescent dye comprises a fluorescent moiety selected from the group consisting of a fluorescein moiety, a rhodamine moiety, an acridine moiety, a coumarin moiety, an indole moiety, an isoindole moiety, an indolizine moiety, a quinoline moiety, an isoquinoline moiety, a chromene moiety, a xanthene moiety, a naphthalene moiety, a pyrene moiety, a bimane moiety and a BODIPY moiety. In other embodiments of such kits, the amine reactive fluorescent dye further comprises a reactive moiety selected from the group consisting of an acyl azide, a carbonyl azide, an isothiocyanate, an isocyanate, a succinimidyl ester, a carboxylic ester, a carboxylic acid, a succinimidyl ester, a sulfosuccinimidyl ester, an STP ester, a tetrafluorophenyl ester, a sulfonyl chloride, an acid halide, an aldehyde, a carboxyaldehyde a dichlorotriazine, an NBD chloride, or an NBD fluoride. In other embodiments of such kits, anionic surfactant is sodium dodecyl sulfate, lithium dodecyl sulfate, sodium lauryl ether sulfate, sodium oleate, sodium palmitate, sodium myristate or sodium stearate. In other embodiments of such kits, the anionic surfactant is sodium dodecyl sulfate or lithium dodecyl sulfate. In other embodiments of such kits, the reducing agent is selected from a trialkylphosphine compound, dithiothreitol (DTT), 2-mercaptoethanol, sodium bisulfite, thioglycolic acid, mercaptoethanesulfonic acid, glutathione or combinations thereof. In other embodiments of such kits, the trialkylphosphine compound is tri-N-butylphosphine (TBP) or tris[2-carboxyethyl] phosphine (TCEP). In other embodiments of such kits, the fluorogenic dye that binds to at least four cysteine moieties is a biarsenical fluorophore. In other embodiments of such kits, the biarsenical fluorophore is a biarsenical derivative of fluorescein. In other embodiments of such kits, the biarsenical fluorophore is 4'-5'-bis(1,3,2-dithioarsolan-2-yl)fluorescein-(2,2-ethanedithiol)$_2$. In other embodiments of such kits, the biarsenical fluorophore is a biarsenical derivative of resorufin. In other embodiments of such kits, the biarsenical fluorophore is 4'-5'-bis(1,3,2-dithioarsolan-2-yl)resorufin-(2,2-ethanedithiol)$_2$. In other embodiments of such kits, the sugar is sucrose. In other embodiments of such kits, sugar alcohol is glycerol. In other embodiments of such kits, the tracking dye is bromophenol blue. In other embodiments of such kits, the buffer is selected from the group consisting of carbonate, bicarbonate, phosphate, borate, Bis-Tris propane, and bicine.

In one embodiment, the kit comprises a first composition comprising 6% w/v LDS, 30% w/v sucrose, 1 M carbonate buffer (approximately pH of 9.2), 5× mandelonitrile, and ATTO-TAG FQ in DMSO; and a second composition comprising a fluorescence-free buffer (4×).

It will be appreciated by persons skilled in the art that the present invention is not limited to what has been particularly shown and disclosed hereinabove. The invention will be further clarified by a consideration of the following examples, which are intended to be purely exemplary of the invention and not to in any way limit its scope. The following examples are intended to illustrate but not limit the invention disclosed herein.

EXAMPLES

Unless otherwise noted, the following materials and stock reagents were used in Examples 1-9.
1 M carbonate/bicarbonate buffer, pH=9.2:
  2.3 mL of 1M sodium bicarbonate (J.T. Baker) in water
  0.2 mL of 1M sodium carbonate (Fisher) in water
5×LDS/sucrose:
  10% w/v LDS (Sigma) and 50% w/v sucrose (Research Organics) in water
3× bis-Tris:
  0.90 bis-Tris (Research Organics) in water, adjusted to pH to 6.5 using 6N HCl (VWR)
1× bis-Tris/LDS/sucrose (300 mM bis-Tris, 2% LDS, and 10% sucrose):
  prepared by diluting 3× bis-Tris and 5×LDS/sucrose with an appropriate volume of ultra-pure water
1× NuPAGE® Sample Buffer:
  prepared by using ultra-pure water to dilute NuPAGE® LDS Sample Buffer (4×) (Invitrogen)
20 mM ATTO-TAG™ FQ (Molecular Probes, Eugene, Oreg.):
  995 µL methanol (J.T. Baker) to a vial containing 5 mg solid material 100 mM sodium cyanide (Fluka), acetone cyanohydrin or mandelonitrile in water The "10×" labeling solution used in Examples 1-9 was prepared according Table 1 below.

TABLE 1

| Stock Solution | Component Volume (µl) |
| --- | --- |
| 5X LDS/sucrose* | 120* |
| 1M carbonate/bicarbonate, pH = 9.2 | 30 |
| 100 mM NaCN or mandelonitrile | 30 |
| 20 mM ATTO-TAG-FQ | 60 |
| ultra pure water | 60 |
| Total Volume | 300 µl |

*For ready-to-use standards, 5X LDS/sucrose was not added into the pre-mix: ultra-pure water at the same volume was added instead.

The concentrations of the components of the "10×" labeling solution are listed in table 2 below.

TABLE 2

| Reaction Mixture Component | Concentration during Labeling |
| --- | --- |
| LDS & sucrose* | 1X* |
| carbonate/bicarbonate buffer | 50 mM |
| purified protein | 0.5 or 5 mg/ml |
| NaCN or mandelonitrile | 5 mM |
| ATTO-TAG-FQ | 2 mM |
| Methanol (from FQ stock) (optionally, DMSO can be used in place of methanol) | 10% |

*For ready-to-use standards, 5X LDS/sucrose was not added into the pre-mix: ultra-pure water at the same volume was added instead.

The "1×" labeling solution used in Examples 1-9 was prepared by a 1 to 10 dilution of the 10× solution and the concentrations of the components of the "1×" labeling solution are listed in table 3 below.

TABLE 3

| Reaction Mixture Component | Concentration during Labeling |
| --- | --- |
| LDS & sucrose* | 0.1X* |
| carbonate/bicarbonate buffer | 5 mM |
| purified protein | 0.5 or 5 mg/ml |
| NaCN | 0.5 mM |
| ATTO-TAG-FQ | 0.2 mM |
| Methanol (from FQ stock) | 1% |

*For ready-to-use standards, 5X LDS/sucrose was not added into the pre-mix: ultra-pure water at the same volume was added instead.

The protein stocks used in Example 1-9, either 1 mg/mL or 10 mg/mL, were prepared by weighing solid material (lyophilized), except in the case of h-IgG which was supplied as an 11 mg/ml stock solution) and then dissolving with an appropriate volume of ultra-pure water. The proteins used in Examples 1-9 were Bovine serum Albumin (BSA), Fraction V (Sigma); Human IgG (h-IgG) (Pierce); lysozyme from chicken egg white (Sigma) and myoglobin from horse heart (Sigma).

Example 1: Labeling of Protein Standards and Purified Proteins

One embodiment of labeling of protein standards and other proteins, such as bovine serum albumin (BSA) and lysozyme, with amine reactive fluorogenic reagents is shown in FIG. 5. BSA and lysozyme were labeled in micro-centrifuge tubes by initially adding 5 µl of the 10× labeling solution to 5 µl of either a 1 mg/mL protein stock solution or a 10 mg/ml protein stock and incubate at room temperature for 10 minutes. Then 2 µl of 5×LDS/sucrose, 6 µl of 0.91 M bis-Tris (pH 6.5) and 2 µl of NuPAGE® Sample Reducing Agent (10×) (or ultra-pure water for non-reduced samples), were added, resulting in 0.125 mg/ml or 1.25 mg/ml concentrations of each protein, and this mixture was then incubated at 70° C. for 10 minutes. After incubation the mixtures were further diluted using either 1× NuPAGE® Sample Buffer or 1× bis-Tris/LDS/sucrose to achieve 0.1 mg/ml or 1 mg/ml protein concentrations. For electrophoretic separation using gel electrophoresis the protein concentration used was 0.1 mg/ml, therefore, prior to loading the labeled samples, the 1 mg/ml samples were diluted ten-fold with 1× NuPAGE® Sample Buffer.

The labeling of the BenchMark™ Protein Ladder (Invitrogen, Carlsbad) and the Mark12™ Unstained Standard (Invitrogen, Carlsbad) was achieved by adding 5 µl of the 10× labeling solution (with the 5×LDS/sucrose replaced with the same volume of ultra-pure water) to 5 µl of the BenchMark™ Protein Ladder (Invitrogen, Carlsbad) and the Mark12™ Unstained Standard (Invitrogen, Carlsbad) and incubate at room temperature for 10 minutes.

The electrophoretic separation was achieved by loading the final samples (2 µl of 0.1 mg/ml preparation for 200 ng protein in gel) into NuPAGE® 4-12% Bis-Tris gels (Invitrogen), electrophoresing at 200 volts in either an XCell SureLock™ Mini-Cell (Invitrogen) or XCell4 SureLock™ Midi-Cell (Invitrogen) using 1× NuPAGE® 2-(N-morpholino)-ethanesulfonic acid (MES)/SDS running buffer (Invitrogen), and stained using SimplyBlue™ SafeStain (Invitrogen) according to supplied instruction manuals. The labeled BenchMark™ Protein Ladder (Invitrogen, Carlsbad)

and the Mark12™ Unstained Standard (Invitrogen, Carlsbad) were loaded directly without further dilution or addition of reducing agent.

Figure 5A:
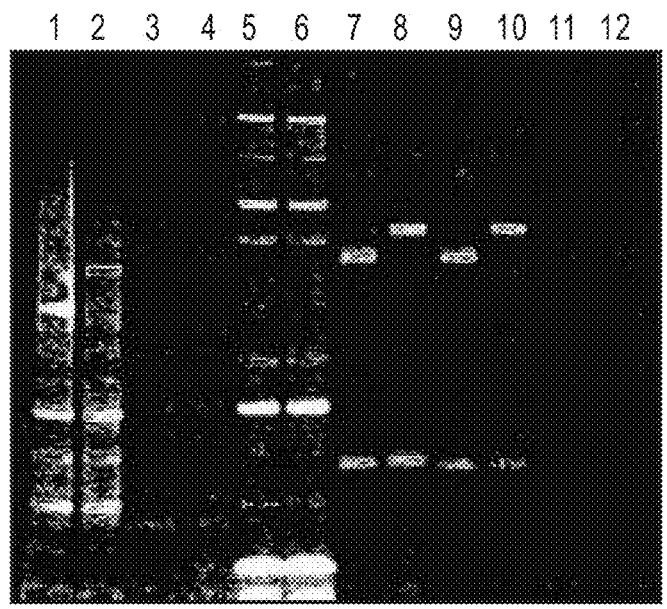
FIG. 5A and FIG. 5B are gel images where
Figure 5B:
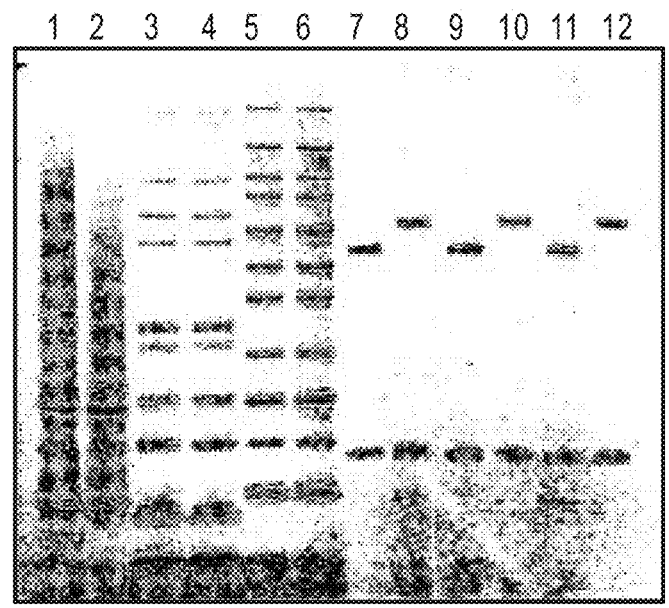

The electrophoretic separation of the fluorescently labeled protein standards, labeled BSA and labeled lysozyme is shown in the gel images given in FIG. 5A. FIG. 5B is a post stain with SimplyBlue™ SafeStain to demonstrate the effectiveness of the labeling method using amine reactive fluorogenic dyes as described herein. The labeled samples correspond to the following gel lanes given in the gel images of FIG. 5A and FIG. 5B:

| Gel Lane | Sample |
|---|---|
| 1. | 5 µl labeled BenchMark™ Protein Ladder (Invitrogen, Carlsbad) |
| 2. | 5 µl labeled and re-reduced BenchMark™ Protein Ladder (Invitrogen, Carlsbad) |
| 3. | 5 µl labeled Mark12™ Unstained Standard (Invitrogen, Carlsbad) |
| 4. | 5 µl labeled and re-reduced Mark12™ Unstained Standard (Invitrogen, Carlsbad) |
| 5. | 5 µl labeled Novex® Sharp Pre-stained Protein Standards (Invitrogen, Carlsbad) |
| 6. | 5 µl labeled and re-reduced Novex® Sharp Pre-stained Protein Standards (Invitrogen, Carlsbad) |
| 7. | 200 ng BSA, 200 ng lysozyme labeled at 0.5 mg/ml, non-reduced |
| 8. | 200 ng BSA, 200 ng lysozyme labeled at 0.5 mg/ml, reduced |
| 9. | 200 ng BSA, 200 ng lysozyme labeled at 5 mg/ml, non-reduced |
| 10. | 200 ng BSA, 200 ng lysozyme labeled at 5 mg/ml, reduced |
| 11. | 200 ng BSA, 200 ng lysozyme, unlabeled control, non-reduced |
| 12. | 200 ng BSA, 200 ng lysozyme, unlabeled control, reduced |

Example 2: Sensitivity of Detection

The sensitivity of detection obtained using the protein labeling with amine reactive fluorogenic reagents as described herein was evaluated by detecting various concentrations of labeled bovine serum albumin (BSA) and lysozyme.

The BSA and lysozyme were labeled in micro-centrifuge tubes by initially adding 5 µl of the 10× labeling solution to 5 µl of a 1 mg/mL protein stock solution and incubate at room temperature for 10 minutes. Then 2 µl of 5×LDS/sucrose, 6 µl of 0.91 M bis-Tris (pH 6.5) and 2 µl of NuPAGE® Sample Reducing Agent (10×) (or ultra-pure water for non-reduced samples), were added, resulting in 0.125 mg/ml concentrations of each protein, and this mixture was then incubated at 70° C. for 10 minutes. After incubation the mixtures were further diluted using either 1× NuPAGE® Sample Buffer or 1× bis-Tris/LDS/sucrose to achieve 0.1 mg/ml (200 ng protein in gel). This solution was then further diluted with 1× bis-Tris/LDS/sucrose to obtain solutions of 20 ng protein, 5 ng protein, 2 ng protein, 0.5 ng protein and 0.2 ng protein.

The electrophoretic separation was achieved by loading 2 µl of the dilution series into NuPAGE® 4-12% Bis-Tris gels (Invitrogen), electrophoresing at 200 volts in either an XCell SureLock™ Mini-Cell (Invitrogen) or XCell4 SureLock™ Midi-Cell (Invitrogen) using 1× NuPAGE® 2-(N-morpholino)-ethanesulfonic acid (MES)/SDS running buffer (Invitrogen), and stained using SimplyBlue™ SafeStain (Invitrogen) according to supplied instruction manuals.

Figure 6A:
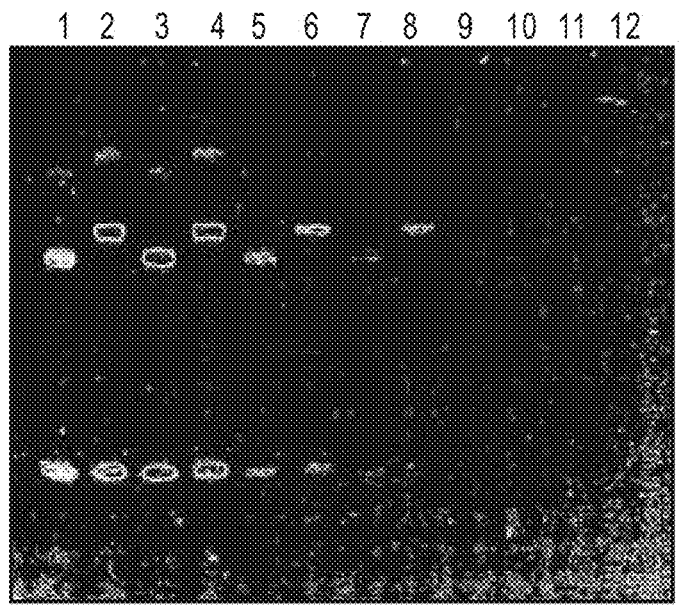
FIG. 6A and FIG. 6B illustrate the detection sensitivity obtained using the protein labeling methods described herein.
Figure 6B:
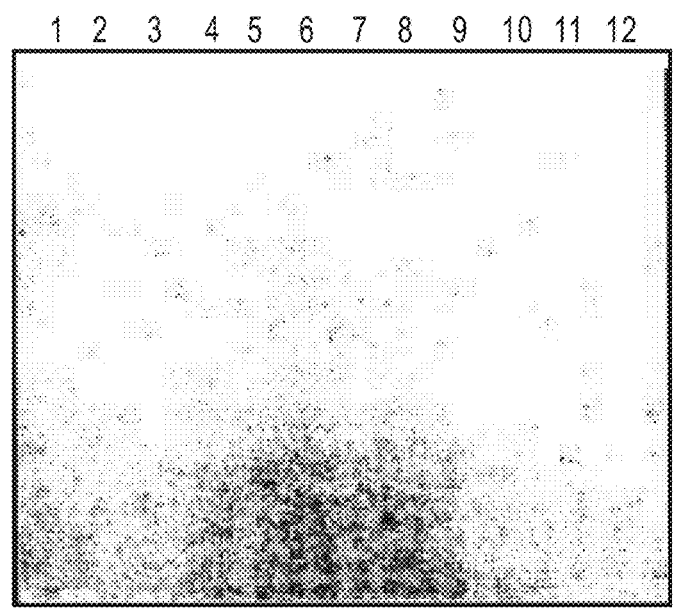

The electrophoretic separation of the fluorescently labeled protein standards, labeled BSA and labeled lysozyme is shown in the gel images given in FIG. 6A. FIG. 6B is a post stain with SimplyBlue™ SafeStain to demonstrate the effectiveness of the labeling method using amine reactive fluorogenic dyes as described herein. SimplyBlue™ SafeStain has detection sensitivity for BSA of approximately 20 ng, meaning that there would be little or no image produced at this amount or lesser protein amounts (as shown in FIG. 6B). In contrast, the labeling methods of the present invention are able to provide significant images for these protein levels (FIG. 6A). The labeled samples correspond to the following gel lanes given in the gel images of FIG. 6A and FIG. 6B:

| Gel Lane | Sample |
|---|---|
| 1 and 3 | 20 ng BSA, 20 ng lysozyme, labeled, non-reduced |
| 2 and 4 | 20 ng BSA, 20 ng lysozyme, labeled, reduced |
| 5. | 5 ng BSA, 5 ng lysozyme, labeled, non-reduced |
| 6. | 5 ng BSA, 5 ng lysozyme, labeled, reduced |
| 7. | 2 ng BSA, 2 ng lysozyme, labeled, non-reduced |
| 8. | 2 ng BSA, 2 ng lysozyme, labeled, reduced |
| 9. | 0.5 ng BSA, 0.5 ng lysozyme, labeled, non-reduced |
| 10. | 0.5 ng BSA, 0.5 ng lysozyme, labeled, reduced |
| 11. | 0.2 ng BSA, 0.2 ng lysozyme, labeled, non-reduced |
| 12. | 0.2 ng BSA, 0.2 ng lysozyme, labeled, reduced |

Example 3: Sensitivity of Detection

The sensitivity of detection obtained using different imaging instrumentation to measure proteins labeled with amine reactive fluorogenic reagents according to the methods described herein was evaluated with various concentrations of labeled bovine serum albumin (BSA).

The BSA was labeled in micro-centrifuge tubes by initially adding 5 µl of the 10× labeling solution to 5 µl of a 10 mg/mL BSA stock solution and incubate at room temperature for 10 minutes. Then 2 µl of 5×LDS/sucrose, 6 µl of 0.91 M bis-Tris (pH 6.5) and 2 µl of NuPAGE® Sample Reducing Agent (10×), were added, resulting in 1.25 mg/ml concentrations of BSA. This mixture was then incubated at 70° C. for 10 minutes. After incubation the mixtures were further diluted using either 1× NuPAGE® Sample Buffer or 1× bis-Tris/LDS/sucrose to achieve 1 mg/ml (2000 ng protein in gel). This solution was then further diluted with 1× bis-Tris/LDS/sucrose to obtain solutions of 500 ng BSA, 200 ng BSA, 50 ng BSA, 20 ng BSA, 5 ng BSA, 2 ng BSA, 0.5 ng BSA, 0.2 ng BSA and 0.05 ng BSA.

The electrophoretic separation was achieved by loading 2 µl of the dilution series into NuPAGE® 4-12% Bis-Tris gels (Invitrogen), electrophoresing at 200 volts in either an XCell SureLock™ Mini-Cell (Invitrogen) or XCell4 SureLock™ Midi-Cell (Invitrogen) using 1× NuPAGE® 2-(N-morpholino)-ethanesulfonic acid (MES)/SDS running buffer (Invitrogen), and stained using SimplyBlue™ SafeStain (Invitrogen) according to supplied instruction manuals.

Figure 7A:
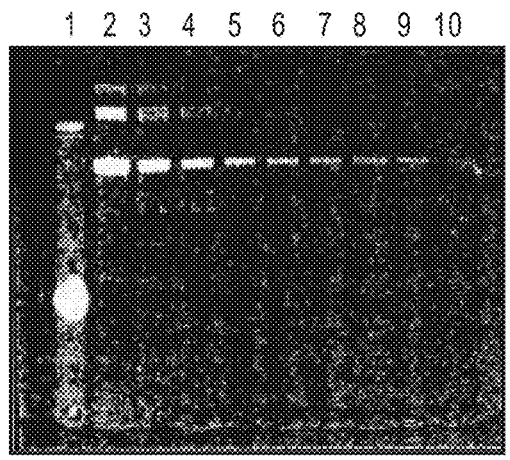
FIG. 7A, FIG. 7B and FIG. 7C compare the detection sensitivity obtained using the protein labeling methods described herein with two different detection instruments.
Figure 7B:
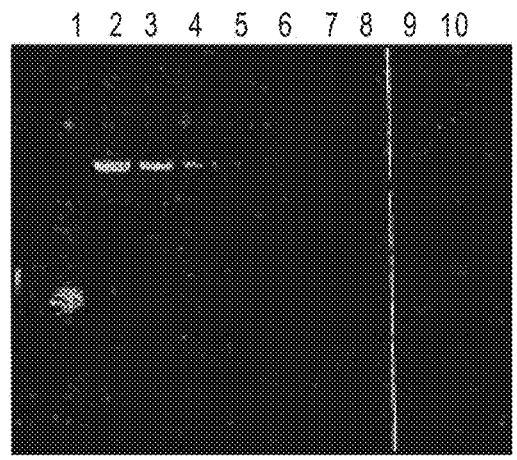
Figure 7C:
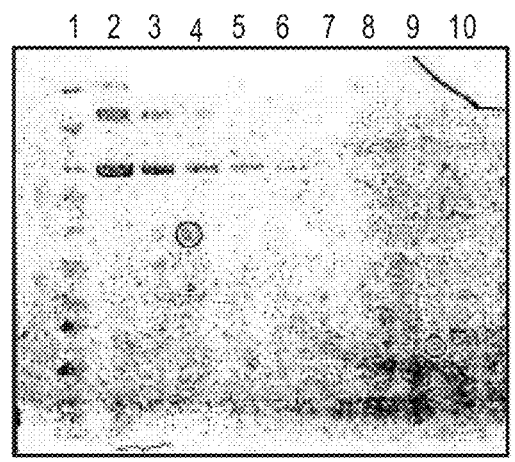

The electrophoretic separation of the fluorescently labeled BSA and a pre-labeled standard (SeeBlue® Plus2 Protein Standard (Invitrogen, Carlsbad)) is shown in the gel images given in FIGS. 7A and 7B. FIG. 7A is a gel image of labeled BSA (reduced) obtained using Fujifilm LAS-1000 with a 477 nm EPI light source, 520-640 nm band pass filter and exposure time of 60 seconds. FIG. 7B is an image obtained using a Safe Imager (~470 nm light source) image obtained with Kodak DC290 digital camera (2.1 MP) and exposure time of 8 seconds. FIG. 7C is a post stain with SimplyBlue™ SafeStain to demonstrate the effectiveness of the labeling method using amine reactive fluorogenic dyes as described herein. The labeled samples correspond to the following gel lanes given in the gel images of FIG. 7A, FIG. 7B and FIG. 7C:

| Gel Lane | Sample |
|---|---|
| 1. | 3 µl SeeBlue ® Plus2 Protein Standard (Invitrogen, Carlsbad) |
| 2. | 500 ng BSA |
| 3. | 200 ng BSA |
| 4. | 50 ng BSA |
| 5. | 20 ng BSA |
| 6. | 5 ng BSA |
| 7. | 2 ng BSA |
| 8. | 0.5 ng BSA |
| 9. | 0.2 ng BSA |
| 10. | 0.05 ng BSA |

Example 4: Labeling of Cell Lysate

The labeling of cell lysate at various times with amine fluorogenic reagents using the methods described herein was demonstrated by labeling E. coli lysate.

The E. coli lysate was labeled in micro-centrifuge tubes by initially adding 5 µl of the 10× labeling solution to 5 µl of an E. coli lysate and incubate at room temperature for 10 minutes, 30 minutes and 1 hour. Then for each sample 2 µl of 5×LDS/sucrose, 6 µl of 0.91 M bis-Tris (pH 6.5) and 2 µl of NuPAGE® Sample Reducing Agent (10×), were added, and the mixtures were incubated at 70° C. for 10 minutes. After incubation the mixtures were diluted using either 1× NuPAGE® Sample Buffer or 1× bis-Tris/LDS/sucrose to achieve.

The electrophoretic separation was achieved by loading 2 µl of the labeled E. coli lysate (10 µg per lane) into NuPAGE® 4-12% Bis-Tris gels (Invitrogen), electrophoresing at 200 volts in either an XCell SureLock™ Mini-Cell (Invitrogen) or XCell4 SureLock™ Midi-Cell (Invitrogen) using 1× NuPAGE® 2-(N-morpholino)-ethanesulfonic acid (MES)/SDS running buffer (Invitrogen), and stained using SimplyBlue™ SafeStain (Invitrogen) according to supplied instruction manuals.

The electrophoretic separation of the fluorescently labeled E. coli lysate and a pre-labeled standard (SeeBlue® Plus2 Protein Standard (Invitrogen, Carlsbad)) is shown in the gel images given in FIG. 8A, with the image obtained using Fujifilm LAS-1000 with a 477 nm EPI light source, 520-640 nm band pass filter and exposure time of 30 seconds. FIG. 8B is a post stain with SimplyBlue™ SafeStain to demonstrate the effectiveness of the labeling method. The labeled samples correspond to the following gel lanes given in the gel images of FIG. 8A and FIG. 8B:

| Gel Lane | Sample and Time |
|---|---|
| 1. | E. coli lysate (reduced) for 10 min. |
| 2. | E. coli lysate (reduced) for 30 min. |
| 3. | E. coli lysate (reduced) for 1 hour |
| 4. | 10 µl SeeBlue ® Plus2 Prestained Standard (Invitrogen, Carlsbad) |

Example 5: Labeling of Cell Lysate

The labeling of cell lysate with amine fluorogenic reagents using the methods described herein was demonstrated by labeling rat liver lysate. The protein lysozyme was also labeled as a comparison.

The rat liver lysate was labeled in micro-centrifuge tubes by initially adding 5 µl of the 10× labeling solution to 5 µl of a rat liver lysate and incubate at room temperature for 10 minutes. Then for each sample 2 µl of 5×LDS/sucrose, 6 µl of 0.91 M bis-Tris (pH 6.5) and 2 µl of NuPAGE® Sample Reducing Agent (10×), were added, and the mixtures were incubated at 70° C. for 10 minutes. After incubation the mixtures were diluted using either 1× NuPAGE® Sample Buffer or 1× bis-Tris/LDS/sucrose to achieve.

Lysozyme was labeled in micro-centrifuge tubes by initially adding 5 µl of the 10× labeling solution to 5 µl of a 1 mg/mL lysozyme stock solution and incubated at room temperature for 10 minutes. Then 2 µl of 5×LDS/sucrose, 6 µl of 0.91 M bis-Tris (pH 6.5) and 2 µl of NuPAGE® Sample Reducing Agent (10×) were added, resulting in 0.125 mg/ml concentration of protein, and this mixture was then incubated at 70° C. for 10 minutes. After incubation the mixtures were further diluted using either 1× NuPAGE® Sample Buffer or 1× bis-Tris/LDS/sucrose to achieve 0.1 mg/ml protein concentrations.

The electrophoretic separation of the labeled lysate, lysozyme and a pre-labeled protein standard was achieved by loading 2 µl of the labeled rat liver lysate (20 µg per lane) and 2 µl of the lysozyme (1 µg per lane) into NuPAGE® 4-12% Bis-Tris gels (Invitrogen), electrophoresing at 200 volts in either an XCell SureLock™ Mini-Cell (Invitrogen) or XCell4 SureLock™ Midi-Cell (Invitrogen) using 1× NuPAGE® 2-(N-morpholino)-ethanesulfonic acid (MES)/SDS running buffer (Invitrogen), and stained using SimplyBlue™ SafeStain (Invitrogen) according to supplied instruction manuals.

FIG. 9A and FIG. 9B illustrates the labeling of different proteins using the methods described herein. FIG. 9A are gel images of labeled lysozyme (reduced, lane 1) and SeeBlue Plus2 (lane 2, stained with SimplyBlue Safe Stain), while FIG. 9B are gel images of SeeBlue Plus2 (lane 1, stained with SimplyBlue Safe Stain) and labeled rat liver lysate (lane 3), with lane 2 empty. Fluorescent image obtained using Fujifilm LAS-1000 with a 477 nm EPI light source, 520-640 nm band pass filter and exposure time of 30 seconds.

Example 6: Labeling Under Native Conditions

FIG. 10A and FIG. 10B shows that the methods described herein can be used to label proteins with amine reactive fluorogenic reagents under native conditions, wherein the proteins have different molecular weights and number of reactive groups (e.g., lysine residues). FIG. 10A and FIG. 10B also illustrates the proportionality of fluorescence signal to the amount of labeled protein present and the use of the labeling methods described herein to maintain fluorescence signal intensity through the reduction process. The proteins labeled were bovine serum albumin (BSA), myoglobin, h-IgG and E. coli lysate.

The labeling and electrophoretic separation of the bovine serum albumin (BSA), myoglobin, h-IgG and E. coli lysate were as that described in the above examples.

FIG. 10A is the gel image after staining with SimplyBlue™ SafeStain, while FIG. 10B is a gel image of h-IgG, myoglobin, and BSA labeled using the methods described herein. The labeled samples were separated in the following gel lanes:

| Gel Lane | Sample and Time |
|---|---|
| 1. | 6 µl Mark12 ™ Unstained Standard (Invitrogen, Carlsbad) |
| 2. | 0.5 µg labeled h-IgG, non-reduced |
| 3. | 1 µg labeled h-IgG, non-reduced |
| 4. | 0.5 µg labeled h-IgG, reduced |
| 5. | 1 µg labeled h-IgG, reduced |
| 6. | 0.5 µg labeled myoglobin, non-reduced |
| 7. | 1 µg labeled myoglobin, non-reduced |
| 8. | 0.5 mg labeled myoglobin, reduced |
| 9. | 1 µg labeled myoglobin, reduced |
| 10. | 0.5 µg labeled BSA, non-reduced |
| 11. | 1 µg labeled BSA, non-reduced |
| 12. | 0.5 µg labeled BSA, reduced |
| 13. | 1 µg labeled BSA, reduced |
| 14. | 2 µg labeled E. coli lysate, non-reduced |
| 15. | 4 µg labeled E. coli lysate, non-reduced |
| 16. | 2 µg labeled E. coli lysate, reduced |
| 17. | 4 µg labeled E. coli lysate, reduced |
| 18. | 0.5 µg labeled BSA, non-reduced control, denatured during labeling |
| 19. | 0.5 µg labeled BSA, reduced control, denatured during labeling |
| 20. | 6 µl Mark12 ™ Unstained Standard (Invitrogen, Carlsbad) |

Example 7: Labeling Under Denaturing Conditions with Varied Concentrations of Reactants Protein labeling under denaturing conditions and the effect of reactant concentration on the fluorescence intensity of labeled proteins on the was obtained by labeling h-IgG, myoglobin, bovine serum albumin (BSA) and E. coli lysate with amine reactive fluorogenic reagents as described in the above examples. To demonstrate the effect of reactant concentration proteins were labeled using either the 10× labeling solution or the 1× labeling solution.

The results of the various labeling conditions are shown in the gel images of FIG. 11A and FIG. 11B wherein h-IgG, myoglobin, BSA and E. coli lysate were labeled with LDS and sucrose present in the labeling reaction. The upper gel images are the gels stained with SimplyBlue™ SafeStain, while the lower gel images are of the fluorescently labeled h-IgG, Myoglobi, BSA and E. coli lysate. In addition non-labeled protein standards (Mark12™ Unstained Standard (Invitrogen, Carlsbad)) were electrophoresed along with the labeled proteins. The labeled samples correspond to the following gel lanes given in the gel images of FIG. 11A and FIG. 11B:

| Gel A Lane | Sample |
|---|---|
| 1. | 0.5 µg h-IgG, 10X labeled, non-reduced |
| 2. | 6 µl Mark12 ™ Unstained Standard (Invitrogen, Carlsbad) |
| 3. | 1 µg h-IgG, 10X labeled, non-reduced |
| 4. | 0.5 µg h-IgG, 10X labeled, reduced |
| 5. | 1 µg h-IgG, 10X labeled, reduced |
| 6. | 0.5 µg h-IgG, 1X labeled, non-reduced |
| 7. | 1 µg h-IgG, 1X labeled, non-reduced |
| 8. | 0.5 µg h-IgG, 1X labeled, reduced |
| 9. | 1 µg h-IgG, 1X labeled, reduced |
| 10. | 0.5 µg myoglobin, 10X labeled, non-reduced |
| 11. | 1 µg myoglobin, 10X labeled, non-reduced |
| 12. | 0.5 µg myoglobin, 10X labeled, reduced |
| 13. | 1 µg myoglobin, 10X labeled, reduced |
| 14. | 0.5 µg myoglobin, 1X labeled, non-reduced |
| 15. | 1 µg myoglobin, 1X labeled, non-reduced |
| 16. | 0.5 µg myoglobin, 1X labeled, reduced |
| 17. | 1 µg myoglobin, 1X labeled, reduced |
| 18. | 1 µg labeled BSA, non-reduced control |
| 19. | 6 µl Mark12 ™ Unstained Standard (Invitrogen, Carlsbad) |
| 20. | 1 µg labeled BSA, reduced control |

| Gel B Lane | Sample |
|---|---|
| 1. | 0.5 µg BSA, 10X labeled, non-reduced |
| 2. | 1 µg BSA, 10X labeled, non-reduced |
| 3. | 6 µl Mark12 ™ Unstained Standard (Invitrogen, Carlsbad) |
| 4. | 0.5 µg BSA, 10X labeled, reduced |
| 5. | 1 µg BSA, 10X labeled, reduced |
| 6. | 0.5 µg BSA, 1X labeled, non-reduced |
| 7. | 1 µg BSA, 1X labeled, non-reduced |
| 8. | 0.5 µg BSA, 1X labeled, reduced |
| 9. | 1 µg BSA, 1X labeled, reduced |
| 10. | 2 µg E. coli lysate, 10X labeled, reduced |
| 11. | 4 µg E. coli lysate, 10X labeled, reduced |
| 12. | 2 µg E. coli lysate, 10X labeled, re-reduced |
| 13. | 4 µg E. coli lysate, 10X labeled, re-reduced |
| 14. | 2 µg E. coli lysate, 1X labeled, reduced |
| 15. | 4 µg E. coli lysate, 1X labeled, reduced |
| 16. | 2 µg E. coli lysate, 1X labeled, re-reduced |
| 17. | 4 µg E. coli lysate, 1X labeled, re-reduced |
| 18. | 6 µl Mark12 ™ Unstained Standard (Invitrogen, Carlsbad) |
| 19. | 1 µg labeled BSA, non-reduced control |
| 20. | 1 µg labeled BSA, reduced control |

Example 8: Band Sharpness and Fluorescence Intensity of Labeled Protein as a Function of Reactant Concentrations and Labeling Time The protein labeling methods using amine reactive fluorogenic reagents described herein result in sharp bands as observed in gel electrophoreses. The effect of band sharpness was shown by labeling bovine serum albumin (BSA) with amine reactive fluorogenic reagents using the methods described herein using various reactant concentrations and labeling time. In addition, the labeling of BSA demonstrated that such labeling methods do not cause fluorescent signal losses upon reduction of labeled protein. BSA was labeled using the procedure described above however the reactant concentrations were varied by using either the 10× labeling solution or the 1× labeling solution, and labeling times were either 15 minutes or 1 hour. Different concentrations of labeled BSA were then separated as described in the examples above. FIG. 12 shows that band sharpness is not affected by the various reaction conditions. The upper gel image is a fluorescent image of the labeled BSA, while the lower image is the gel after staining with SimplyBlue™ SafeStain. An un-labeled protein standard (Mark12™ Unstained Standard (Invitrogen, Carlsbad)) was included for comparison. The fluorescence image was obtained using Fujifilm's LAS-1000 with a 477 nm EPI light source, a 520-640 nm band pass filter and an exposure time of 1 minute. The labeled samples were separated in the following gel lanes:

| Gel Lane | Sample and Time |
|---|---|
| 1. | 6 µl Mark12 ™ Unstained Standard (Invitrogen, Carlsbad) |
| 2. | 0.5 µg BSA, 10X concentrations, labeled for 15 minutes, non-reduced |
| 3. | 1 µg BSA, 10X concentrations, labeled for 15 minutes, non-reduced |
| 4. | 0.5 µg BSA, 10X concentrations, labeled for 15 minutes, reduced |
| 5. | 1 µg BSA, 10X concentrations, labeled for 15 minutes, reduced |
| 6. | 0.5 µg BSA, 10X concentrations, labeled for 1 hour, non-reduced |
| 7. | 1 µg BSA, 10X concentrations, labeled for 1 hour, non-reduced |

-continued

| Gel Lane | Sample and Time |
|---|---|
| 8. | 0.5 µg BSA, 10X concentrations, labeled for 1 hour, reduced |
| 9. | 1 µg BSA, 10X concentrations, labeled for 1 hour, reduced |
| 10. | 0.5 µg BSA, 1X concentrations, labeled for 15 minutes, non-reduced |
| 11. | 1 µg BSA, 1X concentrations, labeled for 15 minutes, non-reduced |
| 12. | 0.5 µg BSA, 1X concentrations, labeled for 15 minutes, reduced |
| 13. | 1 µg BSA, 1X concentrations, labeled for 15 minutes, reduced |
| 14. | 0.5 µg BSA, 1X concentrations, labeled for 1 hour, non-reduced |
| 15. | 1 µg BSA, 1X concentrations, labeled for 1 hour, non-reduced |
| 16. | 0.5 µg BSA, 1X concentrations, labeled for 1 hour, reduced |
| 17. | 1 µg BSA, 1X concentrations, labeled for 1 hour, reduced |

Example 9: Protein Labeling and Digestion

The labeling of proteins with amine reactive fluorogenic reagents using the methods described herein, followed by digestion of the labeled protein was demonstrated by labeling bovine serum albumin at elevated temperature, optionally reducing the labeled mixture and then electrophoretically separating the mixture. BSA was labeled as described in the examples above at room temperature and at 70° C. FIG. 13 (panel 1) illustrates that labeling at elevated temperature results in a gel foot of small labeled protein fragments which consequently "over saturates" the detector and this fluorescence prevents visualization of the less fluorescently intense labeled proteins. Removal of the gel foot (cutting out) allows for visualization of the other labeled proteins or protein fragments in the gel (FIG. 13 (panel 2)). Illustrated in panel 2 is the presence of protein fragments due to digestion of the protein at elevated temperature during labeling. Also shown in FIG. 13 (panels 3 and 4) is the ability to reversibly quench the fluorescence at low pH and achieve full fluorescence recovery at high pH. Therefore, the fluorescence signal obtained using the labeling methods described herein for amine reactive fluorogenic reagents is pH-dependent. Fluorescent images were obtained using Fujifilm's LAS-1000 with a 477 nm EPI light source, a 520-640 nm band pass filter and exposure times of 1 minute. Lane 1 of the gel is SeeBlue Plus 2 (Invitrogen) pre-stained standard which contains fluorescently labeled proteins. The remaining gel lanes are sample sets are described below:

| Gel Lane | Sample and Time |
|---|---|
| 1. | 10 µl SeeBlue ® Plus2 Prestained Standard (Invitrogen, Carlsbad) |
| 2. | 1 µg BSA, labeled at room temperature, reduced |
| 3. | 0.5 µg BSA, labeled at room temperature, reduced |
| 4. | 0.5 µg BSA, labeled at room temperature, non-reduced |
| 5. | 1 µg BSA, labeled at room temperature, non-reduced |
| 6. | 1 µg BSA, labeled at 70° C., reduced |
| 7. | 0.5 µg BSA, labeled at 70° C., reduced |
| 8. | 1 µg BSA, labeled at 70° C., non-reduced |
| 9. | 0.5 µg BSA, labeled at 70° C., non-reduced |
| 10. | 10 µl MagicMark™ XP Standard (Invitrogen, Carlsbad) |

Example 10: Protein Expression Analysis: E. coli Lysate

E. coli were transformed with a tetracysteine tag (TC)-tagged GFP (green fluorescent protein) plasmid construct tagged at the C-terminus. The cells were grown up overnight with shaking at 37° C. in Luria-Bertani (LB)/antibiotic to an OD600 of 0.8-1.0. Samples of each were removed and the remainder was induced with 1 mM IPTG (isopropyl β-D-1-thiogalactopyranoside) and incubated with shaking for 30 minutes. The cells were aliquoted, centrifuged at 4,000×g for 10 minutes, the media was aspirated off and the pellets were stored at −20° C.

For each experiment, an aliquot of pelleted cells was brought to room temperature, resuspended in 1% SDS to lyse the cells, vortexed, heated to 70° C., vortexed again, and centrifuged at 14,000×g for 5 minutes to pellet the cellular debris. The supernatant was used as the experimental lysate. When the protein of interest was soluble in PBS, then 1×PBS was also used to resuspend the cell pellet and cells were lysed with sonication.

One tube of pelleted cells was brought to room temperature and resuspended in 100 µl 1% SDS, vortexed, heated at 70° C. for 10 minutes, vortexed again, and centrifuged at 14,000×g for 10 minutes. A second tube of pelleted cells was resuspended in 100 µl 1×PBS, sonicated and centrifuged at 14,000×g for 10 minutes.

A loading buffer (also referred to as FlAsH buffer) containing (as a 2× buffer): 4% SDS, 20% glycerol, 120 mM potassium phosphate buffer pH 8.5, 0.4 mg/mL bromophenol blue, 50 mM mercaptoethanesulfonic acid, 2 mM tris [2-carboxyethyl] phosphine (TCEP), 20 µM 4'-5-bis(1,3,2-dithioarsolan-2-yl)fluorescein-(2,2-ethanedithiol)$_2$. (FlAsH) and 333 µM NaHCO$_3$ was used to label the TC tagged proteins. For each tube, 6 µl of loading buffer (FlAsH buffer) was added to 4 µl of lysate. Control samples were prepared similarly, however a loading buffer without the FlAsH reagent (replaced with water) was used to show the independence of whole protein staining from FlAsH and that the TC-tagged protein is only detected in the presence of the FlAsH reagent. Each sample was vortexed and quickly spun down then incubated 3 minutes at 70° C. After 3 minutes, the sample was placed at room temperature and 2 µl of an amine reactive dye in DMSO was added for total protein measurement. In some samples the amine reactive dye used was BODIPY TR-X SE, while in other samples the amine reactive dye was BODIPY 650/665 SE. The final concentrations of BODIPY TR-X SE was 12.5 µM, obtained from a stock solution of 125 µM, and the final concentration of BODIPY 650/665 SE was 10 µM, obtained from a stock solution of 10 µM. Control samples without total protein dye had 2 µl DMSO added. All samples were vortexed and incubated at room temperature for ten minutes and then 10 µl of each was loaded on a NuPage 4-12% Bis-Tris SDS-PAGE gel and a Novex 4-20% Tris-Glycine gel and electrophoresed according to the corresponding gel protocol. The NuPage gel was run in 3-(N-morpholino)-propanesulfonic acid (MOPS) running buffer and the Novex gel was run in Novex running buffer. Both were run at 200V for one hour.

After electrophoresis was complete, the gels were then placed, in their cassettes, on a fluorescent imager (Fuji FLA3000) and imaged with a 473 nm excitation laser and 520 nm emission filter to detect the TC-tagged GFP protein labeled with FlAsH. The cassette was then imaged with either a 532 nm excitation laser and 580 nm emission filter (for detection of BODIPY TR-X) or a 633 nm excitation laser and a 675 nm emission filter (for detection of BODIPY 650/665) depending on which amine reactive protein dye was added to the sample to detect the total protein lysate profile. FIGS. 17-19 show the gel images obtained. Samples obtained from the supernatant from the first tube were used in lanes 1-12 and samples obtained from the supernatant from the second tube was used in lanes 13-15 (for Novex gel) or 13-17 (for NuPage gel) as described below. The gels were loaded with sample treated as follows:

| Gel Lane | Sample |
|---|---|
| 1. | Benchmark pre-stained ladder (10 µl, untreated) |
| 2. | lysate + loading buffer |
| 3. | lysate + loading buffer |
| 4. | lysate + loading buffer |
| 5. | lysate + FlAsH buffer |
| 6. | lysate + FlAsH buffer |
| 7. | lysate + FlAsH buffer |
| 8. | lysate + FlAsH buffer + BODIPY TR-X |
| 9. | lysate + FlAsH buffer + BODIPY TR-X |
| 10. | lysate + FlAsH buffer + BODIPY TR-X |
| 11. | lysate + loading buffer + BODIPY TR-X |
| 12. | lysate + loading buffer + BODIPY TR-X |
| 13. | lysate + FlAsH buffer + BODIPY 650/665 |
| 14. | lysate + FlAsH buffer + BODIPY 650/665 |
| 15. | lysate + FlAsH buffer + BODIPY 650/665 |
| 16. | lysate + loading buffer + BODIPY 650/665 |
| 17. | lysate + loading buffer + BODIPY 650/665 |

Note:
In the Novex gel, which has 15 lanes instead of 17, lanes 1-14 are as indicated and lane 15 contains sample for lane 16.

In the image obtained with a 473 nm excitation and 520 nm emission (FIG. 17), the TC-tagged protein GFP is visible in lanes 5 through 10. In the lanes without the FlAsH loading buffer (2-4, 11-12 and 16-17), the TC-tagged protein is not visible. In the image obtained with a 532 nm excitation and 580 nm emission (FIG. 18), the total protein profiles from the lysates labeled with BODIPY TR-X SE are visible (lanes 8-12). In the image obtained with a 633 nm excitation and 675 nm emission (FIG. 19), the total protein profiles from the lysates labeled with BODIPY 650/665 SE are visible (lanes 13-17). The total protein profiles are visible in the lanes without the FlAsH reagent in the loading buffer as well (lanes 11-12 and 16-17) showing independence between FlAsH labeling of TC-tagged proteins and total protein labeling with BODIPY SE dyes.

Example 11: Protein Expression Analysis: Mammalian Cell Lysate and Protein Ladders The protocol and loading buffer described in example 10 also work with protein ladders and mammalian cell lysate.

E. coli were transformed with a tetracysteine tag (TC)-tagged GFP (green fluorescent protein) plasmid construct tagged at the C-terminus. The cells were grown up overnight with shaking at 37° C. in Luria-Bertani (LB)/antibiotic to an OD600 of 0.8-1.0. Samples of each were removed and the remainder was induced with 1 mM IPTG (isopropyl β-D-1-thiogalactopyranoside) and incubated with shaking for 30 minutes. The cells were aliquoted, centrifuged at 4,000×g for 10 minutes, the media was aspirated off and the pellets were stored at −20° C.

Mammalian cells were transformed with a tetracysteine tag (TC)-tagged CFP (cyan fluorescent protein) plasmid construct tagged at the C-terminus. The cells were grown up overnight with shaking at 37° C. in Luria-Bertani (LB)/antibiotic to an OD600 of 0.8-1.0. Samples of each were removed and the remainder was induced with 1 mM IPTG (isopropyl β-D-1-thiogalactopyranoside) and incubated with shaking for 30 minutes. The cells were aliquoted, centrifuged at 4,000×g for 10 minutes, the media was aspirated off and the pellets were stored at −20° C.

For each experiment, an aliquot of pelleted cells was brought to room temperature, resuspended in 1% SDS to lyse the cells, vortexed, heated to 70° C., vortexed again, and centrifuged at 14,000×g for 5 minutes to pellet the cellular debris. The supernatant was used as the experimental lysate. When the protein of interest was soluble in PBS, then 1×PBS was also used to resuspend the cell pellet and cells were lysed with sonication.

One tube of pelleted E. coli cells was brought to room temperature and resuspended in 100 µl 1% SDS, vortexed, heated at 70° C. for 10 minutes, vortexed again, and centrifuged at 14,000×g for 10 minutes. A second tube of pelleted mammalian cells was resuspended in 100 µl 1×PBS, sonicated and centrifuged at 14,000×g for 10 minutes. It was later found that the TC-tagged CFP expressed in the mammalian cells was not complete but rather degraded. Even when 1% SDS was used to lyse the mammalian cells, the TC-tagged CFP was not detected.

A loading buffer (also referred to as FlAsH buffer) containing (as a 2× buffer): 4% SDS, 20% glycerol, 120 mM potassium phosphate buffer pH 8.5, 0.4 mg/mL bromophenol blue, 50 mM mercaptoethanesulfonic acid, 2 mM tris [2-carboxyethyl] phosphine (TCEP), 20 µM 4'-5'-bis(1,3,2-dithioarsolan-2-yl)fluorescein-(2,2-ethanedithiol)$_2$. (FlAsH) and 333 µM NaHCO$_3$ was used to label the TC tagged proteins. For each tube, 6 µl of loading buffer (FlAsH buffer) was added to 4 µl of lysate (E. coli and mammalian). Each sample was vortexed and quickly spun down then incubated 3 minutes at 70° C. After 3 minutes, the sample was placed at room temperature and 2 µl of an amine reactive dye in DMSO was added for total protein measurement. In some samples the amine reactive dye used was BODIPY TR-X SE, while in other samples the amine reactive dye was BODIPY 650/665 SE. The final concentrations of BODIPY TR-X SE was 125 µM, obtained from a stock solution of 1.25 mM, and the final concentration of BODIPY 650/665 SE were 10 µM, obtained from a stock solution of 10 µM. It was also found that the total protein dyes also work when mixed together.

The protein ladders BenchMark™ Protein Ladder (Invitrogen, Carlsbad) and Mark12™ Unstained Standard (Invitrogen, Carlsbad) were labeled with amine reactive fluorescent dyes by adding 2 µl of an amine reactive dye (BODIPY TR-X SE, BODIPY 650/665 SE or both) in DMSO to the protein ladder solutions.

All samples were vortexed and incubated at room temperature for ten minutes and then 10 µl of each was loaded on a NuPage 4-12% Bis-Tris SDS-PAGE gel and a Novex 4-20% Tris-Glycine gel and electrophoresed according to the corresponding gel protocol. The NuPage gel was run in 3-(N-morpholino)-propanesulfonic acid (MOPS) running buffer and the Novex gel was run in Novex running buffer. Both were run at 200V for one hour.

After electrophoresis was complete, the gels were then placed, in their cassettes, on a fluorescent imager (Fuji FLA3000) and imaged with a 473 nm excitation laser and 520 nm emission filter to detect the TC-tagged GFP protein and TC-tagged CFP protein labeled with FlAsH. The cassette was then imaged with either a 532 nm excitation laser and 580 nm emission filter (for detection of BODIPY TR-X) or a 633 nm excitation laser and a 675 nm emission filter (for detection of BODIPY 650/665) depending on which amine reactive protein dye was added to the sample to detect the total protein lysate profile. FIGS. 20-22 show the gel images obtained. Samples for labeled BenchMark™ Protein Ladder (Invitrogen, Carlsbad) were loaded into lanes 3-5, samples obtained from the *E. coli* supernatant were used in lanes 6-9, samples obtained from the mammalian cell supernatant were used in lanes 10-12, and samples for labeled Mark12™ Unstained Standard (Invitrogen, Carlsbad) were used in lanes 13-15.

| Gel Lane | Sample |
|---|---|
| 1. | Benchmark pre-stained ladder (10 ul, un-treated) |
| 2. | Benchmark fluorescent ladder (5 ul, un-treated) |
| 3. | Benchmark ladder (2 ul) + BODIPY TR-X |
| 4. | Benchmark ladder (2 ul) + BODIPY 650/665 |
| 5. | Benchmark ladder (2 ul) + BODIPY TR-X + BODIPY 650/665 |
| 6. | GFP-TC lysate + DMSO (no whole protein dye) |
| 7. | GFP-TC lysate + BODIPY TR-X |
| 8. | GFP-TC lysate + BODIPY 650/665 |
| 9. | GFP-TC lysate + BODIPY TR-X + BODIPY 650/665 |
| 10. | mammalian lysate + BODIPY TR-X |
| 11. | mammalian lysate + BODIPY 650/665 |
| 12. | mammalian lysate + BODIPY TR-X + BODIPY 650/665 |
| 13. | Mark 12 ladder + BODIPY TR-X |
| 14. | Mark 12 ladder + BODIPY 650/665 |
| 15. | Mark 12 ladder + BODIPY TR-X + BODIPY 650/665 |

The images shown in FIGS. 20-22 also demonstrate that proteins present in mammalian lysates with TC-like regions can be detected with the FlAsH loading buffer and their relative abundance is indicated by the total protein labeling.

It should be understood that the foregoing description is only illustrative of the invention. Headings are for convenience only and are not intended to limited disclosure falling under a heading to only that heading. Various alternatives and modifications can be devised by those skilled in the art without departing from the invention. Accordingly, the present invention is intended to embrace all such alternatives, modifications and variances which fall within the scope of the appended claims.

While the invention has been described in conjunction with the preferred embodiments, it will be understood that they are not intended to limit the invention to those embodiments. On the contrary, the invention is intended to cover alternatives, modifications, and equivalents, which may be included within the scope of the invention as defined by the appended claims.

All publications, patents and patent applications mentioned in this specification are herein incorporated by reference in their entirety to the same extent as if each individual publication, patent or patent application was specifically and individually indicated to be incorporated by reference.

What is claimed is:

1. A kit for fluorescently labeling a mixture of proteins comprising a tagged protein, said kit comprising:
   a) a first labeling composition comprising:
      a first buffer having a pH in the range from pH 8 to pH 10;
      an amine reactive fluorogenic reagent or an amine reactive fluorescent dye; and
      a cyanohydrin or mandelonitrile,
      wherein said first buffer does not include buffer components or additives that have primary or secondary amine moieties; and
   b) a second labeling composition comprising a second buffer in the range from pH 6 to pH 10, and a tag binding fluorogenic reagent.

2. The kit of claim 1, wherein the first labeling composition comprises an amine reactive fluorogenic reagent.

3. The kit of claim 2, wherein said amine reactive fluorogenic reagent is 3-(4-carboxybenzoyl)quinoline-2-carboxaldehyde or 3-(2-furoyl)quinoline-2-carboxaldehyde).

4. The kit of claim 1, wherein the first labeling composition comprises an amine reactive fluorescent dye comprising a fluorescent moiety selected from the group consisting of a fluorescein moiety, a rhodamine moiety, an acridine moiety, a coumarin moiety, an indole moiety, an isoindole moiety, an indolizine moiety, a quinoline moiety, an isoquinoline moiety, a chromene moiety, a xanthene moiety, a naphthalene moiety, a pyrene moiety, a bimane moiety and a BODIPY moiety.

5. The kit of claim 1, wherein the second labeling composition further comprises a tag binding fluorogenic reagent that binds to at least four cysteine moieties, and at least one reducing agent, and wherein the amine reactive fluorogenic reagent or fluorescent dye of the first labeling composition has a first emission wavelength and the tag binding fluorogenic dye of the second labeling composition has a second emission wavelength, and the first emission wavelength and the second emission wavelength are different.

6. The kit of claim 5, wherein the tag binding fluorogenic reagent is a biarsenical derivative of fluorescein or resorufin.

7. The kit of claim 1, wherein said first labeling composition further comprises one or more of an anionic surfactant, a sugar or sugar alcohol, or an alkylating agent.

8. The kit of claim 1, wherein said first labeling composition comprises acetone cyanohydrin.

9. The kit of claim 1, wherein said first labeling composition comprises mandelonitrile.

10. The kit of claim 1 wherein said first labeling composition comprises acetone cyanohydrin and a mandelonitrile.

11. The kit of claim 1, wherein said first buffer is selected from the list consisting of carbonate/bicarbonate buffer, phosphate buffer, borate buffer, and N,N-Bis(2-hydroxyethyl)glycine (Bicine) buffer.

12. The kit of claim 1, wherein said first buffer is a carbonate/bicarbonate buffer.

* * * * *